US006242428B1

(12) United States Patent
Weis et al.

(10) Patent No.: US 6,242,428 B1
(45) Date of Patent: *Jun. 5, 2001

(54) NUCLEOSIDE ANALOGS AND USES IN TREATING *PLASMODIUM FALCIPARUM* INFECTION

(75) Inventors: Alexander L Weis; Kirupathevy Pulenthiran, both of San Antonio, TX (US); Annette M. Gero, Cremorne (AU)

(73) Assignees: Unisearch Limited, New S. Wales (AU); Lipitek International Inc., San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/219,947

(22) Filed: Dec. 23, 1998

Related U.S. Application Data

(63) Continuation-in-part of application No. 08/531,875, filed on Sep. 21, 1995, now Pat. No. 6,025,335.

(51) Int. Cl.[7] ................................................. A01N 43/04
(52) U.S. Cl. ................................. 514/44; 514/45; 514/46; 514/47; 514/48; 514/49; 514/50; 514/51; 514/895

(58) Field of Search .................................. 514/44, 45, 46, 514/47, 48, 49, 50, 51, 895

(56) References Cited

U.S. PATENT DOCUMENTS

| 5,552,535 | * | 9/1996 | McLean et al. . |
| 5,571,902 | * | 11/1996 | Ravikumar et al. . |
| 5,608,046 | * | 3/1997 | Cook et al. . |
| 5,614,505 | * | 3/1997 | Gmeiner et al. . |
| 5,939,402 | * | 8/1999 | Weis et al. . |

FOREIGN PATENT DOCUMENTS

| 0540741 | 7/1991 | (EP) | .......................................... 21/4 |
| 0121635 | 10/1984 | (FR) | ....................................... 19/20 |

OTHER PUBLICATIONS

Kikkawa, M. et al., "Synthesis and antitumor activities of 5–fluorouracil dinocleotide analogs;" Nucleic Acids Symp. Ser.; vol. 31, 1994, pp. 6.

* cited by examiner

*Primary Examiner*—James O. Wilson
(74) *Attorney, Agent, or Firm*—Fulbright & Jaworski L.L.P.

(57) ABSTRACT

The invention relates to novel nucleosides and nucleoside dimers containing an L-sugar in at least one of the nucleosides, and their pharmaceutical compositions.

55 Claims, 21 Drawing Sheets

3'-5' IBA Compounds  5'-5' IBA Compounds  3'-3' IBA Compounds where IBA =

A)

B)

Synthesis of α-LdU, Cordycepin Dimer L-152

Synthesis of β-L- dC, Cordycepin Dimer L-153

Synthesis of α-LdC, Cordycepin Dimer L-154

Synthesis of α-dA, Cordycepin Dimer L-155

Synthesis of β-LdA, β-D-dA, Dimer L-210

Methox phosphotriesters

Methyl phosphonates

Phosphorodithioates

Silyl Ethers

Sulfonates

Ethylenedioxy ethers

Phosphorothioates

BO1  R₁=SATE, R₂=H
BO2  R₁=H, R₂=SATE
BO3  R₁=R₂=SATE

BO4  R₁=H, R₂=SATE
BO5  R₁=R₂=SATE

BO6  R₁=H, R₂=SATE
BO7  R₁=R₂=SATE

SATE:

NUCLEOSIDE ANALOGS AND USES IN TREATING *PLASMODIUM FALCIPARUM* INFECTION

This Application is a continuation-in-part from U.S. patent application Ser. No. 08/531,875, filed on Sep. 21, 1995, now U.S. Pat. No. 6,025,335.

BACKGROUND OF THE INVENTION

1. Field of Invention

This invention relates to novel nucleosides and dinucleoside dimers and derivatives of these compounds, including, L-deoxyribofuranosyl nucleoside phosphodiester dimers in which the sugar moiety of at least one of the nucleosides has an L-configuration. These compounds may be used to treat parasitic infection by *Plasmodium falciparum,* the etiologic agent responsible for the most fatal form of malaria.

2. Prior Art

Modified nucleoside analogs are an important class of antineoplastic and antiviral drugs. The present application discloses novel compounds for of this type for use in the treatment of *P. falciparum* infection. *Plasmodium falciparum* is the etiologic agent responsible for the most fatal form of malaria, a disease which afflicts between 200 and 300 million people per year (all forms), including over one million childhood deaths. Additionally, greater than 40% of the world's population lives in areas in which malaria is at epidemic levels. Due to the extraordinary morbidity and mortality associated with malaria, malaria-related research has intensified during the past decade in a desperate search for an effective treatment. A safe and effective vaccine still does not exist. Instead, malaria victims must depend upon chemotherapy. However, these analogs may be used to treat various other parasitic infections.

These chemotherapeutic agents can be classified into two groups: those that act post-translationally, and those that act by interfering with nucleic acid synthesis.

Most drugs are in the first group, which means that they exert their therapeutic effect by interfering with a cell's protein synthesis, and hence its metabolism (rather than its nucleic acid synthesis). Examples of drugs in this group include: the antifolate compounds (which inhibit dihyrdofolate reductase), and sulfonamide drugs (which inhibit dihydropteroate synthetase. Yet these drugs have serious drawbacks. The protozoan responsible for malaria very quickly develops resistance to these drugs. The reason is that, since resistance occurs through adaptive mutations in successive generations of the parasite, a one or two point mutation is often sufficient to confer resistance.

The second group of compounds includes the nucleic acid intercalators such as acridines, phenanthrenes and quinolines. These intercalators partially mimic the biochemical activity of nucleic acids, and therefore are incorporated into the protozoan's nucleic acid (DNA and RNA), though once incorporated, do not allow further nucleic acid synthesis, hence their effectiveness. At the same time, these intercalators interfere with host nucleic acid synthesis as well, and thus give rise to toxic side effects. Because of the potential for toxic side effects, these drugs can quite often be given only in very small doses. Once again, a resistance pattern may develop. For example, the protozoan responsible for malaria is known to develop "cross-resistance," which means that the parasite develops resistance to other classes of drugs even though it was exposed on a different class of drug.

Indeed, all of the currently known drugs or drug candidates utilizing the delivery of cytotoxic pyrimidine or purine biosynthesis inhibitors to invading cells are extremely toxic. Therefore, while drugs of this type-i.e., those that interfere with nucleic acid synthesis-are effective, they lack selectivity. It is this latter parameter that must be maximized in the development of a safe and effective drug. In other words, such a drug would target host tissues that are infected, or cancerous, yet leave the host tissue unchanged.

Recent advances in our understanding of the biochemistry of parasite cells serves as a valuable example regarding the design of effective therapies. One investigator (H. Ginsburg, Biochem. Pharmacol. 48, 1847–1856 (1994)) observed that normal and parasite-infected erythrocytes exhibit significant differences with respect to purine and pyrimidine metabolism in single enzymes, as well as in whole branches of related pathways. The parasite satisfies all of its purine requirements through scavenger pathways; meanwhile, the host cell lacks the enzymes necessary to exploit this pathway, and so therefore must meet its pyrimidine requirements largely through de novo synthesis. Put another way, the parasite is more efficient than normal or host cells since it can synthesize the nucleic acid building blocks.

Other investigators (G. Beaton, D. Pellinqer, W. S. Marshall & M. H. Caruthers, In: *Oligonucleotides and Analogues: A Practical Approach,* F. Eckstein Ed., IRL Press, Oxford, 109–136 (1991)) have established that a malaria-infected erythrocyte is capable of effectively transporting the non-naturally occurring "L-nucleosides" (in contrast to the "D-nucleosides" which are the naturally occurring form) for use in nucleic acid synthesis. Yet, normal mammalian cells are nonpermeable to this class of compounds, which suggests that the L-nucleosides are non-toxic to normal mammalian or host cells. Thus, derivatives of these compounds may be used as highly selective drugs against parasite infection, or against any other type of cell or organism utilizing the L-nucleosides. The chemical modification of the L-nucleosides consists generally of modifying the nucleosides so that they are still recognized by the invading cell or organism's nucleic acid synthetic machinery, and therefore incorporated into a nucleic acid chain, but yet once this incorporation occurs, no further synthesis will take place.

Currently, there are no therapeutic compounds in use that are based on dimers of these nucleoside analogs. While dimers of the naturally occurring D-deoxyribofuranosyl nucleosides are well known, dimers in which one or both nucleosides are of the unnatural L-configuration are much less known, and their use in therapy of neoplastic and viral diseases is unknown.

In the synthesis of DNA-related oligomers, types of nucleoside dimers are synthesized as part of the overall process. These dimers usually include bases from naturally occurring DNA or RNA sequences. There is much known in the art about nucleoside monophosphate dimers. Many of these compounds have been synthesized and are available commercially. However, these dimers are made from nucleosides containing a sugar moiety in D-configuration.

Reese, C. B., Tetrahedron 34 (1978) 3143 describes the synthesis of fully-protected dinucleoside monophosphates by means of the phosphotriester approach.

Littauer, U. Z., and Soreg, H. (1982) in *The Enzymes,* Vol. XV, Academic Press, NY, p. 517 is a standard reference which describes the enzymatic synthesis of dinucleotides.

Heikkilö, J., Stridh, S., Öberg, B. and Chattopodhyaya, J., Acta Chem. Scand. B 39 (1985) 657–669, provides an example of the methodology used in the synthesis of a variety of ApG nucleoside phosphate dimers. Included are references and methods for synthesis of 3'→5' phosphates and 2'→5' phosphates by solution phase chemistry.

Gait, M., "Oligonucleotide Synthesis", IRL Press, Ltd., Oxford, England, 1984, is a general reference and a useful overview for oligonucleotide synthesis. The methods are applicable to synthesis of dimers, both by solution phase and solid phase methods. Both phosphitetriester and phosphotriester methods of coupling nucleosides are described. The solid phase method is useful for synthesizing dimers.

Gulyawa, V. and Holy, A., Coll. Czec. Chem. Commun. 44613 (1979), describe the enzymatic synthesis of a series of dimers by reaction of 2', −3' cyclic phosphate donors with ribonucleoside acceptors. The reaction was catalyzed by non-specific RNases. The donors are phosphorylated in the 5'-position, yielding the following compounds: donor nucleoside-(3'→5') acceptor nucleoside. Dimers were made with acceptors, β-L-cytidine, β-L-adenosine, and 9(α-L-lyxofuranosyl) adenine. Also, a large number of dimers with D-nucleosides in the acceptor 5'-position were made.

Holy, A., Sorm, F., Collect. Czech. Chem. Commun., 34, 3383 (1969), describe an enzymatic synthesis of β-D-guanylyl-(3'→5')-β-L-adenosine and β-D-guanylyl-(3'→5')-β-L-cytidine.

Schirmeister, H. and Pfleiderer, W., Helv. Chim. Acta 77, 10 (1994), describe trimer synthesis and intermediate dimers, all from β-D-nucleosides. They used the phosphoramidite method which gave good yields.

Thus, dimers with L-deoxyribofuranosyl moieties in any position are new, as are dimers with L-ribofuranosyl moieties bonded to the 3'-position of the phosphate internucleotide bond.

Modified nucleoside analogues represent an important class of compounds in the available arsenal of antineoplastic and antiviral drugs. The anticancer agents 5-fluorodeoxyuridine (floxuridine), cytarabine and deoxycoformycin and the antiviral drugs 3'azidodeoxythymidine (AZT), dideoxycytidine (ddC), dideoxyinosine (ddI), acyclovir, 5-iododeoxyuridine (idoxuridine) fludarabine phosphate and vidarabine (adenine arabinoside/ara A) are representative of this class of monomeric nucleoside-derived compounds which are used therapeutically.

More recently, "antisense" oligonucleotide analogues with modified bases and/or phosphodiester backbones have been actively pursued as antiviral and antitumor agents. While no clinically approved drug has yet emerged from this class of compounds, it remains a very active field of research. Recently, antipodal L-sugar-based nucleosides also have found application as potent antiviral agents because they can inhibit viral enzymes without affecting mammalian enzymes, resulting in agents that have selective antiviral activity without concomitant mammalian cytotoxicity.

Most naturally occurring nucleosides have the D-configuration in the sugar moiety. While the chemical properties of L-nucleosides are similar to those of their β-D-enantiomers, they exhibit very different biological profiles in mammalian cells and do not interfere with the transport of normal D-nucleosides For example, β-L-uridine is not phosphorylated at the 5'-position by human prostate phosphotransferase, which readily phosphorylates the enantiomeric β-D-uridine. Apparently, L-nucleosides are not substrates for normal human cell kinases, but they may be phosphorylated by viral and cancer cell enzymes, allowing their use for the design of selective antiviral and anticancer drugs.

Oligonucleotides based on L-nucleosides have been studied previously. Octamers derived from α- and β-L-thymidine were found resistant to fungal nucleases and calf spleen phosphodiesterase, which readily degrades the corresponding β-D-oligonucleotide. Fujimory, et al., S. Fujimory, K. Shudo, Y. Hashimoto, J. Am. Chem. Soc., 112, 7436, have shown that enantiomeric poly-α-DNA recognizes complementary RNA but not complementary DNA. This principle has been used in the design of nuclease-resistant antisense oligonucleotides for potential therapeutic applications.

Thus, L-nucleoside-based compounds have potential as drugs against *Plasmodium falciparum* infections. While L-sugar-derived nucleosides and their oligonucleotides have been widely evaluated for such activities, little is known regarding the biological activities of shorter oligomers such as dimers obtained by L-nucleoside substitution.

This invention comprises novel L-nucleoside-derived antimalarial agents. Novel L-nucleoside-derived dinucleoside monophosphates, based on L-α-5-fluoro-2'-deoxyuridine showed a remarkably high potency activity profile in in vitro assays, with indications of unique mechanisms of action, including inhibition of telomerase. Therefore, the L-nucleosides can serve as building blocks for new drugs with the special advantage of low toxicity.

SUMMARY OF THE INVENTION

A further embodiment of the present invention is the administration of a therapeutically effective amount of the compounds of the present invention for the treatment of *Plasmodium falciparum* infection.

Other and further objects, features and advantages will be apparent from the following description of the present preferred embodiments of the invention given for the purposes of disclosure when taken in conjunction with the accompanying drawings.

Certain features of the invention may be exaggerated in scale or shown in schematic form in accordance with the customary practices in the biochemical arts.

DETAILED DESCRIPTION OF THE PREFERRED EMBODIMENTS

It is readily apparent to one skilled in the art that various substitutions and modifications may be made to the invention disclosed in this Application without departing from the scope and spirit of the invention.

Figure 1:
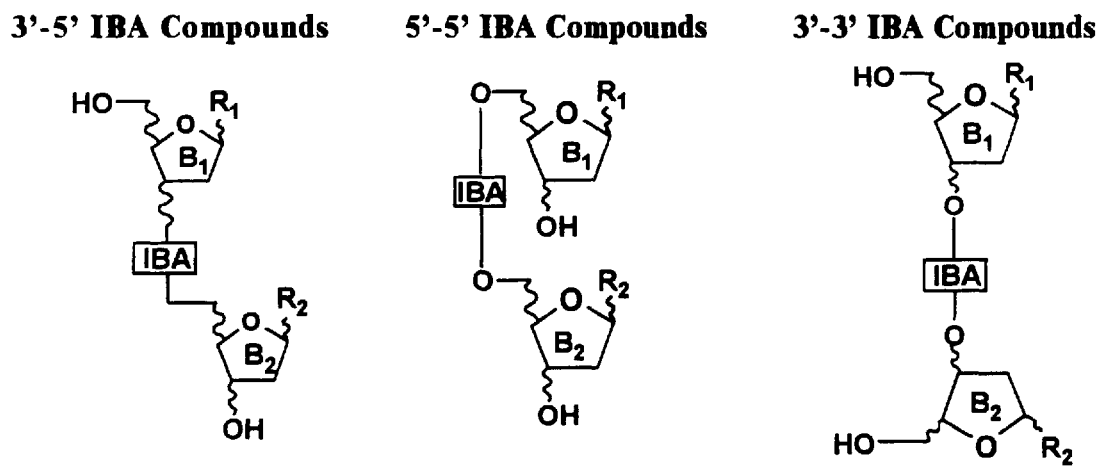
FIG. 1 is a schematic representation of examples of the dinucleotide dimers of the present invention.
Figure 1:
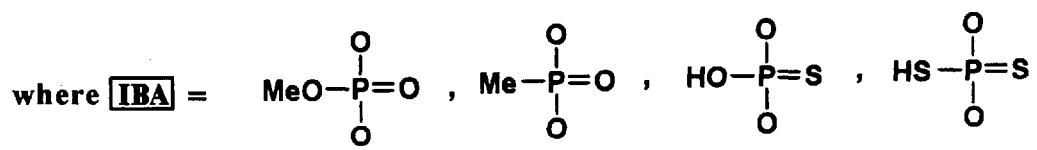
Figure 1:
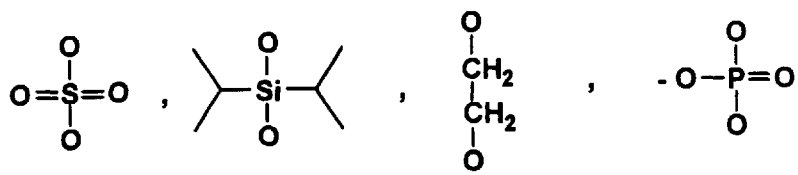
Figure 2:
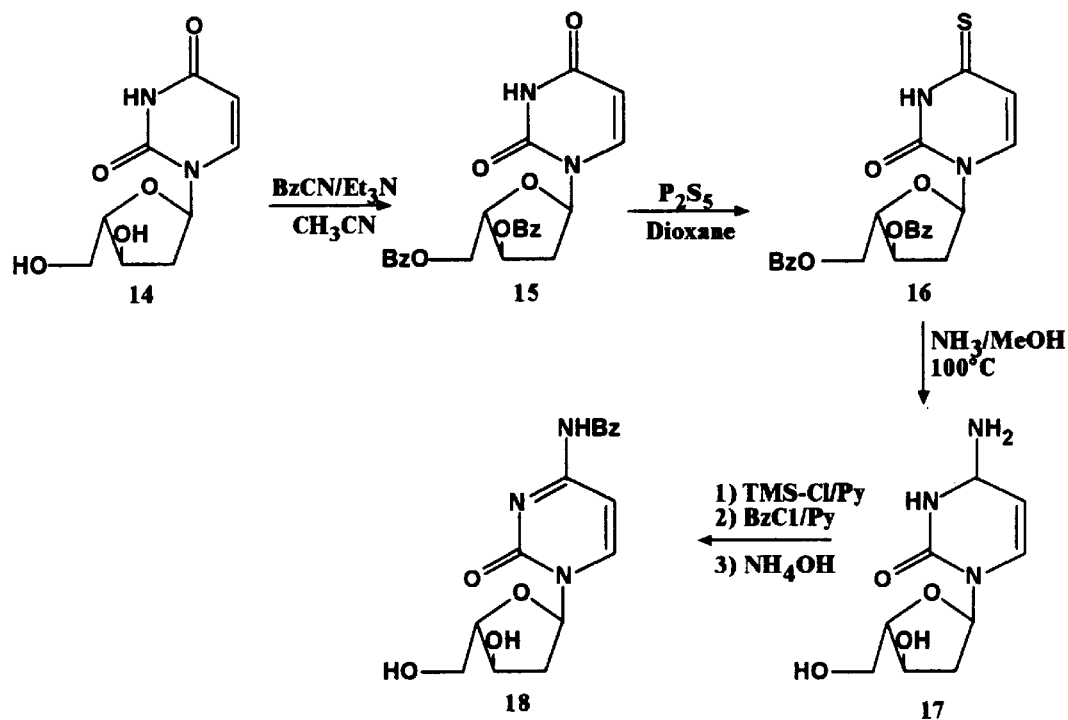
FIGS. 2–14 are schematic representations of examples of the synthesis schemes followed in the present invention.
Figure 3:
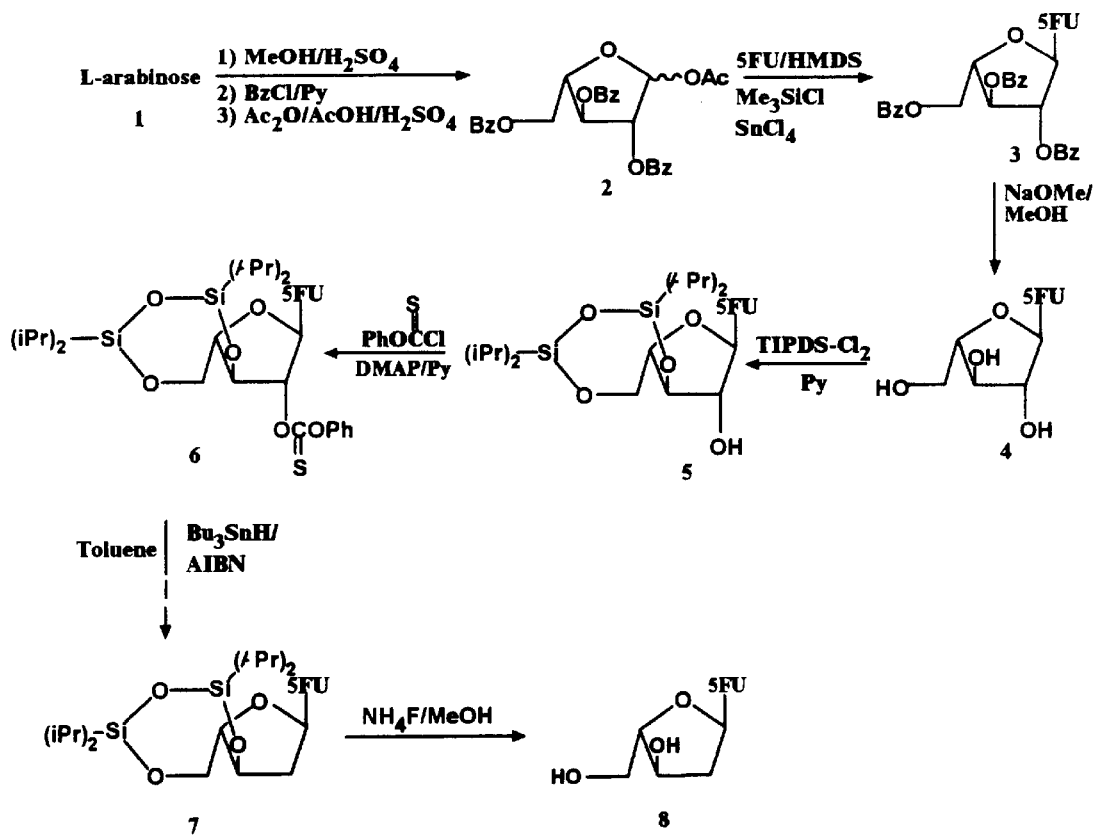
Figure 4:
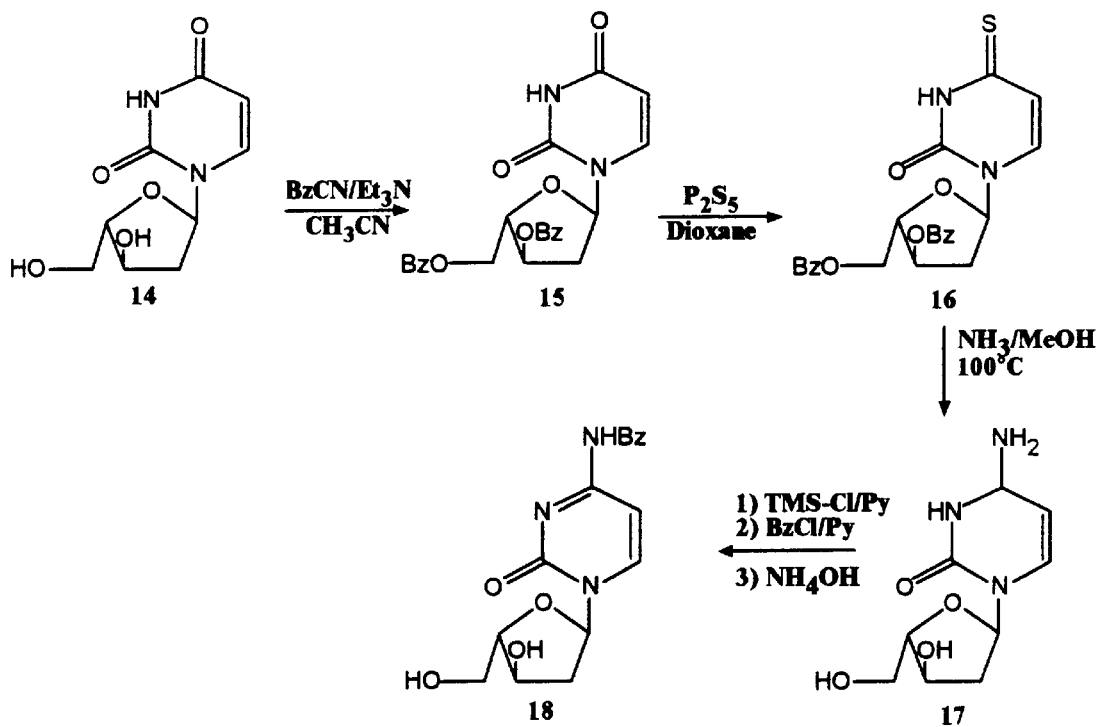
Figure 5:
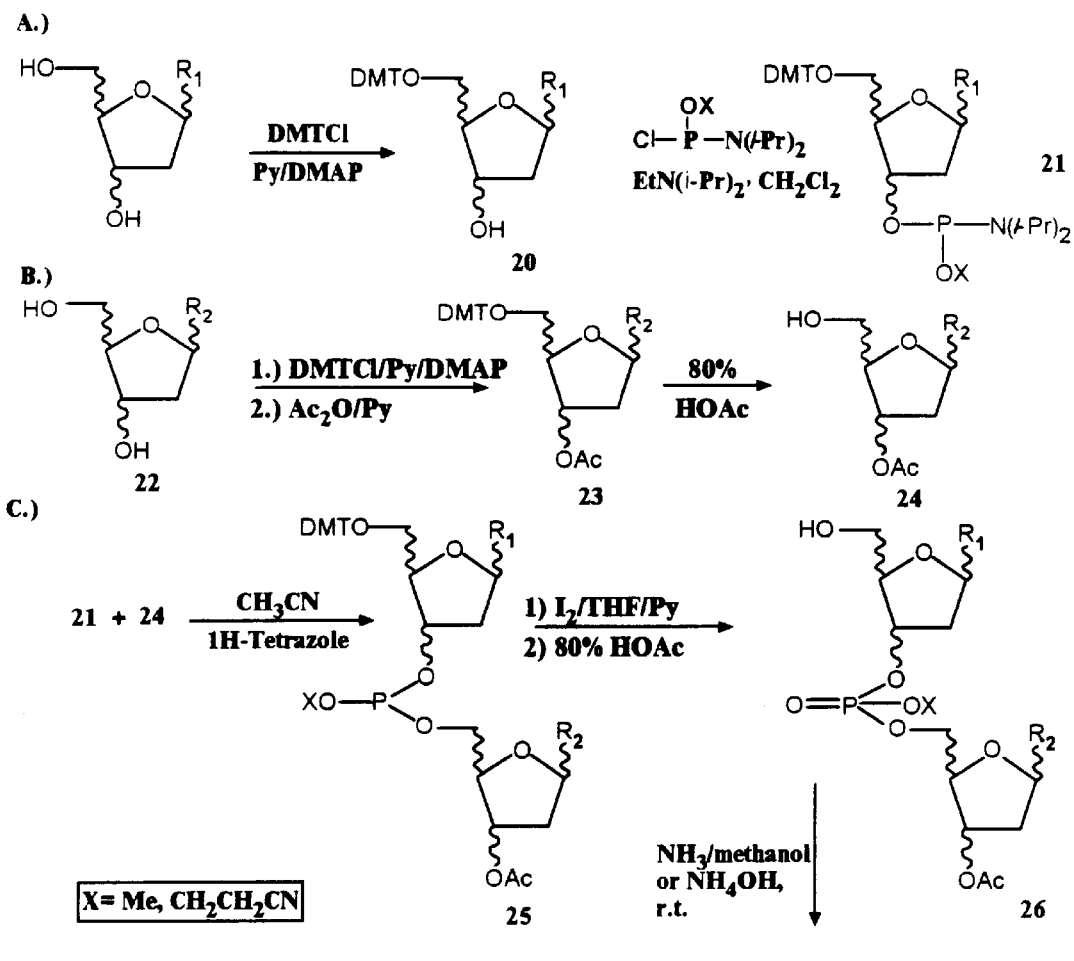

The term "dimers" as used herein is defined by the structures shown in FIG. 1. These compounds are L-nucleoside-derived dinucleoside monophosphates. The $B_1$ and $B_2$ units will consist of either a β-D, a β-L or an α-L nucleoside and at least one of $B_1$ or $B_2$ will be β-L or α-L. $R_1$ and $R_2$ will be the pyrimidine bases cytosine, thymine, uracil, or 5-fluorouridine (5-FUdR) other 5-halo compounds, or the purine bases, adenosine, guanosine or inosine. As can be seen in FIG. 1, the dimers can be bound by various linkages. Permissible linkages include 5'→3', 3'→5', 3'→3', 5'→5', 2'→3', 3'→2', 2'→2', 2'→5', 5'→2', or any other stereochemically permissible linkage. The sugar part of the nucleoside may be fully oxygenated, or it may be in the deoxy or dideoxy form.

Specific antidisease compounds which are useful in the present invention include 3'-O-(α-L-5-fluoro-2'-deoxyuridinyl)-β-D-5-fluoro-2'-deoxyuridine, (L-102), 3'-O-(β-D-5-fluoro-2'-deoxyuridinyl)-α-L-5-fluoro-2'-deoxyuridine, (L-103), 3'-O-(β-D-5-fluoro-2'-deoxyuridinyl)-α-L-2'-deoxyuridine, (L-107), 3'-O-(α-L-5-fluoro-2'-deoxyuridinyl)-α-L-5-fluoro-2'-deoxyuridine, (L-108), 3'-O-(β-L-5-fluoro-2'-deoxyuridinyl)-β-L-5-fluoro-2'-deoxyuridine, (L-109), 3'-O-(β-D-5-fluoro-2'-deoxyuridinyl)-β-L-5-fluoro-2'-deoxyuridine, (L-110), 3'-O-(β-D-5-fluoro-2'-deoxyuridinyl)-α-L-2'-deoxycytidine, (L-111), 3'-O-(β-D-5-fluoro-2'-deoxyuridinyl)-2'-deoxy-β-L-cytidine(L-113), 3'-O-(2'-deoxy-β-L-cytidinyl)-β-D-5-fluoro-2'-deoxyuridine (L-114), 3'-O-(2'-deoxy-α-L-cytidinyl)-β-D-5-fluoro-2'-deoxyuridine(L-115), 3'-O-(β-D-5-fluoro-2'-deoxyuridinyl)-β-L-2'-deoxyuridine(L-117), 3'-O-(β-L-5-fluoro-2'-deoxyuridinyl)-α-L-5-fluoro-2'-deoxyuridine(L-119), 3'-O-(β-D-5-fluoro-2'-deoxyuridinyl)-α-L-5-fluoro-2'-deoxyuridine(3', 3')(L-122), 3'-O-(3-deoxy-β-D-adenosinyl)-β-L-2'-deoxyuridine(L-150), 3'-O-(3'-deoxy-β-D-adenosinyl)-β-L-2'-deoxyadenosine(L-151), 3'O-(3'-deoxy-β-D-adenosinyl)-α-L-2'-deoxyuridine (6) (L-152), 3'-O-(3'-deoxy-β-D-adenosinyl)-β-L-2'-deoxycytidine (6) (L-153), 3'-O-(3'-deoxy-β-D-adenosinyl)-α-L-2'-deoxycytidine (L-154), 3'-O-(3'-deoxy-β-D-adenosinyl)-β-L-2'-deoxyadenosine(L-155), 3'-O-(2'-deoxy-β-D-adenosinyl)-β-L-2'-deoxyadenosine (L-210), or a therapeutically acceptable salt thereof. In the currently preferred embodiment, 3'-O-(β-D-5-fluoro-2'-deoxyuridinyl)-α-L-5-fluoro-2'-deoxyuridine, (L-103) is used.

Figure 6:
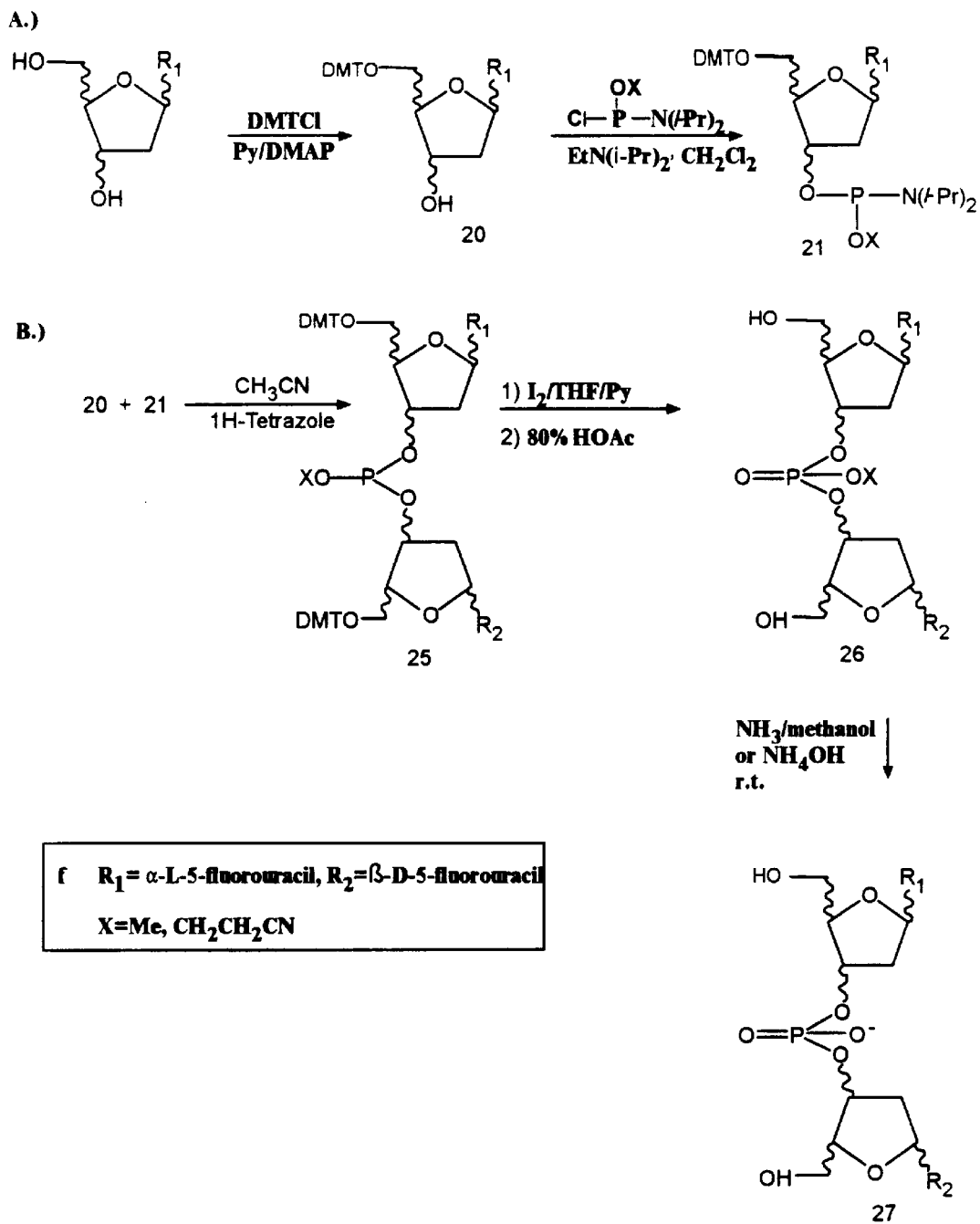

The term "internucleotide binding agent" or "IBA" means the backbone binding which links the nucleosides together. Although one skilled in the art will readily recognize a variety of other backbones are available and useful in the present invention. For example, see FIG. 6, where methoxy phosphotriesters, methylphosphonates, phosphorodithioates, phosphorothioates, silyl ethers, sulphonates and ethylenedioxy ethers are shown. Although shown schematically 3'-5' the IBA's can be used to link the sugars 5'→3', 3'→5', 3'→3', 5'→5', 2'→3', 3'→2', 2'→2', 2'→5', 5'→2', or any other stereochemically permissible linkages. The sugars may be fully oxygenated, or may be in the deoxy or dideoxy form as permitted. In the preferred embodiment, the IBA of the compounds is either phosphodiester or phosphorothioate. The term "antidisease" as used herein refers to any of the activities of the compounds of the present invention to affect the growth or progression of disease caused by *Plasmodium falciparum*.

A compound or composition is said to be "pharmacologically acceptable" if its administration can be tolerated by a recipient mammal. Such an agent is said to be administered in a "therapeutically effective amount" if the amount administered is physiologically significant. An agent is physiologically significant if its presence results in technical change in the physiology of a recipient mammal. For example, in the treatment of *Plasmodium falciparum*, a compound which inhibits the parasite's growth or decreases the number of parasites would be therapeutically effective.

Dosage and Formulation

The antidisease compounds (active ingredients) of this invention can be formulated and administered to inhibit *Plasmodium falciparum* by any means that produces contact of the active ingredient with the agent's site of action in the body of a mammal. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

Several dosages are given as examples, actual doses may be as low as 10–50% of the dosages cited herein.

The dosage administered will be a therapeutically effective amount of active ingredient and will, of course, vary depending upon known factors such as the pharmacodynamic characteristics of the particular active ingredient and its mode and route of administration; age, sex, health and weight of the recipient; nature and extent of symptoms; kind of concurrent treatment, frequency of treatment and the effect desired. Usually a daily dosage (therapeutic effective amount) of active ingredient can be about 5 to 400 milligrams per kilogram of body weight. Ordinarily, 10 to 200, and preferably 10 to 50, milligrams per kilogram per day given in divided doses 2 to 4 times a day or in sustained release form is effective to obtain desired results.

Dosage forms (compositions) suitable for internal administration contain from about 1.0 to about 500 milligrams of active ingredient per unit. In these pharmaceutical compositions, the active ingredient will ordinarily be present in an amount of about 0.05–95% by weight based on the total weight of the composition.

The active ingredient can be administered orally in solid dosage forms such as capsules, tablets and powders, or in liquid dosage forms such as elixirs, syrups, emulsions and suspensions. The active ingredient can also be formulated for administration parenterally by injection, rapid infusion, nasopharyngeal absorption or dermoabsorption. The agent may be administered intramuscularly, intravenously, or as a suppository.

Gelatin capsules contain the active ingredient and powdered carriers such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents and, if necessary, buffer substances. Antioxidizing agents such as sodium bisulfate, sodium sulfite or ascorbic acid, either alone or combined, are suitable stabilizing agents.

Also used are citric acid and its salts and sodium EDTA. In addition, parenteral solutions can contain preservatives such as benzalkonium chloride, methyl- or propyl-paraben and chlorobutanol. Suitable pharmaceutical carriers are described in *Remington's Pharmaceutical Sciences,* a standard reference text in this field.

Additionally, standard pharmaceutical methods can be employed to control the duration of action. These are well known in the art and include control release preparations and can include appropriate macromolecules, for example polymers, polyesters, polyaminoacids, polyvinyl, pyrolidone, ethylenevinylacetate, methyl cellulose, carboxymethyl cellulose or protamine sulfate. The concentration of macromolecules as well as the methods of incorporation can be adjusted in order to control release. Additionally, the agent can be incorporated into particles of polymeric materials such as polyesters, polyaminoacids, hydrogels, poly (lactic acid) or ethylenevinylacetate copolymers. In addition to being incorporated, these agents can also be used to trap the compound in microcapsules.

Useful pharmaceutical dosage forms for administration of the compounds of this invention can be illustrated as follows.

Capsules: Capsules are prepared by filling standard two-piece hard gelatin capsulates each with 100 milligram of powdered active ingredient, 175 milligrams of lactose, 24 milligrams of talc and 6 milligrams magnesium stearate.

Soft Gelatin Capsules: A mixture of active ingredient in soybean oil is prepared and injected by means of a positive displacement pump into gelatin to form soft gelatin capsules containing 100 milligrams of the active ingredient. The capsules are then washed and dried.

Tablets: Tablets are prepared by conventional procedures so that the dosage unit is 100 milligrams of active ingredient. 0.2 milligrams of colloidal silicon dioxide, 5 milligrams of magnesium stearate, 275 milligrams of microcrystalline cellulose, 11 milligrams of cornstarch and 98.8 milligrams of lactose. Appropriate coatings may be applied to increase palatability or to delay absorption.

Injectable: A parenteral composition suitable for administration by injection is prepared by stirring 1.5% by weight of active ingredients in 10% by volume propylene glycol and water. The solution is made isotonic with sodium chloride and sterilized.

Suspension: An aqueous suspension is prepared for oral administration so that each 5 millimeters contain 100 milligrams of finely divided active ingredient, 200 milligrams of sodium carboxymethyl cellulose, 5 milligrams of sodium benzoate, 1.0 grams of sorbitol solution U.S.P. and 0.025 millimeters of vanillin.

Summary of Compounds Synthesized

The following examples are offered by way of illustration and are not intended to limit the invention in any manner. The nucleosides and dimers may incorporate any stereochemcially permissible linkage and may include various oxygentaed, deoxy, and dideoxy forms of the sugar rings. The synthetic nucleosides and dimers described in the examples can include any of the substitutions discussed earlier. The backbone and base modifying groups can be added. Various substitutions will enhance the affinity, the chemical stability and the cellular uptake properties of the specific dimers treatments.

EXAMPLE 1

Synthesis of 2'-deoxy-α-L-5-flourouridine

While β-D-5-fluoro-deoxyuridine is commercially available, the α-L-isomer 2'-deoxy-α-L-5-fluorouridine is not, and this component of the dimers was synthesized from L-arabinose.

1-(2',3',5'-tri-O-benzoyl-α-L-arabinofuranosyl)-5-fluorouracil (3)

To a mixture of 5-fluorouracil (4.01 g, 30.87 mmol) and compound 2 (15.57 g, 30.87 mmol) in anhydrous MeCN were successively added HMDS (5.20 ml, 24.69 mmol), ClSiMe$_3$ (3.10 ml, 24.69 mmol), and SnCl$_4$ (4.30 ml, 37.04 mmol). The resulting clear solution was refluxed for one hour. Then the solvent was evaporated and the residue was dissolved in EtOAc (750 ml), washed with H$_2$O, and saturated NaHCO$_3$ solution. The EtOAc layer was dried over sodium sulfate, filtered and evaporated to give the crude product. This crude product was purified on a silica gel column using 40–50% EtOAc/petroleum ether to give pure 3 (11.7 g, 66.0% yield) as a white foam.

NMR: (CDCl$_3$) δ=4.65 (dd, 1H), 4.78 (dd, 1H), 4.97 (dd, 1H, 5.75–5.88 (2 t, 2H), 6.27 (d, 1H), 7.36–7.62 and 8.00–8.10 (m, 5H), 8.94 (d, 1H).

1-α-L-arabinofuranosyl-5-fluorouracil (4)

To a solution of compound 3 (11.7 g, 20.37 mmol) in MeOH (300 ml), NaOMe (4.2 ml of a methanolic 25% w/v solution) was added and the solution was stirred until the reaction was complete. The solvent was then evaporated and the residue was dissolved in H$_2$O (200 ml), washed with ether and neutralized with Dowex 50 ion exchange resin. After filtration of the resin, the aqueous solution was evaporated to give compound 4(4.92 g, 92% yield) as a white foam.

NMR: (DMSO-d$_6$) δ=3.48 (m, 2H), 3.93–4.00 (2 t, 2H), 4.16 (q, 1 H), 5.69 (dd, 1H), 8.03 (d, 1H).

1[3',5'-O-(1,1,3,3-tetraisopropyldisiloxane-1,3-diyl)-α-L-arabinofuranosyl]-5-fluorouracil (5)

To a stirred suspension of 4 (6.43 g, 24.52 mmol) in pyridine (200 ml) was added 1,3-dichloro-1,1,3,3-tetraisopropyldisiloxane (10.3 ml, 29.43 mmol). This was stirred at room temperature until the reaction was complete (5 hours). The solvent was evaporated to a residue which was dissolved in EtOAC and washed successively with H$_2$O, 5% HCl, H$_2$O, saturated NaHCO$_3$, and brine. After drying the EtOAc portion over Na$_2$SO$_4$, the solution was filtered and evaporated to give the crude product 5 which was used in the next step without further purification.

1-[2'-O-phenoxythiocarbonyl-3',5'-O-(1,1,3,3-tetraisopropyldisiloxane-1,3-diyl)-α-L-arabinofuraosyl]-5-fluorouracil (6)

To a solution of 5 (24.52 mmol) in anhydrous MeCN (300 ml) were added 4-dimethylaminopyridine (DMAP) (5.80 g, 47.58 mmol), and phenylchlorothionoformate (3.85 ml, 26.98 mmol). The solution was stirred at room temperature for 24 hours. Then, the solvent was evaporated to a residue which was dissolved in EtOAc and washed successively with H$_2$O, 5% HCl, H$_2$O, saturated NaHCO$_3$, and brine. After drying the EtOAc portion over Na$_2$SO$_4$, the solution was filtered and evaporated to an oil. The oil was purified on a silica gel column using 30% EtOAc/petroleum ether to produce pure 6 (8.9 g, 56.7% yield) as a yellow foam.

NMR: (CDCl$_3$) δ=4.02 (m, 2H), 4.32 (m, 1H), 4.76 (dd, 1H), 6.10 (dd, 1H), 6.18 (dd, 1H), 7.07–7.48 (m, 6H), 8.41 (br s, 1H).

3',5'-O-(1,1,3,3-tetraisopropyldisiloxane-1,3-diyl)-α-L-2'-deoxy-5-fluorouridine (7)

To a solution of 6 (8.92 g, 13.91 mmol), in dry toluene (300 ml) was added AIBN (0.46 g, 2.78 mmol) followed by Bu$_3$SnH (20.0 ml, 69.35 mmol). The solution was deoxygenated with argon and heated at 75° C. for four hours. The solvent was then evaporated and the residue was purified on a silica gel column using 30% EtOAc/petroleum ether to give pure 7 (5.44 g, 80% yield) as a white foam.

NMR: (CDCl$_3$) δ=2.16 (m, 1H), 2.84 (m, 1H), 3.8 Cm, 1H), 4.07 (m, 1H), 4.60 (m, 1H), 6.19 (ddd, 1H), 7.92 (m, 1H).

2'-deoxy-α-L-5-fluorouridine (8)

A solution of compound 7 (5.44 g, 11.13 mmol) and NH$_4$F (4.12 g, 111.3 mmol) in MeOH was stirred in an oil bath at 60° C. for 3 hours. Silica gel (3 g) was added and the mixture was evaporated to a dry powder. This powder was added to a silica column and eluted with 10–15% MeOH/CHCl$_3$ to produce pure 8 (2.4 g, 87.6% yield) as a white foam.

NMR: (DMSO-d$_6$) δ=1.90 (m,1H), 2.55 (m, 1H), 3.33 (m, 2H), 4.19 (m, 2H), 4.86(br s, 1H), 5.43 (br s, 1H), 6.10 (dd, 1H), 8.15 (d, 1H), 11.78(br s, 1H).

EXAMPLE 2

Synthesis of 2'-deoxy-α-L-uridine 1-(2',3',5'-tri-O-benzoyl-α-L-arabinofuranosyl) uracil (9)

To a mixture of uracil (1.17 g, 10.49 mmol) and compound 2 (5 g) in anhydrous MeCN (100 ml) were successively added HMDS (1.77 ml, 8.39 mmol), ClSiMe$_3$ (1.06 ml, 8.39 mmol), and SnCl$_4$ (1.47 ml, 12.58 mmol). The resulting clear solution was refluxed for one hour. Then the solvent was evaporated and the residue was dissolved in EtOAc (200 ml), washed with H$_2$O, and saturated NaHCO$_3$ solution. The EtOAc layer was dried over sodium sulfate, filtered and evaporated to give the crude product, which was purified on a silica gel column using 40–50% EtOAc/petroleum ether to give pure 9 (3.66 g, 62.7% yield) as a white foam.

NMR: (CDCl$_3$) δ=4.70 (m, 1H), 5.77 (5, 1H), 5.80 (dd, 1H), 5.94 (t, 1H) 6.20 (d, 1H), 7.40–8.10 (m, 16H), 8.58 (br s, 1H).

1-α-L-arabinofuranosyl-uracil (10)

To a solution of compound 8 (17.83 g, 32.03 mmol) in MeOH (400 ml), NaOMe (5.0 ml of a methanolic 25% w/v solution) was added and the solution was stirred until the reaction was complete. The solvent was then evaporated and the residue was dissolved in H$_2$O (250 ml), washed with ether and neutralized with Dowex 50 ion exchange resin. After filtration of the resin, the aqueous solution was evaporated to give compound 10 (7.4 g, 94.6% yield) as a white foam. This was used in the next step without further purification.

1-[3',5'-o-(1,1,3,3-tetraisopropyldisiloxane-1,3-diyl)-α-L-arabinofuranosyl]-uracil (11)

To a stirred suspension of 10 (7.4 g, 30.3 mmol) in pyridine was added 1.3-dichloro-1,1,3,3-tetraisopropyldisiloxane (12.74 ml, 36.36 mmol). This was stirred at room temperature until the reaction was complete (5 hours). The solvent was evaporated to a residue which was dissolved in EtOAC (500 ml) and washed successively with H$_2$O, 5% HCl, H$_2$O, saturated NaHCO$_3$, and brine. After drying the EtOAc portion over Na$_2$SO$_4$, the solution was filtered and evaporated to give the crude product 11 which was used in the next step without further purification.

1-[2'-o-phenoxythiocarbonyl-3',5'-o-( 1,1,3,3-tetraisopropyldisiloxane-1,3-diyl)-α-L-arabinofuranosyl]-uracil (12)

To a solution of 11 (30.3 mmol) in anhydrous MeCN were added 4-dimethylaminopyridine (DMAP) (7.2 g, 58.78 mmol), and phenylchlorothionoformate (4.7 ml, 33.33 mmol). The solution was stirred at room temperature for 24 hours. Then, the solvent was evaporated to a residue which was dissolved in EtOAc (750 ml) and washed successively with H$_2$O, 5% HCl, H$_2$O, saturated NaHCO$_3$, and brine. After drying the EtOAc portion over Na$_2$SO$_4$, the solution was filtered and evaporated to an oil. The oil was purified on a silica gel column using 30% EtOAc/petroleum ether to produce pure 12 (13.14 g, 74.5% yield) as a white foam.

NMR: (CDCl$_3$) δ=4.04 (m, 2H), 4.38 (m, 1H), 4.73 (dd, $_1$H), 5.79 (dd, 1H), 5.93 (d, 1H), 6.31 (dd, 1H), 7.08–7.33 (m, 6H), 9.2 (br s, 1H).

3',5'-o-(1,1,3,3-tetraisopropyldisiloxane-1,3-diyl)-α-L-2'-deoxyuridine (13)

To a mixture of 12 (13.14 g, 21.09 mmol), in dry toluene (300 ml) was added AIBN (0.69 g, 4.2 mmol) followed by Bu$_3$SnH (28.4 ml, 105.4 mmol). The solution was deoxygenated with argon and heated at 75° C. for four hours. The solvent was then evaporated and the residue was purified on a silica gel column using 30% EtOAc/petroleum ether to give pure 13 (9.29 g, 88.4% yield) as a white foam.

NMR: (CDCl$_3$) δ=2.15 (2 t, 1H), 2.81 (m, 1H), 3.82 (dd,1H), 4.05 (m, 2H), 4.56 (q, 1H), 5.75 (dd, 1H), 6.16 (t, 1H), 7.69 (d, 1H), 9.38 (br s, 1H).

2'-deoxy-α-L-uridine (14)

A mixture of compound 13 (9.2 g, 18.63 mmol) and NH$_4$F (6.9 g, 186.3 mmol) in MeOH (200 ml) was stirred in an oil bath at 60° C. for 3 hours. Silica gel (5 g.) was added and the mixture was evaporated to a dry powder. This powder was added to a silica column and eluted with 10–15% MeOH/CHCl$_3$ to produce pure 14 (3.70 g, 83% yield) as a white foam.

NMR: (DMSO-d$_6$) δ=1.87 (m, 1H), 2.56 (m, 1H), 3.41 (m, 2H), 4.15 (m, 1H), 4.22 (m, 1H), 4.44 (t, 1H), 4.92 (t, 1H), 5.38 (d, 1H), 5.62 (d, 1H), 6.09 (dd, 1H).

EXAMPLE 3

Synthesis of 2'-deoxy-α-L-cytidine

3',5'-di-O-benzoyl-2'-deoxy-α-L-uridine (15)

A solution of BzCN (0.61 g, 4.67 mmol) in MeCN (10 ml) was added dropwise to a suspension of compound 14 (0.43 g, 1.87 mmol) in MeCN (10 ml) followed by Et$_3$N (0.1 ml). The reaction was stirred at room temperature for three hours after which time the solvent was evaporated to dryness. The crude material was purified on a silica gel column using 50% EtOAc/petroleum ether to give pure 15 (0.57 g, 70% yield) as yellow foam.

NMR: (CDCl$_3$) δ=2.55 (d, 1H), 2.96 (dt, 1H), 4.56 (m, 2H), 4.86 (t, 1H), 5.61 (d, 1H), 5.73 (dd, 1H), 6.31 (dd, 1H), 7.40–7.63 (m, 7H), 7.87–8.06 (m, 4H), 8.82 (br s, 1H).

3',5'-di-O-benzoyl-2'-deoxy-4-thio-α-L-uridine (16)

A boiling solution of compound 15 (0.54 g, 1.25 mmol) in anhydrous dioxane was treated with P$_2$S$_5$ (0.61 g, 2.75 mmol) and the mixture was refluxed under a nitrogen atmosphere for one hour. Remaining solids were filtered from the hot solution and washed on the filter with additional dioxane. The filtrate was evaporated to dryness and the crude product was purified on a silica gel column using 30% EtOAc/petroleum ether to give pure 16 (0.42 g, 74% yield) as a yellow oil.

NMR: (CDCl$_3$) δ=2.59 (d, 1H), 2.93 (dt, 1H), 4.58 (m, 2H), 4.89 (t, 1H), 5.63 (d, 1H), 6.26 (dd, 1H), 6.41 (dd, 1H), 7.40–8.10 (m, 11H), 9.54 (br s, 1H).

2'-deoxy-α-L-cytidine (17)

Compound 16 (0.42 g, 9.28 mmol) was treated with NH$_3$/MeOH (50 ml) in a steel bomb at 100° C. for 10 hours. After cooling, the solvent was evaporated to dryness, the residue was dissolved in water (50 ml) and washed with ether (3×50 ml). The water layer was treated with charcoal, filtered through Celite and evaporated to dryness by coevaporation with EtOH. The semi-solid obtained was crystallized from EtOH/ether to give compound 17 (0.18 g, 85.7% yield).

NMR: (DMSO-d$_6$) δ=1.86 (Cd,H), 2.50 (m, 1H), 3.40 (m, 1H), 4.12 (m,1H), 4.15 (m, 1H), 4.86 (t, 1H), 5.21 (d, 1H), 5.69 (d, 1H), 6.03 (dd, 1H), 7.02 (br d, 1H), 7.74 (d, 1H).

N$^4$-benzoyl-2'-deoxy-α-L-cytidine (18)

ClSiMe$_3$ (2.3 ml, 18.05 mmol) was added dropwise over 30 minutes to a stirring suspension of compound 17 (0.82 g, 3.61 mmol) in pyridine (50 ml) chilled in an ice bath. BzCl (2.1 ml, 18.05 mmol) was then added dropwise and the reaction mixture was cooled at room temperature for two hours. The reaction mixture was again cooled in an ice bath and cold water (10 ml) was added dropwise. Fifteen minutes later, concentrated NH$_4$OH (10 ml) was added to produce a solution of ammonia of a concentration of about 2M. Thirty minutes after the addition of the ammonia solution, a solvent was evaporated, dissolved in water and washed with ether. Evaporation of this aqueous solution provided the crude product (18) which was used in the next step without further purification.

EXAMPLE 4

Synthesis of Dimers

The dimers were prepared from the monomeric materials by the general scheme shown in Scheme 2.

A. α-L, β-D 5 FUdR Dimer

5'-O-dimethoxytrityl-α-L-5-fluoro-2'-deoxyuridine (20a)

α-L-5-fluoro-2'-deoxyuridine (8) (500 mg, 2.0 mmol) was dissolved in 10 ml of dry, distilled pyridine. To this solution was added 4,4'-dimethoxytrityl chloride (813 mg, 2.4 mmol) and 4-dimethylaminopyridine (DMAP) (50 mg, 0.4 mmol). The mixture was stirred under an argon atmosphere for 16 hours. After this time, the pyridine was stripped off in vacuo. The residue was dissolved in EtOAc (50 ml). The organic layer was washed with saturated NaHCO$_3$, water and with brine. The organic layer was dried over Na$_2$SO$_4$, filtered and evaporated in vacuo to a residue which was purified on a silica gel column using 10% MeOH/CHCl$_3$. Pure fractions were pooled and evaporated to give the pure product as an off-white foam (679 mg, 86% yield). Rf=0.48 in 10% MeOH/CHCl$_3$.

NMR: (DMSO-d$_6$) δ=2.3 (dd, 1H), 2.72–2.81 (m, 1H), 3.15–3.26 (m, 2H), 3.75 (s, 6H), 4.45 (m, 2H), 6.23 (dd, 1H), 6.92 (d, 1H), 7.2–7.3 (m, 13H), 7.94 (d, 1H).

5'-O-dimethoxytrityl-α-L-5-fluoro-2'-deoxyuridine-3'-N,N-diisopropylmethoxy phosphoramidite (21a)

The 5'-O-dimethoxytrityl-α-L-5-fluoro-2'-deoxyuridine (20a, 548 mg, 1 mmol) was dissolved in anhydrous dichloromethane (20 ml). N,N-diisopropylethylamine (700 μl, 4 mmol) was added through a septum, followed by chloro-N, N-diisopropylmethoxyphosphine (290 μl, 1.5 mmol), under an argon atmosphere. The reaction was stirred for 30 minutes. The solvent was evaporated and the residue was partitioned between an 80% EtOAc/triethylamine mixture and brine. The organic layer was washed with saturated NaHCO$_3$ solution and brine. The organic residue was evaporated to dryness and the residue was purified on a silica gel column using a mixture of dichloromethane, EtOAc and triethylamine (45:45:10; Rf=0.69). The product (390 mg) was isolated as a yellow foam and it was used in the next step without further purification.

3'-Acetoxy-β-D-5-fluoro-2'-deoxyuridine (24a)

β-D-5-fluoro-2'-deoxyuridine (500 mg, 2.2 mmol) was dissolved in 10 ml of dry, distilled pyridine. To this solution was added 4,4'-dimethoxytrityl chloride (813 mg, 2.4 mmole) and 4-dimethylaminopyridine (DMAP) (50 mg, 0.4 mmole). The mixture was stirred at room temperature for 16 hours. The pyridine was stripped off in vacuo. The residue was dissolved in dichloromethane (50 ml). The organic layer was washed with 0.3 N HCl, brine, saturated NaHCO$_3$, and again with brine. The organic layer was dried over Na$_2$SO$_4$, filtered and evaporated in vacuo to a residue which was purified on a silica gel column, eluting with 10% MeOH/CHCl$_3$. Pure fractions were pooled and evaporated to give the pure product as an off-white foam (685 mg, 86% yield). This material was dissolved in pyridine (12 ml) and treated with acetic anhydride (2.5 ml) for 3 hours at room temperature. The solvent was evaporated, and the residue was dissolved in ethyl acetate. The ethyl acetate was washed as described above, dried over sodium sulfate and evaporated. The residue was then treated with 80% acetic acid (10 ml) for 2.5 hours at room temperature. The solvent was evaporated in vacuo and the residue was chromatographed on silica gel, eluting with 10% MeOH/CHCl$_3$ to give pure 24a as a white foam, yield 422 mg.

NMR: (DMSO-d$_6$) δ=1.95 (s, 3H), 2.08–2.24 (m, 2H), 3.65–3.9 (m, 2H), 4.45 (m, 1H), 4.72 (m, 1H), 6.24 (dd, 1H), 8.24 (d, 1H).

5'-O-dimethoxytrityl-3'-[O-(3'-O-acetyl)-β-D-5-fluoro-2'-deoxyuridinyl]-α-L-5-fluoro-2'-deoxyuridine (25a)

The 3'-O-acetyl-β-D-5-fluoro-2'-deoxyuridine (188 mg, 0.65 mmol) was dissolved in dry acetonitrile (5 ml). Sublimed 1H-tetrazole (80 mg) was added and the mixture was stirred under an argon atmosphere for 15 minutes. The solution of 21a (380 mg, 0.54 mmol), dissolved in 5 ml of dry acetonitrile was added via syringe to the reaction solution over 5 minutes. The mixture was allowed to stir at room temperature for three hours. The acetonitrile was evaporated in vacuo to a residue. This residue was triturated with a 70% EtOAc/ether mixture. The undissolved tetrazole was filtered off and the filtrate was evaporated to give a dry yellow foam (468 mg). This foam was used in the next step without further purification.

(3'-acetoxy-β-D-5-fluoro-2'-deoxyuridinyl)-α-L-5-fluoro-2'-deoxyuridine methyl phosphonate ester (26a)

The dimer, 25a (504 mg), was dissolved in 8 ml of THF and 2 ml of pyridine containing 0.2 ml of water. Iodine crystals (26 mg) were added and the contents of the loosely stoppered flask were allowed to stir for 2.1 hours. Excess iodine was discharged by the addition of a few drops of saturated sodium thiosulfate. The reaction mixture was then evaporated to dryness. The crude product was dissolved in EtOAc washed with saturated NaHCO$_3$ solution and brine. The organic layer was dried over Na$_2$SO$_4$, filtered and evaporated in vacuo. The residue (530 mg) was dissolved in 10 ml of 80% acetic acid/water solution and was stirred until the reaction was completed. The solvent was evaporated and the residue was purified on a silica gel column, using 20% MeOH/CHCl$_3$. Fractions containing one spot by TLC (10% MeOH/CHCl$_3$ Rf=0.35) were pooled and evaporated to give the pure product (316 mg).

NMR: (CD$_3$OD) δ=2.08 (s, 3H), 2.25–2.45 (m, 3H), 2.65–2.72 (m,1H), 3.60 (m, 2H), 3.80 (2d, 3H), 4.18 (m, 1H), 4.28 (m, 1H), 4.35 (dd, 1H), 4.62 (dd, 1H), 5.05 (dd, 1H), 5.23 (m, 1H), 6.13 (m, 1H), 6.18 (m, 1H), 7.85 (m, 2H).

P$^{31}$ NMR: (CD$_3$OD) δ=0.77 (s), 1.16 (s).

3'-O-(β-D-5-fluoro-2'-deoxyuridinyl)-α-L-5-fluoro-2'-deoxyuridine (27a)

The O-protected dimer, 26a (280 mg) was treated with 20 ml of saturated methanolic ammonia at room temperature until the reaction was completed at room temperature. The solvent was stripped off in vacuo and the residue was purified on DEAE cellulose ion exchange column using gradient of NH$_4$CO$_3$ buffer from 0.02–0.2 M. Pure fractions were evaporated at 40° C. in high vacuo to dryness to give the pure product (162 mg).

NMR: (D$_2$O) δ=2.2–2.4 (m, 3H), 2.65–2.71 (m, 1H), 3.65 (m, 2H), 4.01 (m, 1H), 4.11 (t, 1H), 4.45 (m, 1H), 4.65 (t, 1H), 6.14 (d, 1H), 6.24 (td, 1H), 8.06 (d, 1H), 8.02 (d, 1H).

$^{31}$P NMR: (D$_2$O) δ=0.04 (s).

B. β-D, α-L 5FUdR Dimer

5'-O-dimethoxytrityl-3'-[O-(3'-O-acetyl)-α-L-5-fluoro-2'-deoxyuridinyl]-β-D-5-fluoro-2'-deoxyuridine (25b)

The 3'-O-acetyl-α-L-5-fluoro-2'-deoxyuridine, 24b (188 mg, 0.65 mmol) was dissolved in dry acetonitrile (5 ml). Sublimed 1H-tetrazole (80 mg) was added and the mixture was stirred under an argon atmosphere for 15 minutes. The solution of 21b (380 mg, 0.54 mmol), dissolved in 5 ml of dry acetonitrile was added via syringe to the reaction solution over 5 minutes. The mixture was allowed to stir at room temperature for three hours. The acetonitrile was evaporated in vacuo to a residue. This residue was triturated with a 70% EtOAc/ether mixture. The undissolved tetrazole was filtered off and the filtrate was evaporated to give a dry yellow foam (484 mg). This foam was used in the next step without further purification.

(3'-acetoxy-α-L-5-fluoro-2'-deoxyuridinyl)-β-D-5-fluoro-2'-deoxyuridine methyl phosphate ester (26b)

The dimer, 25b (526 mg), was dissolved in 8 ml of THF and 2 ml of pyridine containing 0.2 ml of water. Iodine crystals (26 mg) were added and the contents of the loosely stoppered flask were allowed to stir for 1 hour. Excess iodine was discharged by the addition of a few drops of saturated sodium thiosulfate. The reaction mixture was then evaporated to dryness. The crude product was dissolved in EtOAc washed with saturated NaHCO$_3$ solution and brine. The organic layer was dried over Na$_2$SO$_4$, filtered and evaporated in vacuo. The residue (578 mg) was dissolved in 10 ml of 80% acetic acid/water solution and was stirred for three hours. The solvent was evaporated and the residue was purified on a silica gel column, using 10–15% MeOH/CHCl$_3$. Fractions containing one spot by TLC (10% MeOH/CHCl$_3$ Rf-0.35) were pooled and evaporated to give the pure product (342 mg).

NMR: (DMSO-d$_6$) δ=1.98 (s, 3H), 2.2–2.4 (m, 3H), 2.62–2.71 (m, 1H), 3.5–3.8 (m, 4H), 4.02 (m, 1H), 4.42 (m, 2H), 6.10 (dd, 1H), 6.26 (dt, 1H), 8.00 (d, 1H), 8.04 (d, 1H).

3'-O-(α-L-5-fluoro-2'-deoxyuridinyl)-β-D-5-fluoro-2'-deoxyuridine (27b)

The O-protected dimer, 26b (170 mg) was treated with 20 ml of saturated methanolic ammonia at room temperature until the reaction was completed. The solvent was stripped off in vacuo and the residue was purified on DEAE cellulose ion exchange column using gradient of NH$_4$CO$_3$ buffer from 0.02–0.2 M. Pure fractions were evaporated at 40° C. in high vacuo to dryness to give the pure product (89 mg).

NMR: (D$_2$O) δ=2.2–2.4 (m, 3H), 2.65–2.71 (m, 1H), 3.54–3.85 (m, 5H), 4.05 (t, 1H), 4.42 (m, 2H), 6.06 (dd, 1H), 6.23 (dt, 1H), 8.00 (d, 1H), 8.04 (d, 1H).

C. α-L uridine, β-D 5 FUdR dimer

5'-O-(di-p-methoxytrityl)-2'-deoxy-α-L-uridine (20c)

α-L-2'-deoxyuridine (1.5 g, 6.57 mmol) was dissolved in 25 ml of dry, distilled pyridine. To this solution was added 4,4'-dimethoxytrityl chloride (2.9 g, 7.89 mmol) and 4-dimethylamino pyridine (DMAP) (160 mg, 1.31 mmol). The mixture was stirred under an argon atmosphere for 16 hours. After this time, the pyridine was stripped off in vacuo. The residue was dissolved in EtOAc (150 ml). The organic layer was washed with saturated NaHCO$_3$, water and again with brine. The organic layer was dried over Na$_2$SO$_4$, filtered and evaporated in vacuo to a residue which was purified on a silica gel column using 5% MeOH/CHCl$_3$. Pure fractions were pooled and evaporated to give the pure product as an off-white foam (2.84 g, 81% yield).

NMR: (CDCl$_3$-d$_6$) δ=2.29 (d, 1H), 2.70 (m, 2H), 3.17 (m, 2H), 3.78 (s, 6H), 4.44 (m, 2H), 5.63 (d, 1H), 6.19 (d, 1H), 6.83 (d, 4H), 7.28 (m, 9 H), 7.68 (d, 1H), 9.30 (br s, 1H).

5'-O-(dimethoxytrityl)-α-L-2'-deoxyuridine-3'-N,N-diisopropylmethoxy phosphoramidite (21c)

The 5'-O-dimethoxytrityl-α-L-2'-deoxyuridine (2.35 g, 4.43 mmol) was dissolved in anhydrous dichloromethane (50 ml). N,N-diisopropylethylamine (3.1 ml, 17.72 mmol) was added through a septum, followed by chloro-N,N-diisopropylmethoxyphosphine (1.3 ml, 6.64 mmol), under an argon atmosphere. The reaction was stirred for 30 minutes. The solvent was evaporated and the residue was partitioned between an 80% EtOAc/triethylamine mixture and brine. The organic layer was washed with saturated NaHCO$_3$ solution and brine. The organic residue was evaporated to dryness and the residue was purified on a silica gel column using a mixture of dichloromethane, EtOAc and triethylamine (40:50:10; Rf=0.69). The product was isolated quantitatively as a yellow foam and it was used in the next step without further purification.

5'-O-dimethoxytrityl-3'-[O-(3'-O-acetyl)-β-D-5-fluoro-2'-deoxyuridinyl]-2'-deoxy-α-L-uridine (25c)

The 3'-O-acetyl-β-D-5-fluoro-2'-deoxyuridine (0.95 g, 3.29 mmol) was dissolved in dry acetonitrile (125 ml).

Sublimed 1H-tetrazole (350 mg, 4.91) was added and the mixture was stirred under an argon atmosphere for 15 minutes. The solution of 21c (4.91 mmol), dissolved in 5 ml of dry acetonitrile was added via syringe to the reaction solution over 5 minutes. The mixture was allowed to stir at room temperature for three hours. The acetonitrile was evaporated in vacuo to a residue. This residue was triturated with a 70% EtOAc/ether mixture. The undissolved tetrazole was filtered off and the filtrate was evaporated to give a dry yellow foam. This compound was further purified on a silica gel column using 5% MeOH/CHCl$_3$ to give the pure product (2.81 g, 97% yield).

3'-acetoxy-β-D-5'-fluoro-2'-deoxyuridinyl)-α-L-2'-deoxyuridine methyl phosphate ester (26c)

The dimer, 25c (2.81 g, 3.2 mmol), was dissolved in a mixture of THF:pyridine:water (25:6:0.6). Iodine crystals (150 mg) were added and the contents of the loosely stoppered flask were allowed to stir for 1 hour. Excess iodine was discharged by the addition of a few drops of saturated sodium thiosulfate. The reaction mixture was then evaporated to dryness. The crude product was dissolved in EtOAc washed with saturated NaHCO$_3$ solution and brine. The organic layer was dried over Na$_2$SO$_4$, filtered and evaporated in vacuo. The residue (1.48 g) was dissolved in 25 ml of 80% acetic acid/water solution and was stirred until the reaction was completed. The solvent was evaporated and the residue was purified on a silica gel column, using 10% MeOH/CHCl$_3$. Fractions containing one spot by TLC (10% MeOH/CHCl$_3$ Rf=0.4) were pooled and evaporated to give the pure product (0.465 g, 25% yield).

NMR: (CD$_3$OD) δ=2.09 (d, 3H), 2.40 (m, 3H), 2.80 (m, 1H), 3.78 (dd, 3H), 4.30 (m, 3H), 4.63 (m, 3H), 5.05 (m, 1H), 5.23 (m, 1H), 5.70 (d, 1H), 6.13 (m, 1H), 6.20 (m, 1H), 7.73 (d, 1H), 7.82 (d, 1H).

P$^{31}$ NMR: (CD$_3$OD) δ=0.56 (s), 0.84 (s).

3'-O-(β-D-5-fluoro-2'-deoxyuridinyl)-α-L-2'-deoxyuridine (27c)

The O-protected dimer, 26c (465 mg, 0.78 mmol) was treated with 50 ml of saturated methanolic ammonia at room temperature until the reaction was completed. The solvent was stripped off in vacuo and the residue was purified on DEAE cellulose ion exchange column using gradient of NH$_4$CO$_3$ buffer from 0.02–0.2 M. Pure fractions were evaporated at 40° C. in high vacuo to dryness to give the pure product (370 mg, 87.7% yield).

NMR: (CD$_3$OD) δ=2.23 (m, 2H), 2.29 (d, 1H), 2.73(m, 1H), 4.0 (d, 2H), 4.42 (m, 1H), 4.56 (m, 1H), 4.81 (m, 1H), 5.69 (d, 1H), 6.24 (m, 2H), 7.85 (d, 1H), 8.02 (d, 1H).

P$^{31}$ NMR: (CD$_3$OD) δ=1.25 (s).

D. β-L, β-L 5 FUdR dimer

5'-O-dimethoxytrityl-β-L-5-fluoro-2'-deoxyuridine (20d)

β-L-5-fluoro-2'-deoxyuridine (19d, 1.42 g, 5.77 mmol) was dissolved in 25 ml of dry, distilled pyridine. To this solution was added 4,4'-dimethoxytrityl chloride (2.34 g, 6.92 mmol) and 4-dimethylamino pyridine (DMAP) (140 mg, 1.15 mmol). The mixture was stirred under an argon atmosphere for 16 hours. After this time, the pyridine was stripped off in vacuo. The residue was dissolved in EtOAc (100 ml). The organic layer was washed with saturated NaHCO$_3$, and with brine. The organic layer was dried over Na$_2$SO$_4$, filtered and evaporated in vacuo to a residue which was purified on a silica gel column using 5% MeOH/CHCl$_3$. Pure fractions were pooled and evaporated to give the pure product as an off-white foam (2.88 g, 88.7% yield).

NMR: (CDCl$_3$) δ=2.25 (m, 1H), 2.50 (m, 1H), 3.50 (m, 2H), 3.80 (s, 6H), 4.08 (m, 1H), 4.58 (m, 1H), 6.30 (t, 1H), 6.84 (d, 4H), 7.28 (m, 9 H), 7.82 (d, 1H), 8.58 (br s, 1H).

5'-O-dimethoxytrityl-β-L-5-fluoro-2'-deoxyuridine-3'-N,N-diisopropylmethoxy phosphoramidite (21d)

The 5'-O-dimethoxytrityl-β-L-5-fluoro-2'-deoxyuridine (20d, 840 mg, 1.53 mmol) was dissolved in anhydrous dichloromethane (50 ml). N,N-diisopropylethylamine (1.1 ml, 6.13 mmol) was added through a septum, followed by chloro-N,N-diisopropylmethoxyphosphine (0.42 ml, 2.3 mmol), under an argon atmosphere. The reaction was stirred for 30 minutes. The solvent was evaporated and the residue was partitioned between an 80% EtOAc/triethylamine mixture and brine. The organic layer was washed with saturated NaHCO$_3$ solution and brine. The organic residue was evaporated to dryness and the residue was purified on a silica gel column using a mixture of dichloromethane, EtOAc and triethylamine (45:45:10; Rf=0.69). The product (700 mg, 65%) was isolated as a yellow foam and it was used in the next step without further purification.

5'-O-dimethoxytrityl-3'-[O-(3'-O-acetyl)-β-L-5-fluoro-2'-deoxyuridinyl]-β-L-5-fluoro-2'-deoxyuridine (25d)

The 3'-acetyl-β-L-5-deoxyuridine, 24d (330 mg, 1.15 mmol) was dissolved in dry acetonitrile (50 ml). Sublimed 1H-tetrazole (120 mg, 1.77 mmol) was added and the mixture was stirred under an argon atmosphere for 15 minutes. The solution of 21d (950 mg, 1.36 mmol), dissolved in 5 ml of dry acetonitrile was added via syringe to the reaction solution over 5 minutes. The mixture was allowed to stir at room temperature for three hours. The acetonitrile was evaporated in vacuo to a residue. This residue was triturated with a 70% EtOAc/ether mixture. The undissolved tetrazole was filtered off and the filtrate was evaporated to give a dry yellow foam. This foam was purified on a silica gel column using 5% MeOH/CHCl$_3$ to give the pure product (960 mg, 93% yield).

NMR: (CDCl$_3$) δ=2.10 (d, 3H), 2.28 (m, 2H), 2.49 (m, 2H), 3.42 (m, 3H), 3.51 (dd, 3H), 3.76 (s, 6H), 4.07 (m, 1H), 4.55 (m, 1H), 4.87 (m, 1H), 5.23 (m, 1H), 6.30 (m, 2H), 6.84 (d, 4H), 7.30 (m, 9H), 7.82 (m, 2H).

(3'-acetoxy-β-L-5-fluoro-2'-deoxyuridinyl)-β-L-5-fluoro-2'-deoxyuridine methyl phosphate ester (26d)

The dimer, 25d (960 mg, 1.07 mmol), was dissolved in a mixture containing THF:pyridine:water (12:3:0.3). Iodine crystals (50 mg) were added and the contents of the loosely stoppered flask were allowed to stir for 1 hour. Excess iodine was discharged by the addition of a few drops of saturated sodium thiosulfate. The reaction mixture was then evaporated to dryness. The crude product was dissolved in EtOAc washed with saturated NaHCO$_3$ solution and brine. The organic layer was dried over Na$_2$SO$_4$, filtered and evaporated in vacuo. The residue (530 mg) was dissolved in 20 ml of 80% acetic acid/water solution and was stirred until the reaction was completed. The solvent was evaporated and the residue was purified on a silica gel column, using 10% MeOH/CHCl$_3$. Fractions containing one spot by TLC (10% MeOH/CHCl$_3$ Rf=0.35) were pooled and evaporated to give the pure product (310 mg, 46% yield).

NMR: (CD$_3$OD) δ=2.08 (s, 3H), 2.35–2.54 (m, 4H), 3.79 (m, 2H), 3.83 (dd, 3H), 4.18 (m, 2H), 5.08 (m, 1H), 5.29 (m, 1H), 6.24 (m, 1H), 7.86 (dd, 1H), 8.19(dd, 1H).

P$^{31}$ NMR: (CD$_3$OD) δ=0.82 (s), 1.03 (s).

3'-O-(β-L-5-fluoro-2'-deoxyuridinyl)-β-L-5-fluoro-2'-deoxyuridine (27d)

The O-protected dimer, 26d (300 mg, 0.49 mmol) was treated with 50 ml of saturated methanolic ammonia at room temperature until the reaction was completed. The solvent was stripped off in vacuo and the residue was purified on DEAE cellulose ion exchange column using gradient of NH$_4$CO$_3$ buffer from 0.02–0.2 M. Pure fractions were evaporated at 40° C. in high vacuo to dryness to give the pure product (240 mg, 85% yield).

NMR: (CD$_3$OD) δ=2.25 (m, 3H), 2.50 (m, 1H), 3.79 (d, 2H), 4.03 (m, 1H), 4.08 (m, 2H), 4.18 (m, 1H), 4.44 (m, 1H), 4.90 (m, 1H), 6.25 (t, 1H), 8.01 (d, 1H), 8.24 (d, 1H).

P$^{31}$ NMR: (CD$_3$OD) δ=0.18 (s).

E. β-L, β-D 5 FUdR dimer

5'-O-dimethoxytrityl-3'-[O-(3'-O-acetyl)-β-D-5-fluoro-2'-deoxyuridinyl]-β-L-5-fluoro-2'-deoxyuridine (25e)

The 3'-O-acetyl-β-D-5-fluoro-2'-deoxyuridine (250 mg, 0.97 mmol) was dissolved in dry acetonitrile (50 ml). Sublimed 1H-tetrazole (100 mg, 1.46 mmol) was added and the mixture was stirred under an argon atmosphere for 15 minutes. The solution of 21e (1.02 g, 1.46 mmol), dissolved in 5 ml of dry acetonitrile was added via syringe to the reaction solution over 5 minutes. The mixture was allowed to stir at room temperature for three hours. The acetonitrile was evaporated in vacuo to a residue. This residue was triturated with a 70% EtOAc/ether mixture. The undissolved tetrazole was filtered off and the filtrate was evaporated to give a dry yellow foam. This foam was purified on a silica gel column using 5% MeOH/CHCl$_3$ to give the pure product quantitatively.

(3'-acetoxy-β-D-5-fluoro-2'-deoxyuridinyl)-β-L-5-fluoro-2'-deoxyuridine methyl phosphonate ester (26e)

The dimer in reduced form, 25 (700 mg, 0.78 mmol), was dissolved in a mixture containing THF:pyridine:water (25:6:0.6). Iodine crystals (100 mg) were added and the contents of the loosely stoppered flask were allowed to stir for 2.5 hours. Excess iodine was discharged by the addition of a few drops of saturated sodium thiosulfate. The reaction mixture was then evaporated to dryness. The crude product was dissolved in EtOAc washed with saturated NaHCO$_3$ solution and brine. The organic layer was dried over Na$_2$SO$_4$, filtered and evaporated in vacuo. The residue was dissolved in 25 ml of 80% acetic acid/water solution and was stirred until the reaction was completed. The solvent was evaporated and the residue was purified on a silica gel column, using 10% MeOH/CHCl$_3$. Fractions containing one spot by TLC (10% MeOH/CHCl$_3$ Rf=0.35) were pooled and evaporated to give the pure product (340 mg, 71.4% yield).

NMR: (DMSO-d$_6$) δ=2.06 (s, 3H), 2.37 (m, 4H), 3.45 (m, 2H), 3.65 (d, 3H), 4.20 (m, 3H), 4.95 (m, 1H), 5.30 (m, 1H), 5.96 (m, 1H), 6.15 (t, 2H), 7.99 (d, 1H), 8.16 (d, 1H), 11.90(br s, 2H).

P$^{31}$ NMR: (DMSO-d$_6$) δ=1.93 (s), 2.01 (s).

3'-O-(β-D-5-fluoro-2'-deoxyuridinyl)-β-L-5-fluoro-2'-deoxyuridine (27e)

The O-protected dimer, 26e (340 mg, 0.57 mmol) was treated with 100 ml of saturated methanolic ammonia at room temperature until the reaction was completed. The solvent was stripped off in vacuo and the residue was purified on DEAE cellulose ion exchange column using gradient of NH$_4$CO$_3$ buffer from 0.02–0.2 M. Pure fractions were evaporated at 40° C. in high vacuo to dryness to give the pure product (200 mg, 66.9% yield).

NMR: (CD$_3$OD) δ=2.20 (m, 3H), 2.53 (m, 1H), 3.79 (d, 2H), 4.05 (m, 3H), 4.16 (m, 1H), 4.45 (m, 1H), 6.27 (t, 2H), 8.01 (d, 1H), 8.04 (d, 1H), 8.26 (d, 1H).

5'-O-(dimethoxytrityl)-α-L-5-fluoro-2'-deoxyuridine-3'-N,N-diisopropylcyanoethyl phosphoramidite (21f)

The 5'-o-dimethoxytrityl-α-L-5-fluoro-2'-deoxyuridine (1.48 g, 2.71 mmol) was dissolved in anhydrous dichloromethane (50 ml). N,N-diisopropylethylamine (1.9 ml, 10.84 mmol) was added through a septum, followed by 2'-cyanoethyl-N,N-diisopropylchlorophosphoramidite (0.78 ml, 3.52 mmol), under an argon atmosphere. The reaction was stirred for 30 minutes. The solvent was evaporated and the residue was partitioned between an 80% EtOAc/triethylamine mixture and brine. The organic layer was washed with saturated NaHCO$_3$ solution and brine. The organic residue was evaporated to dryness and the residue was purified on a silica gel column using a mixture of dichloromethane, EtOAc and triethylamine (45:45:10:Rf= 0.7). The product was isolated quantitatively as a yellow foam and it was used in the next step without further purification.

5'-O-dimethoxytrityl-3'-[O-(5'-O-dimethoxytrityl)-β-D-5-fluoro-2'-deoxyuridinyl]-α-L-5-fluoro-2'-deoxyuridine (25f)

The 5'-O-dimethoxytrityl-β-D-5-fluoro-2'-deoxyuridine (0.44 g, 0.81 mmol) was dissolved in dry acetonitrile (20 ml). Sublimed 1H-tetrazole (90 mg) was added and the mixture was stirred under an argon atmosphere for 15 minutes. The solution of 21f (0.51 mg, 0.67 mmol), dissolved in 10 ml of dry acetonitrile was added via syringe to the reaction solution over 5 minutes. The mixture was allowed to stir at room temperature for three hours. The acetonitrile was evaporated in vacuo to a residue. This residue was triturated with a 70% EtOAc/ether mixture. The undissolved tetrazole was filtered off and the filtrate was evaporated to give a dry yellow foam (970 mg). This foam was used in the next step without further purification.

(β-D-5-fluoro-2'-deoxyuridinyl)-α-L-5-fluoro-2'-deoxyuridine cyanoethyl phosphonate ester (26f)

The dimer, 25f (970 mg), was dissolved in 16 ml of THF and 4 ml of pyridine containing 0.4 ml of water. Iodine crystals (50 mg) were added and the contents of the loosely stoppered flask were allowed to stir for 1 hour. Excess iodine was discharged by the addition of few drops of saturated sodium thiosulfate. The reaction mixture was then evaporated to dryness. The crude product was EtOAc washed with saturated NaHCO$_3$ solution and brine. The organic layer was dried over Na$_2$SO$_4$, filtered and evaporated in vacuo. The residue was dissolved in 20 ml of 80% acetic acid/water solution and was stirred until the reaction was completed. The solvent was evaporated and the residue was purified on a silica gel column, using 10–15% MeOH/CHCL$_3$. Fractions containing one spot by TLC (10% MeOH/CHCL$_3$ Rf=0.35) were pooled and evaporated to give the pure product (330 mg).

3'-O-(β-D-5-fluoro-2'-deoxyuridinyl)-α-L-5-fluoro-2'-deoxyuridine (27f)

The O-protected dimer, 26f (200 mg) was treated with 20 ml of concentrated ammonia solution until the reaction is completed. The solvent was stripped off in vacuo and the residue was purified on DEAE cellulose ion exchange column using gradient of $NH_4CO_3$ buffer from 0.02–0.2 M. Pure fractions were evaporated at 40° C. in high vacuo to dryness to give the pure product (79 mg).

NMR: ($CD_3OD$) δ=2.45 (m, 3H), 2.69 (m, 1H), 3.67 (m, 2H), 3.76 (m, 2H), 4.13 (t, 1H), 4.65 (m, 2H), 6.19 (m, 2H), 7.98 (td, 2H).

$P^{31}$ NMR: ($D_2O$) δ=−1.0(s)

5'-O-dimethoxytrityl-3'-[O-(3'-O-acetyl)-β-L-5-fluoro-2'-deoxyuridinyl]-α-L-5-fluoro-2'-deoxyuridine (25g)

The 3'-O-acetyl-β-D-5-fluoro-2'-deoxyuridine (0.19 g, 0.67 mmol) was dissolved in dry acetonitrile (20 ml). Sublimed 1H-tetrazole (70 mg) was added and the mixture was stirred under an argon atmosphere for 15 minutes. The solution of 21f (0.51 mg, 0.67 mmol), dissolved in 10 ml of dry acetonitrile was added via syringe to the reaction solution over 5 minutes. The mixture was allowed to stir at room temperature for three hours. The acetonitrile was evaporated in vacuo to a residue. This residue was triturated with a 70% EtOAc/ether mixture. The undissolved tetrazole was filtered off and the filtrate was evaporated to give a dry yellow foam (611 mg). This foam was used in the next step without further purification.

(3'-acetoxy-β-L-5-fluoro-2'-deoxyuridinyl)-α-L-5-fluoro-2'-deoxyuridine cyanoethyl phosphonate ester (26g)

The dimer, 25g (611 mg), was dissolved in 8 ml of THF and 2 ml of pyridine containing 0.2 ml of water. Iodine crystals (30 mg) were added and the contents of the loosely stoppered flask were allowed to stir for 1 hour. Excess iodine was discharged by the addition of few drops of saturated sodium thiosulfate. The reaction mixture was then evaporated to dryness. The crude product was EtOAc washed with saturated $NaHCO_3$ solution and brine. The organic layer was dried over $Na_2SO_4$, filtered and evaporated in vacuo. The residue was dissolved in 20 ml of 80% acetic acid/water solution and was stirred until the reaction was completed. The solvent was evaporated and the residue was purified on a silica gel column, using 10–15% $MeOH/CHCL_3$. Fractions containing one spot by TLC (10% $MeOH/CHCL_3$ Rf=0.35) were pooled and evaporated to give the pure product (200 mg).

3'-O-(β-L-5-fluoro-2'-deoxyuridinyl)-α-L-5-fluoro-2'-deoxyuridine (27g) [α-Lβ-L 5FUdR Dimer]

The o-protected dimer, 26g (200 mg) was treated with 20 ml of concentrated ammonia solution until the reaction is completed. The solvent was stripped off in vacuo and the residue was purified on DEAE cellulose ion exchange column using gradient of $NH_4CO_3$ buffer from 0.02–0.2 M. Pure fractions were evaporated at 40° C. in high vacuo to dryness to give the pure product (134 mg).

NMR: ($D_2O$) δ=2.30 (m, 3H), 2.71 (m, 1H), 3.65 (m, 2H), 4.03 (m, 2H), 4.08 (t, 1H), 4.47 (m, 1H), 4.68 (m, 2H), 6.13 (d, 1H), 6.24 (td, 1H), 7.89 (d, 1H), 7.95 (d, 1H).

$P^{31}$ NMR: ($D_2O$) δ=0.32(s)

5'-O-(dimethoxytrityl)-β-L-2'-deoxyuridine-3'-N,N-diisopropylmethoxy phosphoramidite (21h)

The 5'-O-dimethoxytrityl-α-L-2'-deoxyuridine (1.0 g, 1.88 mmol) was dissolved in anhydrous dichloromethane (50 ml). N,N-diisopropylethylamine (1.31 ml, 7.55 mmol) was added through a septum, followed by chloro-N,N-diisopropylmethoxyphosphine (0.55 ml, 2.83 mmol), under an argon atmosphere. The reaction was stirred for 30 minutes. The solvent was evaporated and the residue was partitioned between an 80% EtOAc/triethylamine mixture and brine. The organic layer was washed with saturated $NaHCO_3$ solution and brine. The organic residue was evaporated to dryness and the residue was purified on a silica gel column using a mixture of dichloromethane, EtOAc and triethylamine (50:40:10; Rf=0.8). The product was isolated quantitatively as a yellow foam and it was used in the next step without further purification.

5'-O-dimethoxytrityl-3'-[O-(3'-O-acetyl)-β-D-5-fluoro-2'-deoxyuridinyl]-β-L-2'-deoxyuridine (25h)

The 3'-O-acetyl-β-D-5-fluoro-2'-deoxyuridine (0.54 g, 1.88 mmol) was dissolved in dry acetonitrile (50 ml). Sublimed 1H-tetrazole (200 mg) was added and the mixture was stirred under an argon atmosphere for 15 minutes. The solution of 21 h (1.88 mmol), dissolved in 15 ml of dry acetonitrile was added via syringe to the reaction solution over 5 minutes. The mixture was allowed to stir at room temperature for three hours. The acetonitrile was evaporated in vacuo to a residue. This residue was triturated with a 70% EtOAc/ether mixture. The undissolved tetrazole was filtered off and the filtrate was evaporated to give a dry yellow foam (1.08 g). This foam was used in the next step without further purification.

(3'-acetoxy-β-D-5-fluoro-2'-deoxyuridinyl)-β-L-2'-deoxyuridine methyl phosphonate ester (26h)

The dimer, 25h (1.08 g), was dissolved in 15 ml of THF and 3 ml of pyridine containing 0.3 ml of water. Iodine crystals (100 mg) were added and the contents of the loosely stoppered flask were allowed to stir for 1 hour. Excess iodine was discharged by the addition of few drops of saturated sodium thiosulfate. The reaction mixture was then evaporated to dryness. The crude product was EtOAc washed with saturated $NaHCO_3$ solution and brine. The organic layer was dried over $Na_2SO_4$, filtered and evaporated in vacuo. The residue was dissolved in 25 ml of 80% acetic acid/water solution and was stirred until the reaction was completed. The solvent was evaporated and the residue was purified on a silica gel column, using 10–15% $MeOH/CHCL_3$. Fractions containing one spot by TLC (10% $MeOH/CHCL_3$ Rf=0.4) were pooled and evaporated to give the pure product (400 mg).

3'-O-(β-D-5-fluoro-2'-deoxyuridinyl)-β-L-2'-deoxyuridine (27h)

The O-protected dimer, 26h (400 mg) was treated with 100 ml of methnolic ammonia solution until the reaction is completed. The solvent was stripped off in vacuo and the residue was purified on DEAE cellulose ion exchange column using gradient of $NH_4CO_3$ buffer from 0.02–0.2 M. Pure fractions were evaporated at 40° C. in high vacuo to dryness to give the pure product (175 mg).

NMR: ($D_2O$) δ=2.40 (m, 3H), 2.61 (m, 1H), 3.80 (m,2H), 4.10 (m, 2H), 4.18 (m,2H), 4.55 (m, 1H), 4.80 (m, 1H), 5.85 (d, 1H), 6.30 (q, 2H), 7.85 (d, 1H), 8.06 (d, 1H).

$P^{31}$NMR: ($D_2O$) δ=0.20(s)

5'-O-dimethoxytri-tyl-$N^4$-benzoyl-2'-deoxy-β-L-cytidine (20i)

$N^4$-benzoyl-2'-deoxy-β-L-cytidine (0.8 g, 2.42) was dissolved in 50 ml of dry, distilled pyridine. To this solution was added 4,4'-dimethoxytrityl chloride (3.0 g, 8.85 mmol) and 4-dimethylamino pyridine (DMAP) (60 mg, 0.48 mmol). The mixture was stirred under an argon atmosphere for 16 hours. After this time, the pyridine was stripped off in vacuo. The residue was dissolved in EtOAc (100 ml). The organic layer was washed with water, saturated NaHCO$_3$, and brine. The organic layer was dried over Na$_2$SO$_4$, filtered and evaporated in vacuo to a residue which was purified on a silica gel column using 10% MeOH/CHCl$_3$. Pure fractions were pooled and evaporated to give the pure product as an off-white foam (1.49 g, (97% yield). Rf=0.48 in 10% MeOH/CHCl$_3$.

NMR: (CDCl$_3$-d$_6$) δ=2.3 (m, 1H), 2.75 (m, 2H), 3.42 (ddd, 2H), 3.80 (s, 6H), 4.15 (q, 2H), 4.52 (m, 1H), 6.30 (t, 1H), 6.82 (dd, 4H), 7.2–7.6 (m, Ar), 7.85 (d, 2H), 8.32 (d, 1H), 8.76 (br s, 1H).

5'-O-(dimethoxytrityl)-N$^4$-benzoyl-2'-deoxy-β-L-cytidine-3'-N,N-diisopropylmethyl phosphoramidite (21i)

The 5'-O-dimethoxytrityl-N$^4$-benzoyl-2'-deoxy-β-L-cytidine (0.6 g, 0.95 mmol) was dissolved in anhydrous dichloromethane (50 ml). N,N-diisopropylethylamine (0.66 ml, 3.79 mmol) was added through a septum, followed by chloro-N,N-diisopropylmethoxyphosphine (0.28 ml, 1.42 mmol), under an argon atmosphere. The reaction was stirred for 30 minutes. The solvent was evaporated and the residue was partitioned between an 80% EtOAc/triethylamine mixture and brine. The organic layer was washed with saturated NaHCO$_3$ solution and brine. The organic residue was evaporated to dryness and the residue was purified on a silica gel column using a mixture of dichloromethane, EtOAc and triethylamine (60:30:10; Rf=0.8). The product was isolated quantitatively as a yellow foam and it was used in the next step without further purification.

5'-O-dimethoxytrityl-3'-[O-(3'-O-acetyl)-β-D-5-fluoro-2'-deoxyuridinyl]-N$^4$-benzoyl-2'-deoxy-β-L-cytidine (25i)

The 3'-O-acetyl-β-D-5-fluoro-2'-deoxyuridine (0.23 g, 0.78 mmol) was dissolved in dry acetonitrile (30 ml). Sublimed 1H-tetrazole (110 mg) was added and the mixture was stirred under an argon atmosphere for 15 minutes. The solution of 21i (0.94 mmol), dissolved in 15 ml of dry acetonitrile was added via syringe to the reaction solution over 5 minutes. The mixture was allowed to stir at room temperature for three hours. The acetonitrile was evaporated in vacuo to a residue. This residue was triturated with a 70% EtOAc/ether mixture. The undissolved tetrazole was filtered off and the filtrate was evaporated to give a dry yellow foam (0.73 g). This foam was used in the next step without further purification.

(3'-acetoxy-β-D-5-fluoro-2'-deoxyuridinyl)-N$^4$-benzoyl-2'-deoxy-β-L-cytidine methyl phosphonate ester (26i)

The dimer, 25i (0.73 g), was dissolved in 20 ml of THF and 4 ml of pyridine containing 0.4 ml of water. Iodine crystals (100 mg) were added and the contents of the loosely stoppered flask were allowed to stir for 1 hour. Excess iodine was discharged by the addition of few drops of saturated sodium thiosulfate. The reaction mixture was then evaporated to dryness. The crude product was EtOAc washed with saturated NaHCO$_3$ solution and brine. The organic layer was dried over Na$_2$SO$_4$, filtered and evaporated in vacuo. The residue was dissolved in 25 ml of 80% acetic acid/water solution and was stirred until the reaction was completed. The solvent was evaporated and the residue was purified on a silica gel column, using 10–15% MeOH/CHCl$_3$. Fractions containing one spot by TLC (10% MeOH/CHCl$_3$ Rf=0.4) were pooled and evaporated to give the pure product (108 mg).

3'-O-(β-D-5-fluoro-2'-deoxyuridinyl)-2'-deoxy-β-L-cytidine (27i)

The O-protected dimer, 26i (108 mg) was treated with 100 ml of methnolic ammonia solution until the reaction is completed. The solvent was stripped off in vacuo and the residue was purified on DEAE cellulose ion exchange column using gradient of NH$_4$CO$_3$ buffer from 0.02–0.2 M. Pure fractions were evaporated at 40° C. in high vacuo to dryness to give the pure product (56 mg).

NMR: (D$_2$O) δ=2.30 (m, 3H), 2.55 (m, 1H), 3.80 (m, 2H), 4.05 (m, 2H), 4.18 (m, 2H), 4.52 (m, 1H), 4.78 (m, 1H), 6.02 (d, 1H), 6.25 (m, 2H), 7.80 (d, 1H), 8.04 (d, 1H).

P$^{31}$NMR: (D$_2$O) δ=0.05(s)

5'-O-dimethoxytrityl-3'-[O-(3'-O-acetyl)-N$^4$-benzoyl-2'-deoxy-β-L-cytidinyl)-β-D-5-fluoro-2'deoxyuridine (25j)

The 3'-O-acetyl-β-D-5-fluoro-2'-deoxyuridine (0.25 g, 0.67 mmol) was dissolved in dry acetonitrile (30 ml). Sublimed 1H-tetrazole (94 mg) was added and the mixture was stirred under an argon atmosphere for 15 minutes. The solution of 21j (0.51 g, 0.67 mmol), dissolved in 15 ml of dry acetonitrile was added via syringe to the reaction solution over 5 minutes. The mixture was allowed to stir at room temperature for three hours. The acetonitrile was evaporated in vacuo to a residue. This residue was triturated with a 70% EtOAc/ether mixture. The undissolved tetrazole was filtered off and the filtrate was evaporated to give a dry yellow foam (0.49 g). This foam was used in the next step without further purification.

(3'-acetoxy-N$^4$-benzoyl-2'-deoxy-β-L-cytidinyl)-β-D-5-fluoro-2'-deoxyuridinyl cyanoethyl phosphonate ester (26j)

The dimer, 25j (0.49 g), was dissolved in 8 ml of THF and 2 ml of pyridine containing 0.2 ml of water. Iodine crystals (30 mg) were added and the contents of the loosely stoppered flask were allowed to stir for 1 hour. Excess iodine was discharged by the addition of few drops of saturated sodium thiosulfate. The reaction mixture was then evaporated to dryness. The crude product was EtOAc washed with saturated NaHCO$_3$ solution and brine. The organic layer was dried over Na$_2$SO$_4$, filtered and evaporated in vacuo. The residue was dissolved in 20 ml of 80% acetic acid/water solution and was stirred until the reaction was completed. The solvent was evaporated and the residue was purified on a silica gel column, using 10–15% MeOH/CHCl$_3$. Fractions containing one spot by TLC (10% MeOH/CHCl$_3$ Rf=0.4) were pooled and evaporated to give the pure product (188 mg).

3'-O-(2'-deoxy-β-L-cytidinyl)-β-D-5-fluoro-2'-deoxyuridine (27j)

The O-protected dimer, 26j (188 mg) was treated with 100 ml of concentrated ammonia solution until the reaction is completed. The solvent was stripped off in vacuo and the residue was purified on DEAE cellulose ion exchange column using gradient of NH$_4$CO$_3$ buffer from 0.02–0.2 M.

Pure fractions were evaporated at 40° C. in high vacuo to dryness to give the pure product (105 mg).

NMR: ($D_2O$) δ=2.30 (m, 3H), 2.50 (m, 1H), 3.80 (m, 2H), 4.05 (m, 2H), 4.10 (m, 2H), 4.20 (m, 1H), 4.52 (m, 1H), 4.75 (m, 1H), 6.05 (d, 1H), 6.29 (q, 2H), 7.89 (d, 1H), 9.03 (d, 1H).

$P^{31}$NMR: ($D_2O$) δ=0.05(s)

5'-O-dimethoxytrityl-3'-[O-(3'-O-acetyl)-$N^4$-benzoyl-2'-deoxy-α-L-cytidinyl)-β-D-5-fluoro-2'-deoxyuridine (25k)

The 3'-O-acetyl-β-D-5-fluoro-2'-deoxyuridine (0.19 g, 0.51 mmol) was dissolved in dry acetonitrile (30 ml). Sublimed 1H-tetrazole (80 mg) was added and the mixture was stirred under an argon atmosphere for 15 minutes. The solution of 21k (0.45 g, 0.61 mmol), dissolved in 15 ml of dry acetonitrile was added via syringe to the reaction solution over 5 minutes. The mixture was allowed to stir at room temperature for three hours. The acetonitrile was evaporated in vacuo to a residue. This residue was triturated with a 70% EtOAc/ether mixture. The undissolved tetrazole was filtered off and the filtrate was evaporated to give a dry yellow foam (0.42 g). This foam was used in the next step without further purification.

(3'-acetoxy-$N^4$-benzoyl-2'-deoxy-α-L-cytidinyl)-β-D-5-fluoro-2'-deoxyuridinyl cyanoethyl phosphonate ester (26k)

The dimer, 25k (0.42 g), was dissolved in 10 ml of THF and 2 ml of pyridine containing 0.2 ml of water. Iodine crystals (45 mg) were added and the contents of the loosely stoppered flask were allowed to stir for 1 hour. Excess iodine was discharged by the addition of few drops of saturated sodium thiosulfate. The reaction mixture was then evaporated to dryness. The crude product was EtOAc washed with saturated $NaHCO_3$ solution and brine. The organic layer was dried over $Na_2SO_4$, filtered and evaporated in vacuo. The residue was dissolved in 25 ml of 80% acetic acid/water solution and was stirred until the reaction was completed. The solvent was evaporated and the residue was purified on a silica gel column, using 10–15% $MeOH/CHCl_3$. Fractions containing one spot by TLC (10% $MeOH/CHCl_3$ Rf=0.4) were pooled and evaporated to give the pure product (125 mg).

3'-O-(2'-deoxy-α-L-cytidinyl)-β-D-5-fluoro-2'-deoxyuridine (27k)

The O-protected dimer, 26k (125 mg) was treated with 100 ml of concentrated ammonia solution until the reaction is completed. The solvent was stripped off in vacuo and the residue was purified on DEAE cellulose ion exchange column using gradient of $NH_4CO_3$ buffer from 0.02–0.2 M). Pure fractions were evaporated at 40° C. in high vacuo to dryness to give the pure product (40 mg).

NMR: ($D_2O$) δ=2.15 (m, 1H), 2.35 (m, 1H), 2.60 (m, 1H), 2.71 (m, 1H), 3.81 (m, 2H), 3.97 (m, 2H), 4.22 (m, 1H), 4.52 (m, 2H), 6.02 (d, 1H), 6.15 (dd, 1H), 6.28 (t, 1H), 7.87 (d, 1H), 8.03 (d, 1H).

$P^{31}$NMR: ($D_2O$) δ=0.12(s)

EXAMPLE 5

In Vivo Activity of Nucleoside Analogs Against *P. falciparum*

A. In Vitro Culture of the Malarial Parasite

*P. falciparum*, FCQ27, was maintained in culture using the techniques described by Trager & Jensen (W. Traqer and J. B. Jensen, Science, 193 673–675 (1976)). Cultures containing 2% hematocrit suspensions of parasitized human type $O^+$ erythrocytes in RPMI 1640 medium, supplemented with 25 mM HEPES-KOH, pH 7.2, 25 mM $NaHCO_3$ and 10% human type $O^+$ serum (v/v) are maintained in modular incubator chambers at 37° C. in a gas mixture of 5% $O_2$, 5% $CO_2$ and 90% $N_2$. The isolate of *P. falciparum* used in these experiments was FCQ27, routinely maintained in synchronized or asynchronous in vitro cultures at low hematocrit.

B. In Vitro Toxicity Against *P. falciparum*

The potential toxicity of nucleoside analogues against *P. falciparum* in culture was tested in microtitre plates over the range of drug concentrations for 24 hours. The procedures for monitoring parasite viability is well established (A. M. Gero, H. V. Scott, W. J. O'Sullivan and R. I. Christopherson, Mol. Biochem. Parasitol. 34, 87–89 (1989)) and is based on radiolabelled hypoxanthine or isoleucine incorporation. The incorporation of [G-$^3$H]hypoxanthine into the nucleic acids of *P. falciparum* was used to assess the viability of the parasite in vitro. Microculture plates were prepared with each well containing 225 μl of a 2% hematocrit culture of asynchronous parasited erythrocytes (1% parasitized cells). Each plate, containing varying concentrations of the drug to be studied (up to 200 μM final concentration for initial screen), was incubated for 24 h at 37° C. in a gas mixture of 5% $O_2$, 5% $CO_2$ and 90% $N_2$, at which point [G-$^3$H] hypoxanthine was added to each well and the incubation continued under identical conditions for a further 18–20 h. The control infected cells (i.e. without drug), routinely reached a parasitemia of 6–8% before harvesting. Expediency was aided by 96-well plate counter using lactate dehydrogenase for the drug susceptibility assay (L. K. Basco, F. Marguet, M. T. Makler and J. Lebbras, Exp. Parasitol. 80, 260–271 (1995); M. T. Makler and D. J. Hinrichs; Am. J. Trop. Med. Hyg. 48, 205–210 (1993)). This assay gave the identical results to the hypoxanthine technique. In addition, for each experiment, microscopic counting of Giemsa stained thin slides was used as a control.

C. Transport and Metabolism in *P. falciparum* Infected Erythrocytes

The metabolism of the L-nucleoside conjugates was studied by HPLC analysis. The primary aim was to determine their ability to be catabolized by parasite purine salvage enzymes. Some effect on the purine metabolic pools was also observed.

For each HPLC determination 200 μL of packed cells of 80–90% trophozoite infected cells were used. These were isolated from in vitro cultures by synchronization of the parasites in in vitro cultures using sterile D-sorbitol (L. Lambros and J. P. Vanderberg, Parasitol. 65, 418–420 (1979)) followed by separation of the trophozoites from non infected erythrocytes by Percoll gradients as described previously (A. M. Gero, H. V. Scott, W. J. O'Sullivan and R. I. Christopherson, Mol. Biochem. Parasitol. 34, 87–89 (1989)). Trophozoites were incubated at 37° C. for 2 hours with each compound to be tested. Compounds were incubated with both whole infected cells as whole and lyzed uninfected normal erythrocytes to determine:

a) entry to the cell (whether they were transported);
b) the metabolic effect within the cell (was the compound metabolized);

c) the capacity of broken or lyzed cells to catabolize the compound which may not be able to enter the unbroken cell (i.e. if the compound was transported into the cell, would it be metabolized to the active form).

Drug incubation was terminated by centrifugation through silicon oil using the method of Upston and Gero (J. M. Upston and A. M. Gero, Biochem. Biophys. Acta. 1236, 249–258 (1995)). This procedure separated intact trophozoites from extracellular non-transported drug solution.

The metabolism of nucleosides with potential chemotherapeutic activity was assessed by the analysis of cytoplasmic samples by reverse phase ion-pair high performance liquid chromatography (R. S. Toguzov, Y. V. Tikhonov, A. M. Pimenov, V. Prokudin, Journal of Chromatography, I. Biomedical Appl. 434, 447–453 (1988)). Nucleotides, nucleosides and bases were separated by this HPLC method.

The transport and metabolism of purine nucleosides differ considerably between the normal human erythrocyte and human erythrocytes which have been infected with *Plasmodium falciparum*. The malaria parasite is unable to synthesize purines de novo and so therefore must rely on salvage pathways to obtain purines it requires for growth and division (L. W. Scheibel & T. W. Sherman, In: Malaria: Principles and practice of Malariology (W. H. Wernsdorfer & I. McGregor, Eds.) V. 1, 234–242 (1988)). Additionally, normal human erythrocytes do not contain significant levels of pyrimidine nucleotides (E. Szabodos & R. I. Christopherson, Biochem. Edu. 19, 90–94 (1991)), and the parasite is unable to obtain pyrimidine bases by salvage pathways and again has to rely on de novo synthesis (L. W. Scheibel & T. W. Sherman, In: Malaria: Principles and practice of Malariology (W. H. Wernsdorfer & I. McGregor, Eds.) V. 1, 234–242 (1988)). These modifications to the metabolic pathways of the infected erythrocytes, along with modifications of their transport system, represent significant variations from normal erythrocytes and may present an opportunity for the use of selectively toxic compounds against the parasites.

Nucleosides have attracted researchers as potential therapeutic agents. Naturally occurring nucleosides are usually in the β-D configuration. Therefore most of nucleoside analogues designed for the treatment of cancer, viral and parasitic diseases have been synthesized in this stereochemical configuration. Recent discoveries in our laboratories at the University of Georgia, the University of Iowa and at Yale University, as well as at universities in France and Italy, have confirmed that most L-nucleosides exhibit low toxicity because normal cells do not utilize them for building RNA or DNA and don't metabolize them.

Recently, Dr. Gero and her coworkers discovered that the nonphysiological β-L-adenosine can be selectively transported into an erythrocyte infected with *P. falciparum* (A. M. Gero & J. M. Upston, In: Pyrine & Pyrimidine Metabolism in Man VIII (A. Sahota & M. Taylor, Eds) Plenum Press, NY, 495–498 (1995)). Normal erythrocytes and other cell types are completely impermeable to this compound.

During the Phase I study, we used this unique ability of the non-natural nucleoside analogues for selective transport to the malaria infected cells to create a novel synthetic L-nucleoside based class of non-toxic antimalarial agents. Our working hypothesis was based on the design and biological evaluation of novel chemical entities which would consist of both 5-fluorodeoxyuridine (FUdR), a known inhibitor of thymidylate synthase, and an L-nucleoside or its derivatives. The number of "dimers" consisting of α- or β-L isomeric modification of physiological nucleosides or their derivatives was conjugated with FUdR by phosphate or pro-phosphate linkage. Along with anticancer activity, FUdR has a potential as an antimalarial agent (S. A. Queen, D. L. Vander Jagt & P. Reyer, Antimicrobial Agents & Chemotherapy. 34, 1393–1398 (1990). Unfortunately, FUdR's toxicity limits its use. In theory, combining FUdR with an L-nucleoside unit would result in an entity that could selectively transport an active component to infected cells while having no effect on normal cells.

Figure 7:
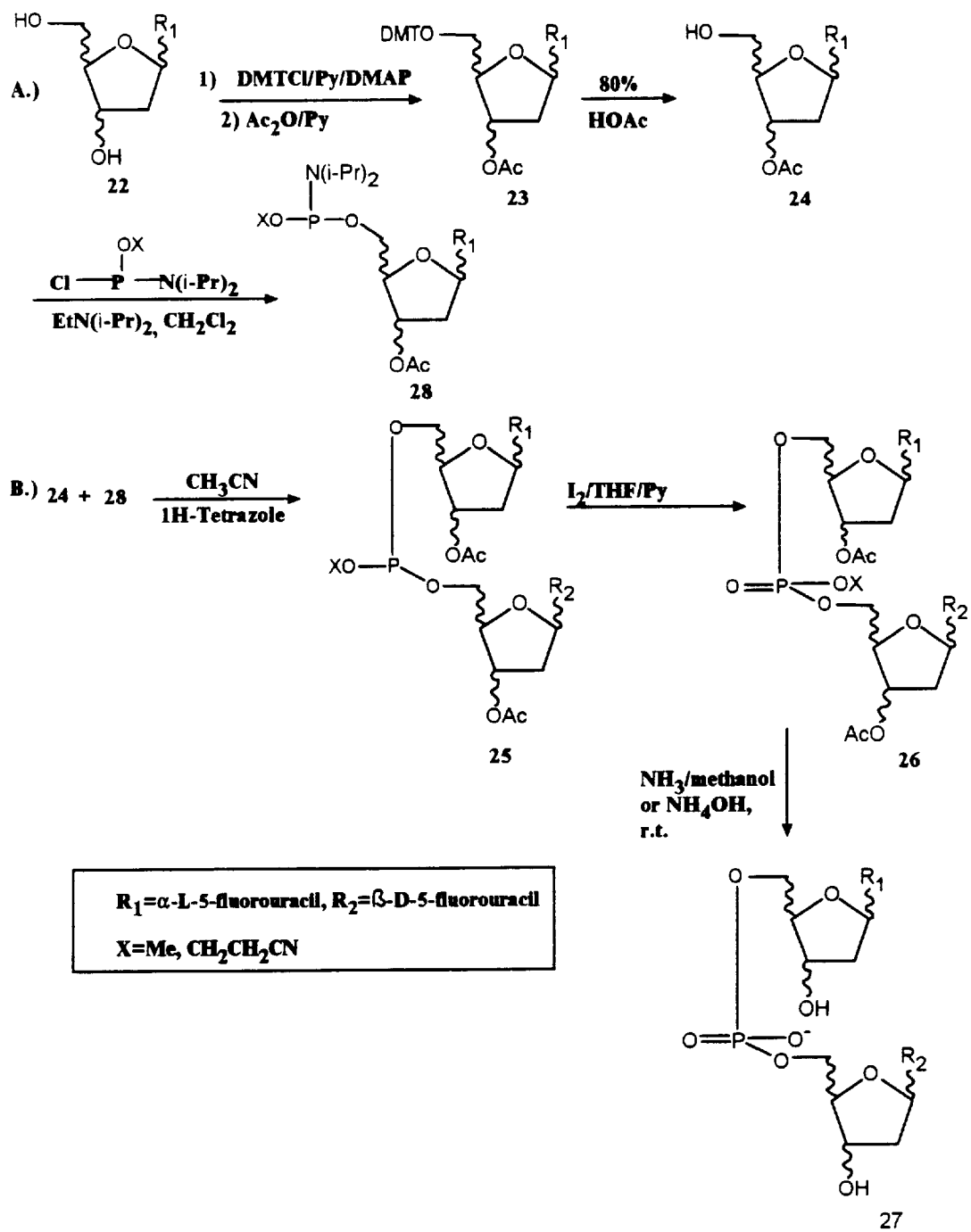
Figure 8:
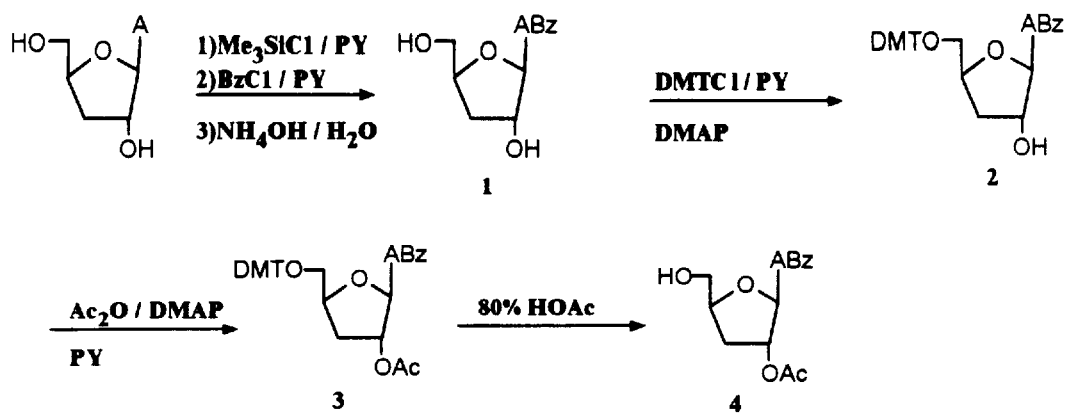
Figure 8:
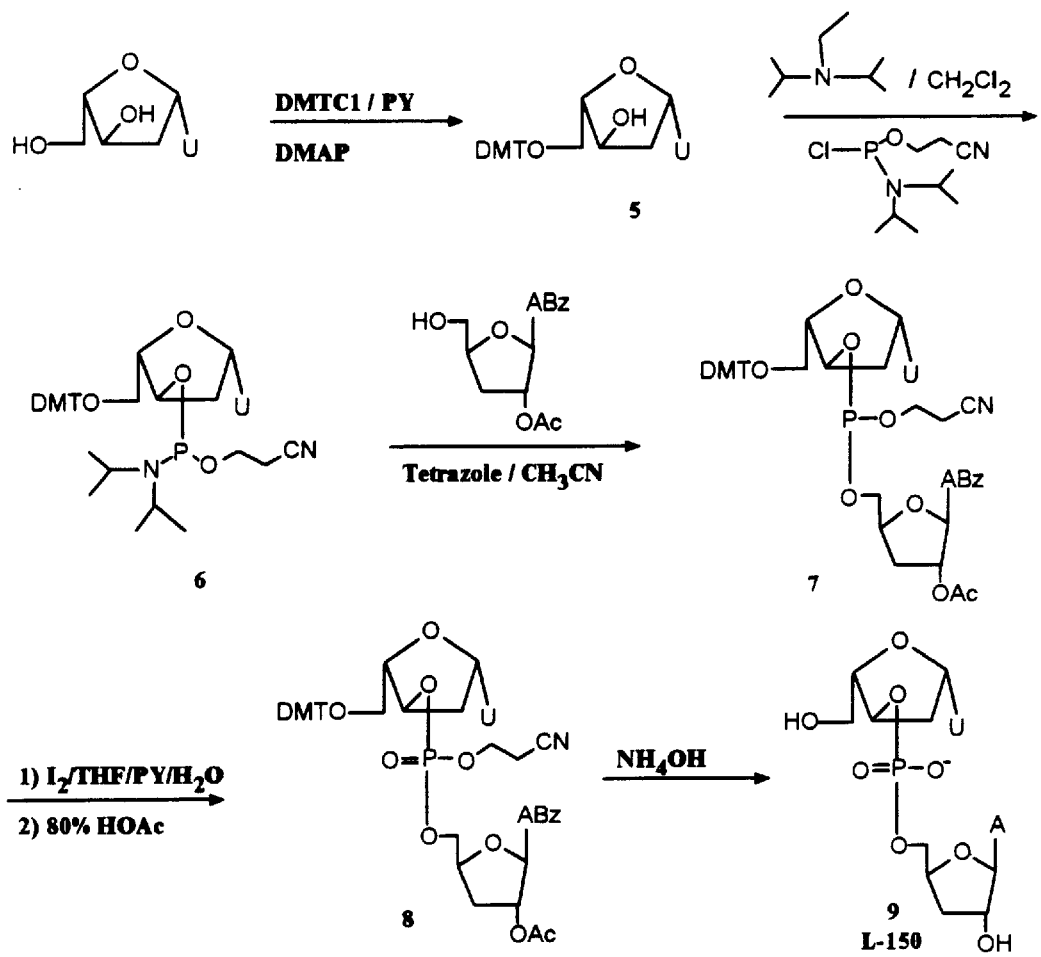
Figure 9:
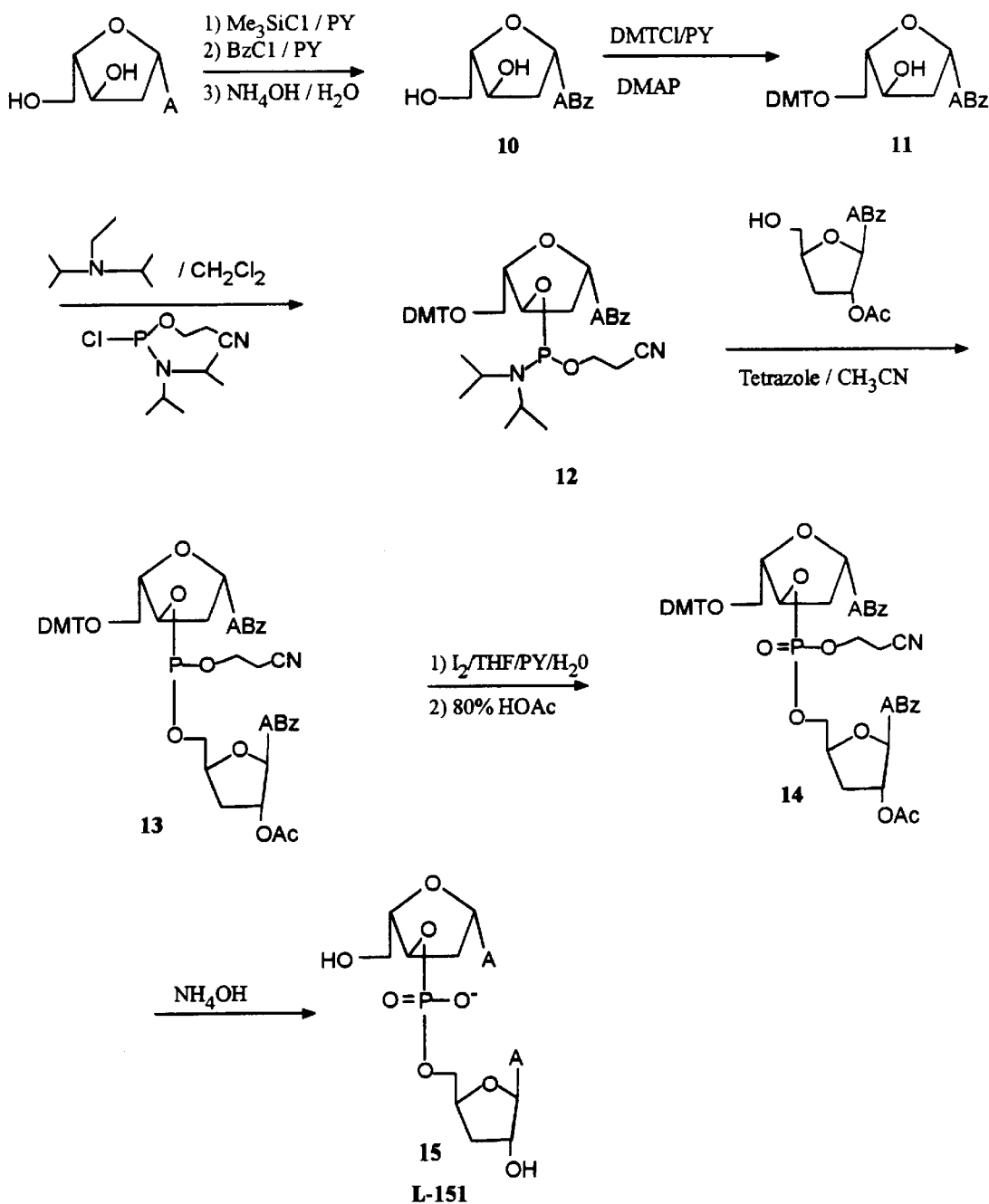
Figure 10:
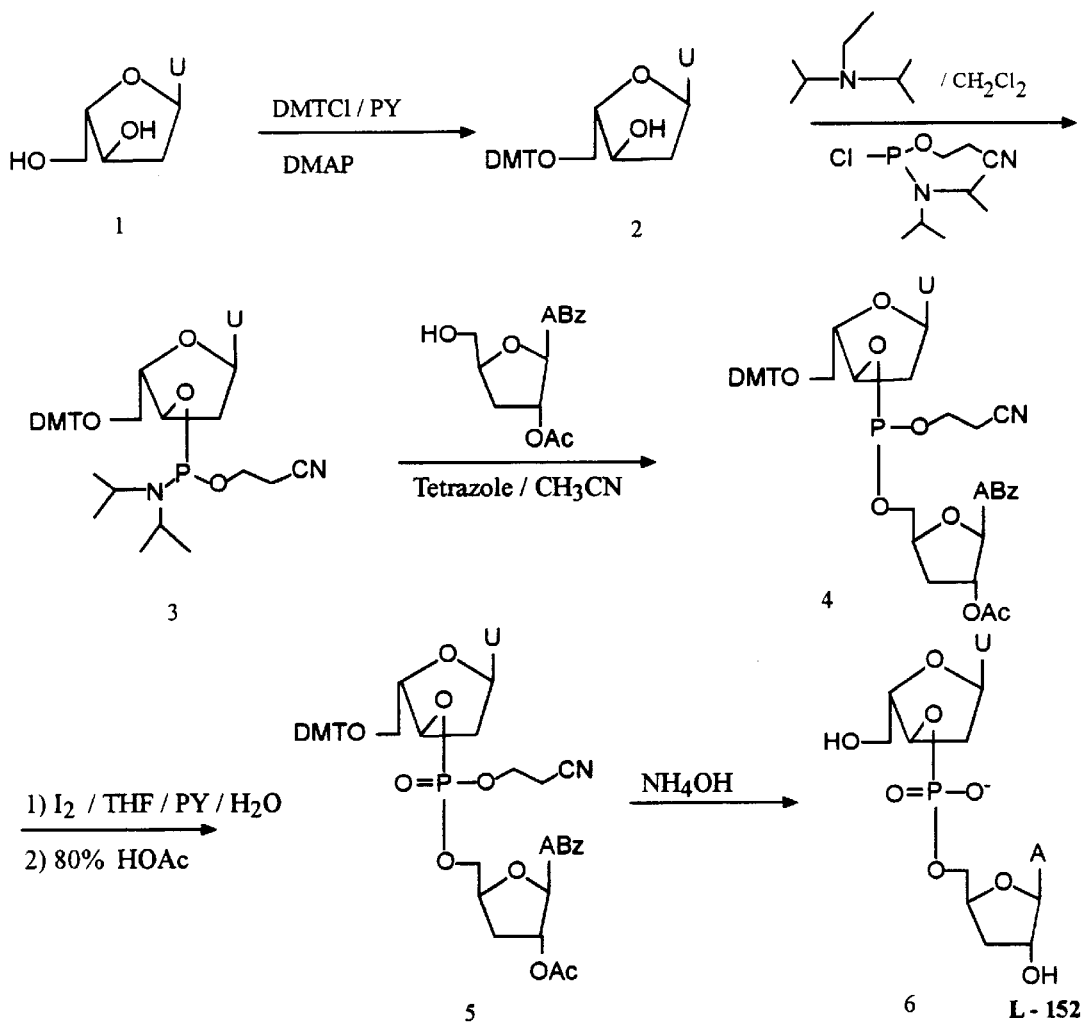
Figure 11:
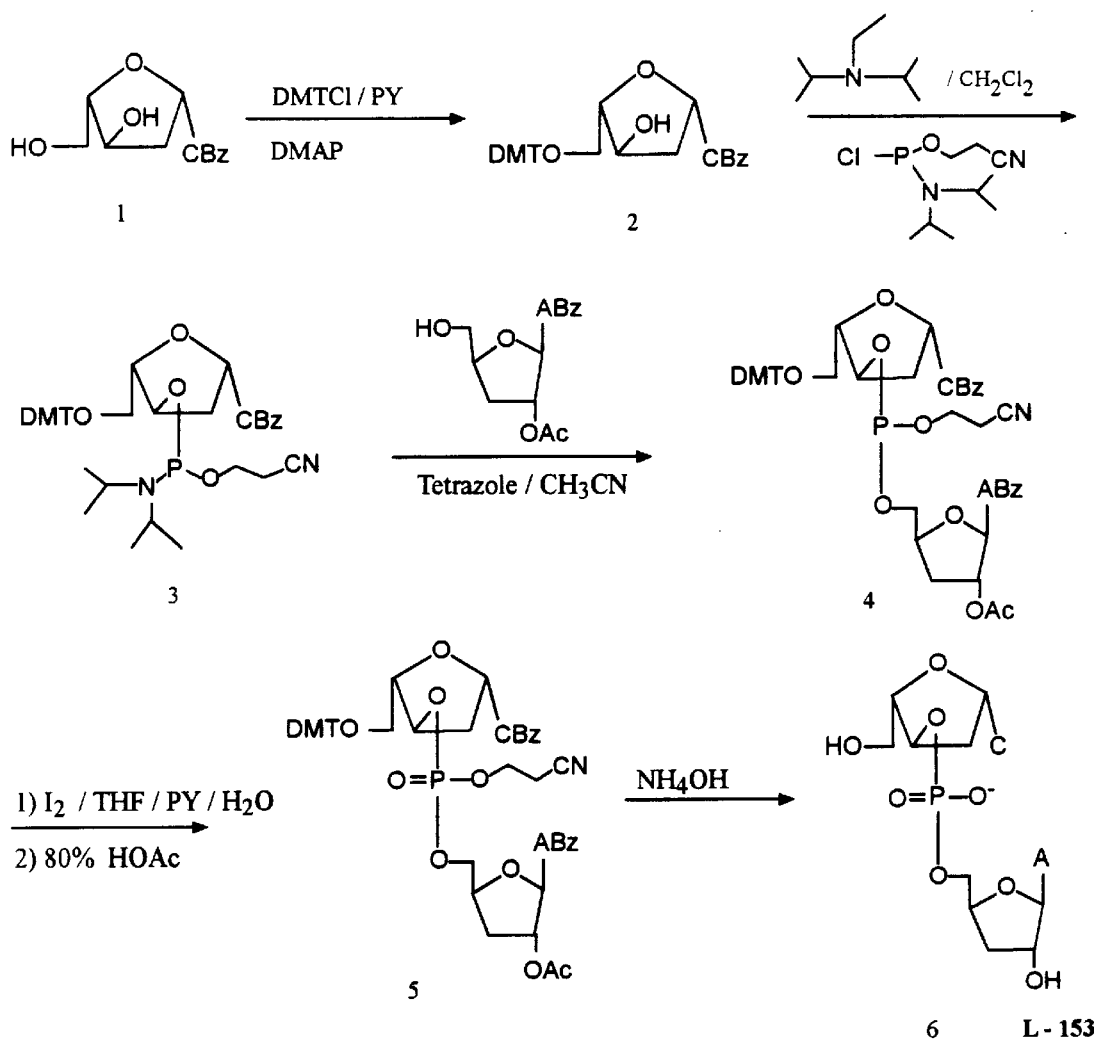
Figure 12:
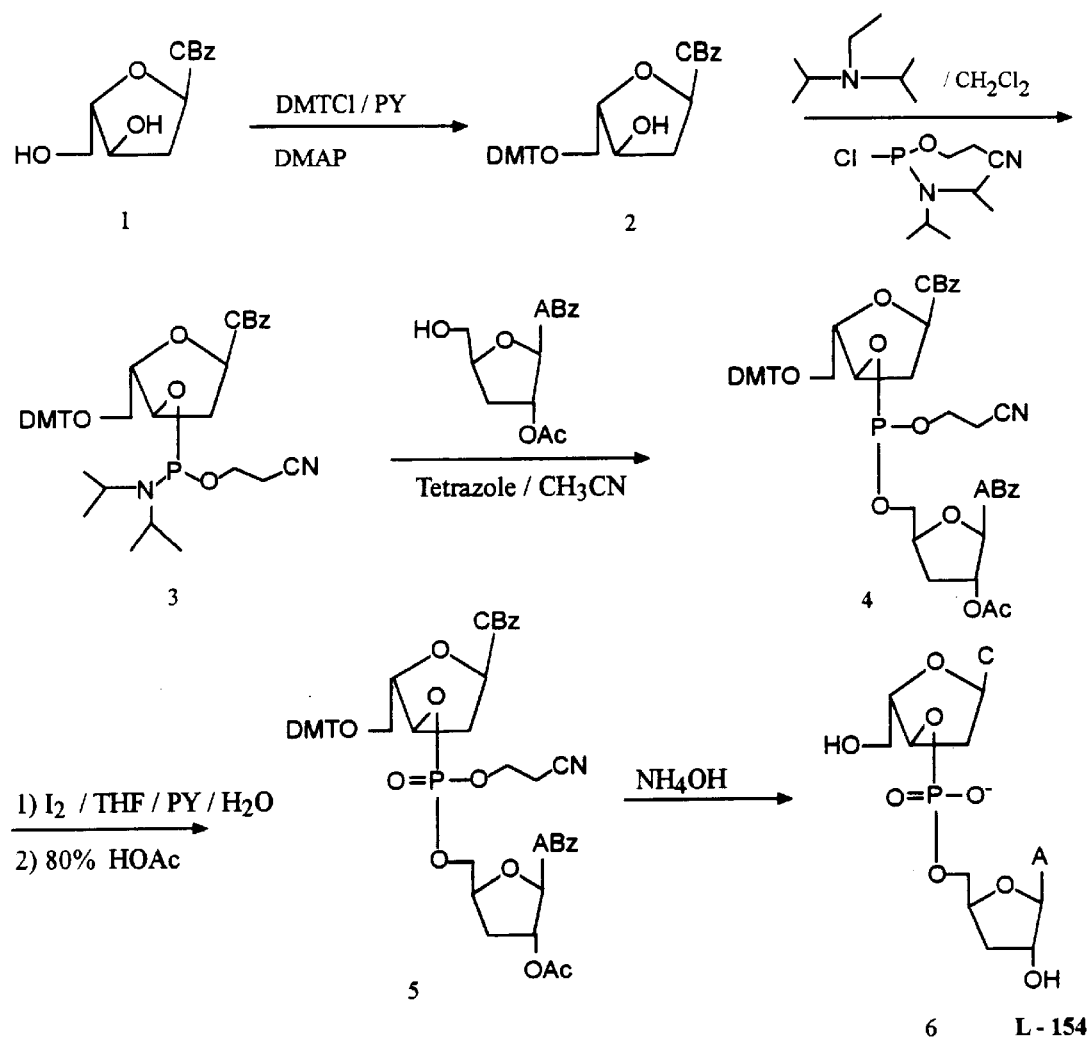
Figure 13:
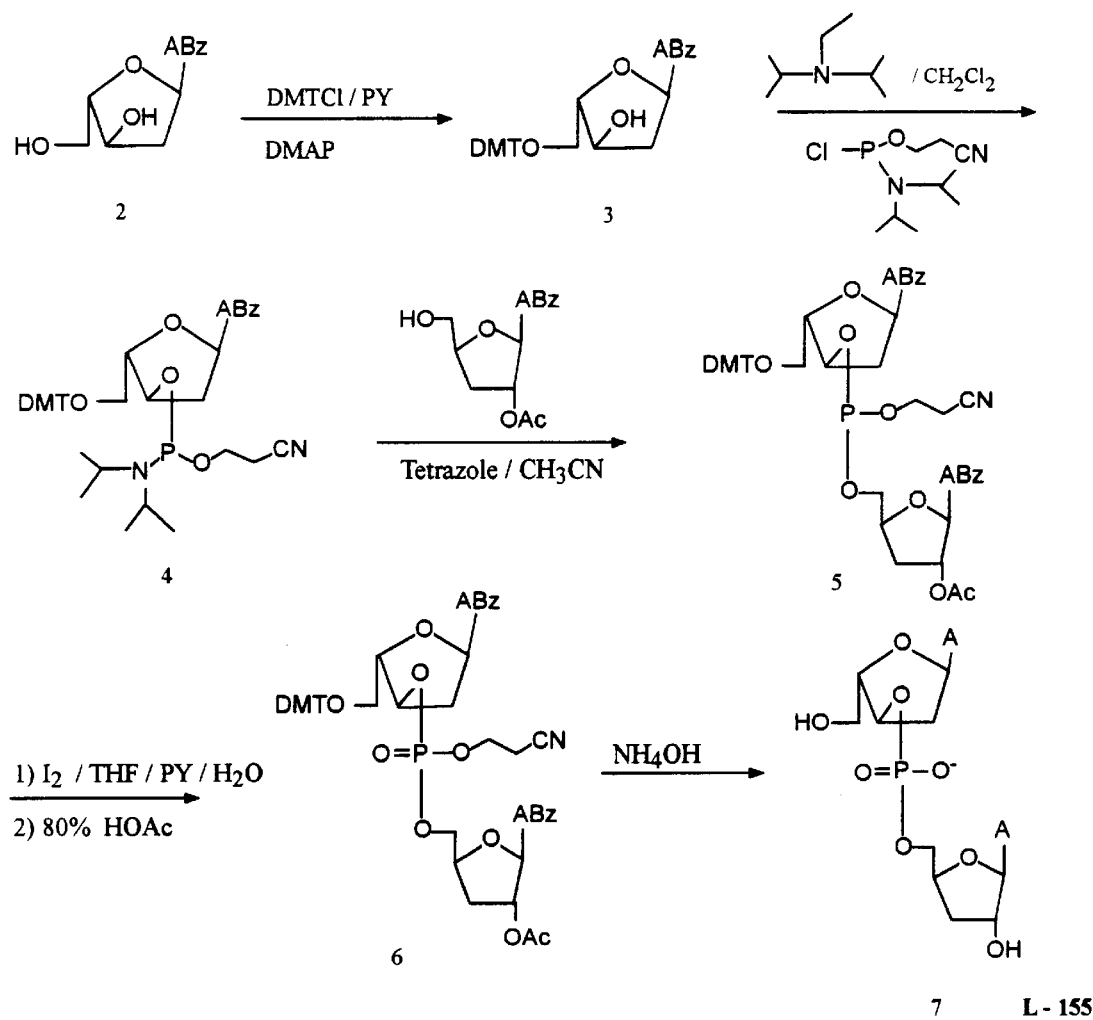

During Phase I research a total of 42 L-nucleoside analogs were screened in an in vitro assay against *P. falciparum*. These compounds are shown in FIG. 7. From these forty-two compounds, 31 were available for screening from Lipitek International's library and 11 were specifically synthesized for the purpose of this project. The detailed synthesis of 11 L-nucleoside conjugates is described in the Methods and Procedures. They were prepared in 100 mg scale and were fully characterized by analytical methods (NMR, HPLC, mass spectra, TLC). The forty-two compounds tested were representative of L-nucleoside monomers or 4 different types of L-nucleosides conjugates. The conjugates tested were: a) dinucleoside phosphates, b) dinucleoside phosphorothioates, c) SATE derivatives of L-nucleosides, and d) L-nucleoside conjugates of nitrobenzylthionosine (NBMPR). It should be emphasized that even more diversification resulted from utilizing characteristic to nucleosides 3' to 5' versus 5'to 3' phosphodiester linkages as well as variations of purines and pyrimidines in both parts of the dimers.

The biological screen involved evaluation of the compounds against the protozoan *P. falciparum* in in vitro culture. The range of drug concentrations was used independently by two assays. One, radiolabelled hypoxanthine incorporation into the nucleic acid of *P. falciparum*, and the other, more expedient assay, a 96-well plate susceptibility assay using lactate dehydrogenase. Both assays gave identical results. In addition, microscopic counting of Giemsa stained thin slides was used as a control. The results of the biological assays are presented in Table 1. Examples of experimental curves are attached as Appendix 2. The biological tests were done at several concentrations. The highest concentration was 200 $\mu$M, the compounds were considered active at concentrations less than 40 $\mu$M.

Discussions

In vitro activity

Figure 14:
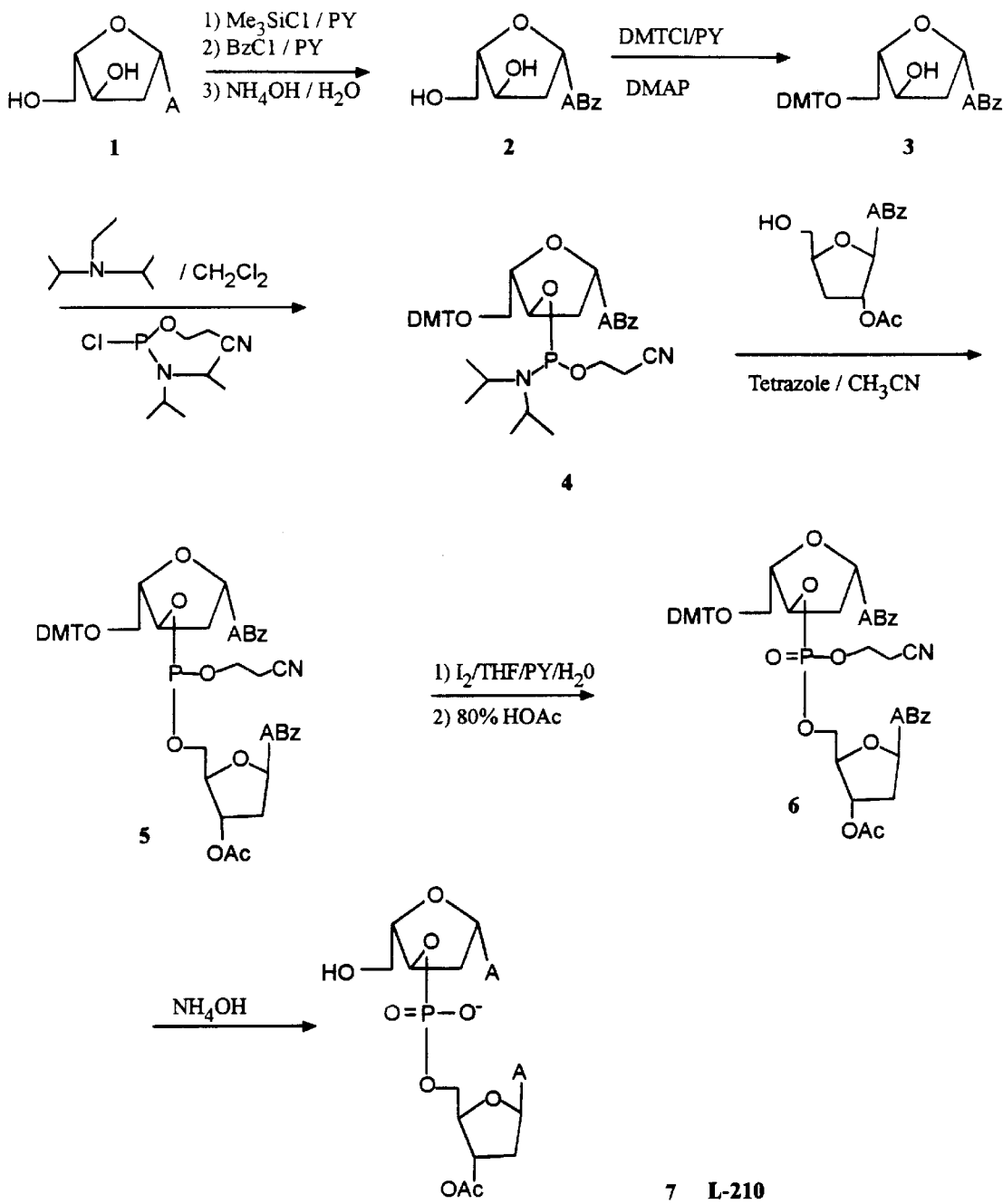
Figure 15A:
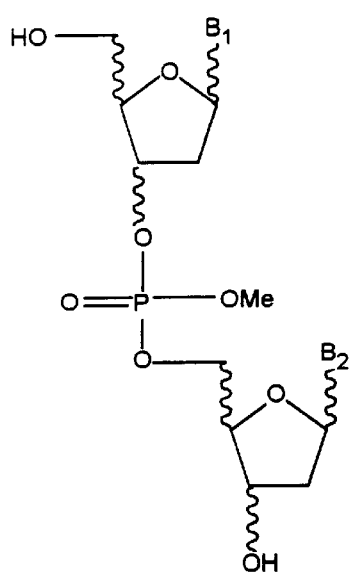
FIGS. 15A and 15B are schematic representations of examples of dinucleoside phosphate dimers containing alternate backbones.
Figure 15A:
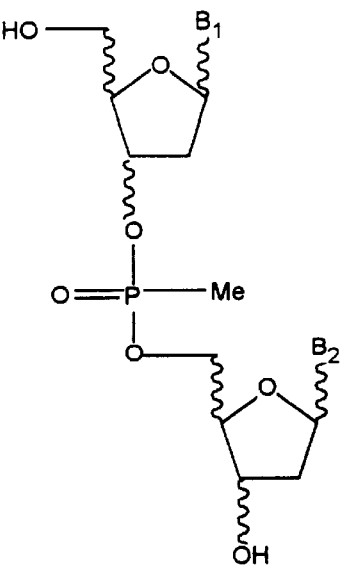
Figure 15A:
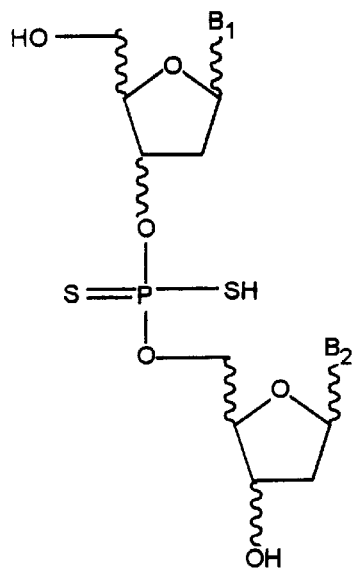
Figure 15A:
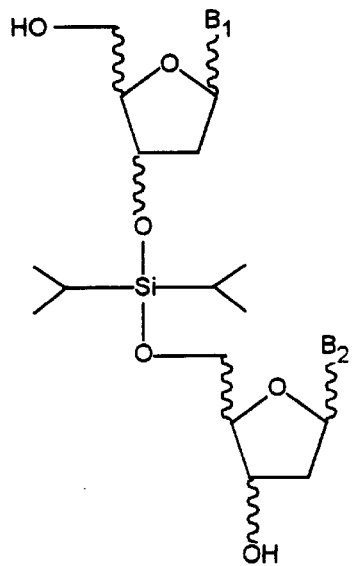
Figure 15B:
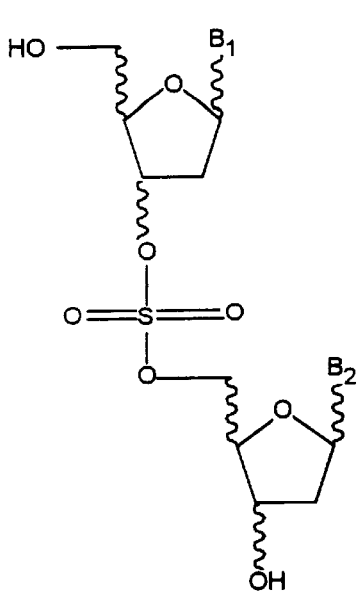
Figure 15B:
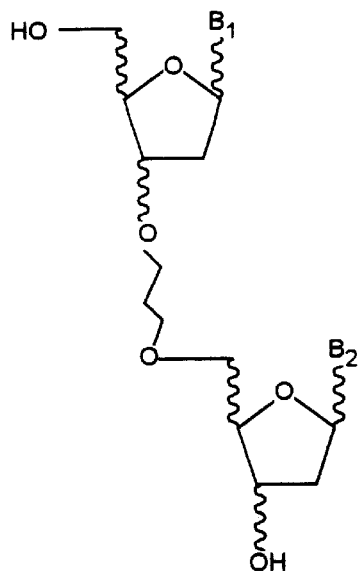
Figure 15B:
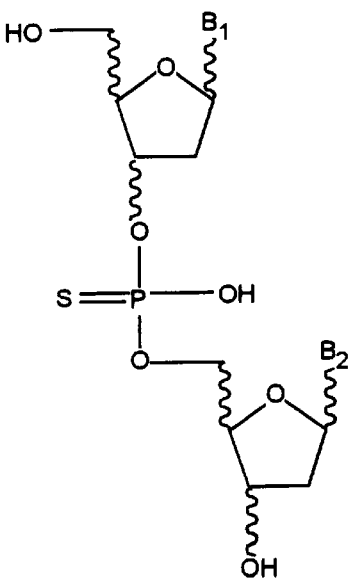
Figure 16A:
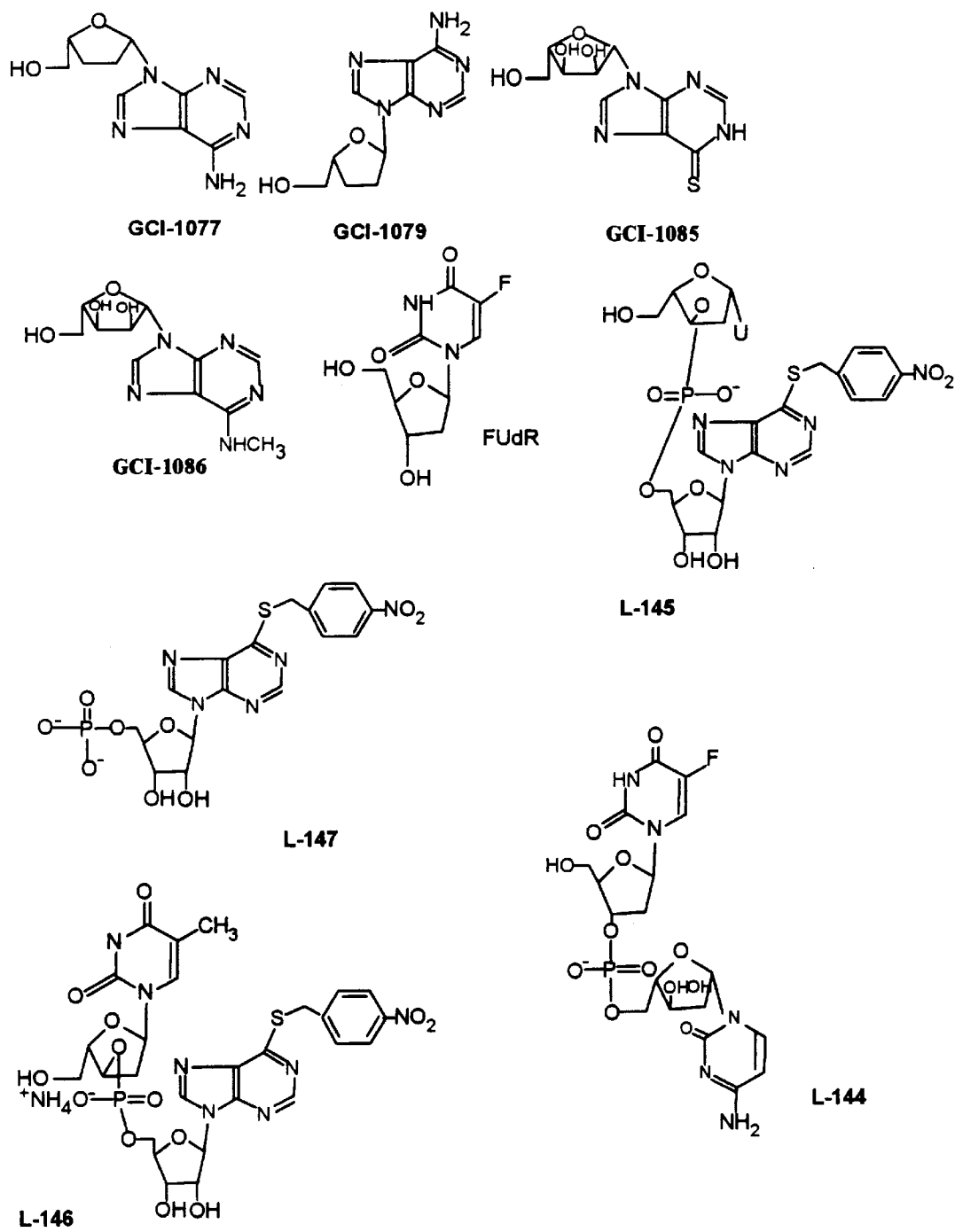
FIGS. 16A–D are schematic representations of dinucleoside phosphate dimers used in the examples.
Figure 16B:
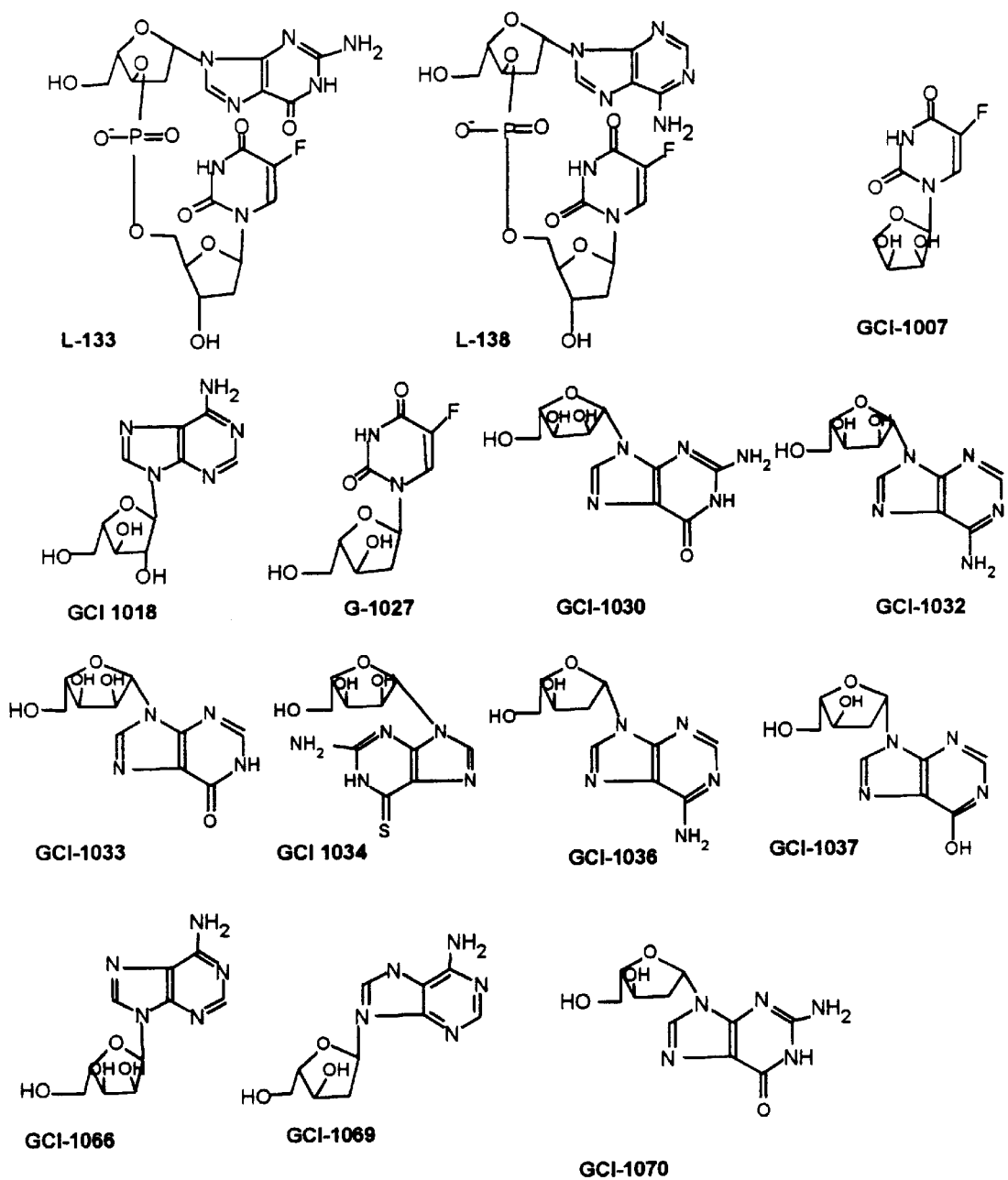
Figure 16C:
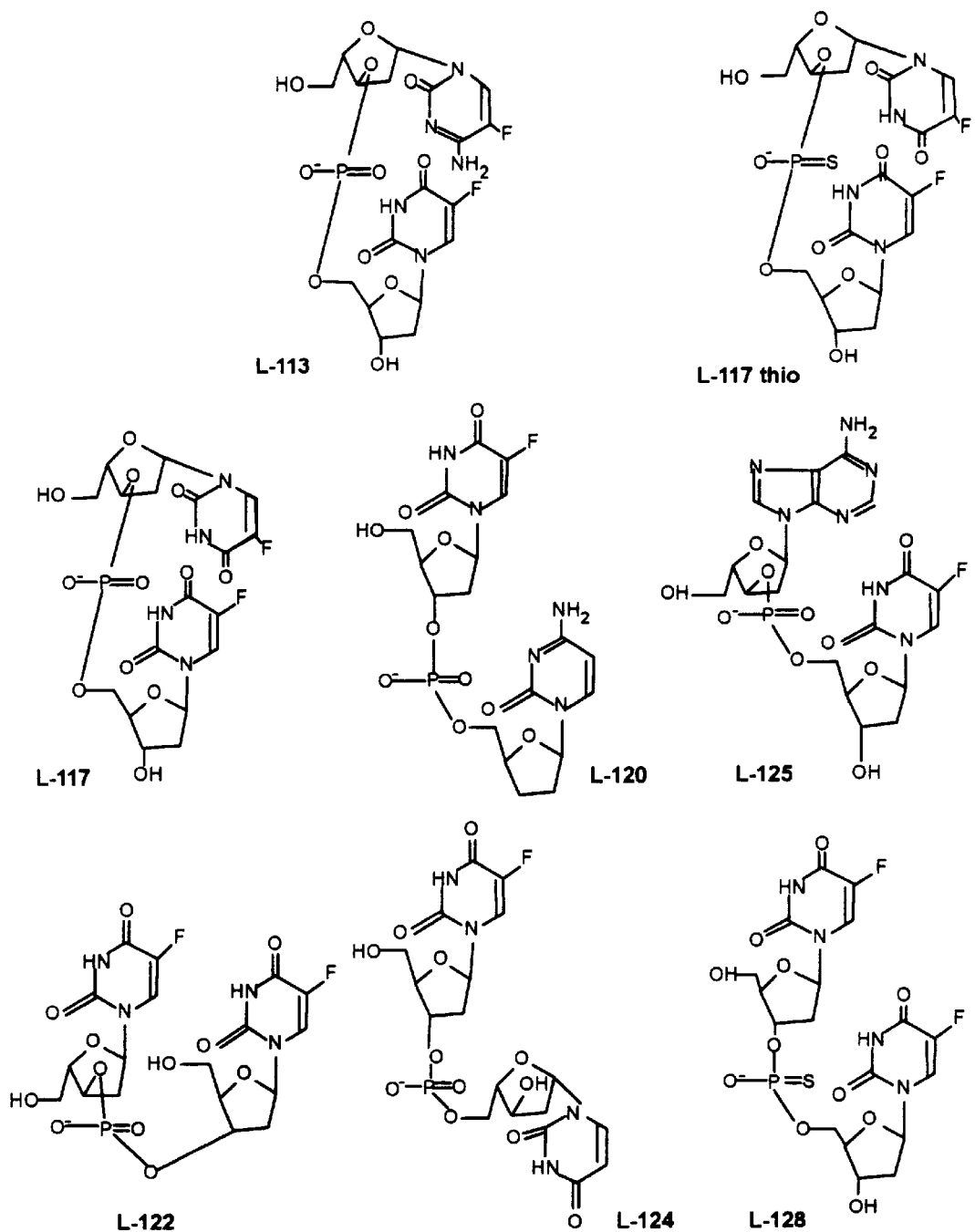
Figure 16D:
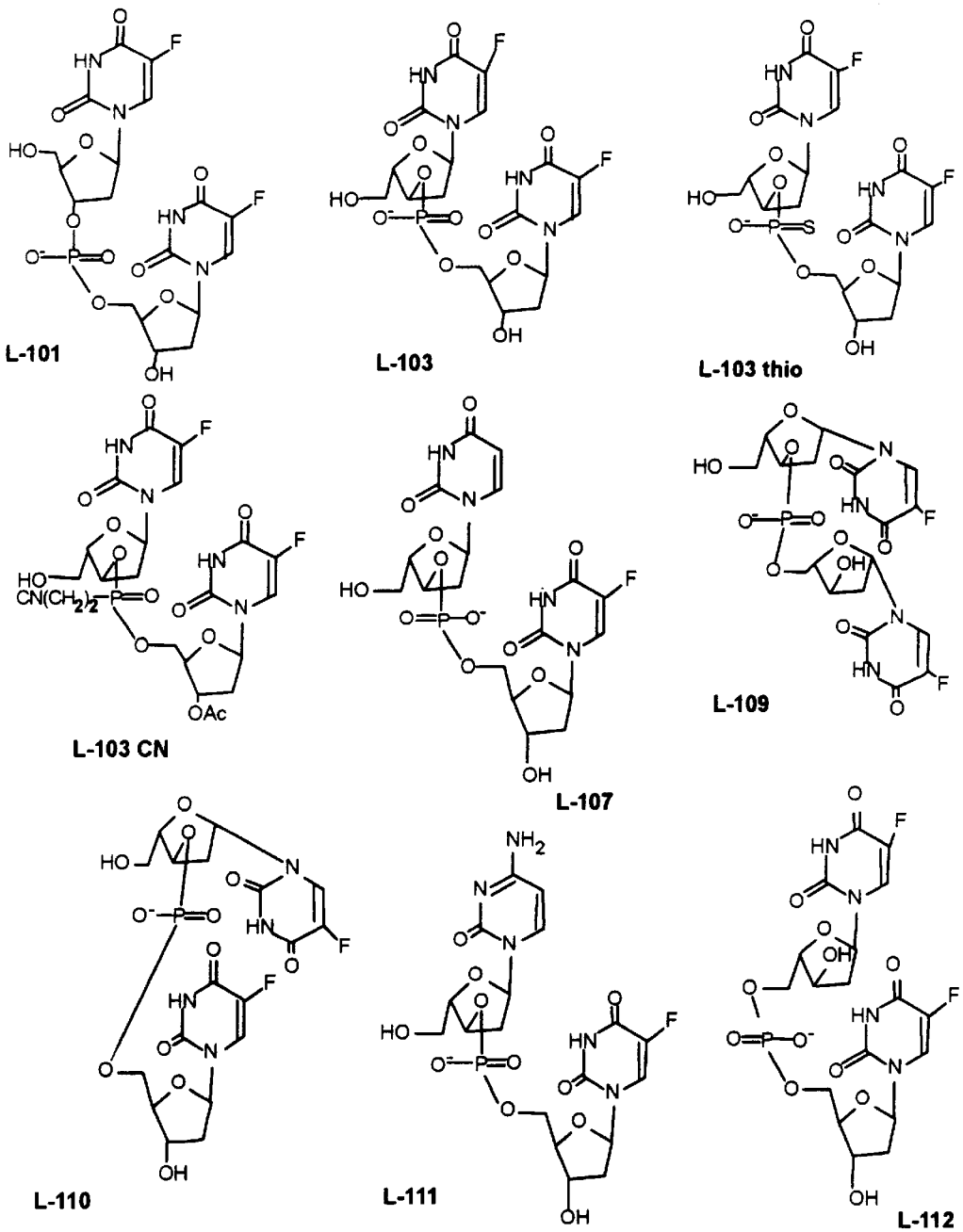
Figure 16E:
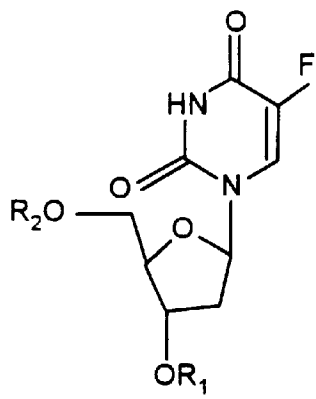
Figure 16E:
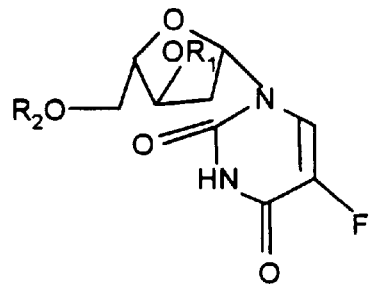
Figure 16E:
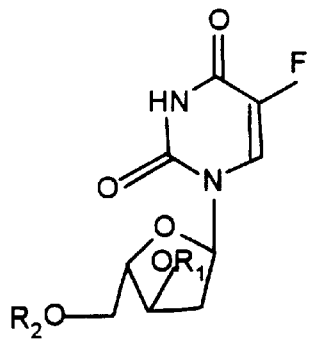
Figure 16E:
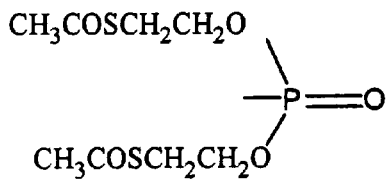

A careful analysis of the data presented in Table 6 (below) indicates that nine (9) analogs from 42 screened had $IC_{50}$ less than 40 $\mu$M (for the structure of the tested compounds see FIG. 14). The most active representative of dinucleoside phosphates were L-101, L-103, L-110, L-111, L-113, L-133 and L-138.

TABLE 1

Results of the in vitro testing.

| N | CODE | COMPOUND | $IC_{50}$, $\mu$M |
|---|---|---|---|
| 1. | L-101 | [β-D]$_2$-FUdR | 15 |
| 2. | L-103 | [α-L,β-D]-FUdR | 20 |
| 3. | L-103 thio | [α-L,β-D]-FUdR, S = P-O | >200 |
| 4. | L-109 | [β-L]$_2$-FUdR | >200 |
| 5. | L-110 | [β-L, β-D]-FUdR | 20 |
| 6. | L-111 | α-L-dC, β-D-FUdR | 38 |
| 7. | L-113 | β-L-dC, β-D-FUdR | 17 |
| 8. | L-117 | β-L-dU, β-D-FUdR | 35 |
| 9. | L-117 thio | β-L-dU, β-D-FUdR S = P-O | >200 |
| 10. | L-125 | α-L-dA, β-D-FUdR | 60 |
| 11. | L-128 | β-D, β-D-FUdR] S = P-O | 1.5 |
| 12. | L-133 | β-L-dG, β-D-FUdR | 14 |

TABLE 1-continued

Results of the in vitro testing.

| N | CODE | COMPOUND | IC$_{50}$, µM |
|---|---|---|---|
| 13. | L-138 | β-L-dA, β-D-FUdR | 5 |
| 14. | L-138-thio | β-L-dA, β-D-FUdR, S = P-O | 100 |
| 15. | L-144 | β-D-FUdR, β-L-A | 140 |
| 16. | L-145 | β-L-dU, NBMPR | >200 |
| 17. | L-146 | α-L-dT, NBMPR | >200 |
| 18. | L-147 | NBMPR, MP | Solubility problem |
| 19. | NBMPR | NBMPR | 100 |
| 20. | GCI 1007 | α-L-erythrofuranosyl-5-fluorouracil | >200 |
| 21. | GCI 1018 | α-L-arabinofuranosyl adenine | >200 |
| 22. | GCI 1027 | α-L-FUdR | >200 |
| 23. | GCI 1030 | β-L-G | >200 |
| 24. | GCI 1032 | β-L-A | >200 |
| 25. | GCI 1033 | β-L-I | >200 |
| 26. | GCI 1034 | β-L-mercapto-G | >200 |
| 27. | GCI 1036 | β-L-Da | >200 |
| 28. | GCI 1037 | β-L-dI | >200 |
| 29. | GCI 1066 | α-L-A | >200 |
| 30. | GCI 1069 | α-L-dA | >200 |
| 31. | GCI 1070 | β-L-dG | >200 |
| 32. | GCI 1077 | β-L-ddA | >200 |
| 33. | GCI 1079 | α-L-ddA | >200 |
| 34. | GCI 1085 | N$^6$-methyl-β-L-A | >200 |
| 35. | GCI 1076 | 6-thio-β-L-purine | >200 |
| 36. | B01 | β-D-FUdR 3'SATE | 100 |
| 37. | B02 | β-D-FUdR 5'SATE | 60 |
| 38. | B03 | β-D-FUdR 3'-5'SATE | 6 |
| 39. | B04 | β-L-FUdR 5'SATE | 200 |
| 40. | B05 | β-L-FUdR 3'-5'SATE | Solubility problem |
| 41. | B06 | α-L-FUdR 5'SATE | 150 |
| 42. | B07 | α-L-FUdR 3'-5'SATE | Solubility problem |

The 14 L-nucleoside monomers in α- and β- forms and even α-L-FUdR showed no activity against *P. falciparum*. Because of that, further research on monomers was halted (see Table 1).

The dimer containing only the "non-natural" isomeric form of nucleoside (L-109) did not exhibit any activity.

Careful analysis of the data in Table 1 indicates that β-D-isomer of FUdR is the active component of the dimer molecules. The position of the active component in the dimer is important. The β-D-FUdR needs to be connected to the 3'-OH end of the L-nucleoside through a phosphodiester linkage to its 5-OH. Compounds which are linked through 3'-OH of FUdR are much less active (see Table 2). This indicates that the substitution pattern of β-D-FUdR is critical for the activity of the dimers and most probably the mechanism involves thymidylate synthase inhibition. It is well known that TS inhibitors of FUdR have very rigid structural requirements and is do not allow for any substitution at the 3' end.

TABLE 2

The activity of the L-nucleoside containing dimers versus position of FUdR linkage

| 5' | | 3' | |
|---|---|---|---|
| Compound | IC$_{50}$, µM | Compound | IC$_{50}$, µM |
| L-101 ([β-D]$_2$-FUdR) | 15 | L-144 (β-D-FUdR, β-L-A) | 140 |
| L-103 (α-L-FJdR, β-D-FUdR) | 20 | | |
| L-110 (β-L-FUdR, β-D-FUdR) | 20 | | |
| L-111 (α-L-dC, β-D-FUdR) | 38 | | |

TABLE 2-continued

The activity of the L-nucleoside containing dimers versus position of FUdR linkage

| 5' | | 3' | |
|---|---|---|---|
| Compound | IC$_{50}$, µM | Compound | IC$_{50}$, µM |
| L-113 (β-L-dC, β-D-FUdR) | 17 | | |
| L-125 (α-L-dA, β-D-FUdR) | 60 | | |
| L-133 (β-L-dC, β-D-FUdR) | 14 | | |
| L-138 (β-L-dA, β-D-FUdR) | 5 | | |

In the case of purine nucleoside, the attachment of the α-L nucleoside to β-D-FUdR monomer reduces the dimer activity in comparison with dimers containing the β-L unit (see Table 3, L-125 and L-138). In the case of pyrimidine nucleosides there is no obvious difference in the activity (L-103 & L-110, L-111 & L-113).

TABLE 3

The activity of the dimers versus chemical configuration of the; L-nucleoside

| α-L | | β-L | |
|---|---|---|---|
| Compound | IC$_{50}$, µM | Compound | IC$_{50}$, µM |
| L-103 (µ-L-FUdR) | 20 | L-110 (β-L-FUdR) | 20 |
| L-111 (α-L-dC) | 38 | L-113 (β-L-dC) | 17 |
| L-125 (α-L-dA) | 60 | L-138 (β-L-dA) | 5 |

The different activity of the dimers is dependent on the structure of the second nucleoside.

The data presented above suggest that the following plausible pathways for metabolic activation and/or mode of action of the dimer molecules tested:

(1) Dimer may act as a new chemical entity without hydrolysis of the phosphate or pro-phosphate bond between the two monomeric units;

(2) Hydrolysis to L-nucleoside and FUdR nucleotide may occur, in which case the dimer is a prodrug. The L-nucleoside is used for protection and to increase the bioavailability of β-D-FUdR monophosphate.

It is also important to note that hydrolysis can take place intracellularly as well as outside the cell.

In the last decade, monumental efforts have been directed toward the synthesis of oligonucleotide analogs with altered phosphodiester linkage. The goal was to improve the stability of duplex and triplex formation, to improve the cellular uptake and to decrease the rate of degradation of oligonucleotides by endo and exo nucleases which cleave the phosphodiester linkage. We selected one such chemical modification for our study. As a consequence, several dimers with phosphorothioate linkage between two nucleosides were synthesized and tested. The phosphorothioate comprises a sulfur-for-oxygen substitution at phosphorus of the phosphodiester linkage (for the structure of the corresponding dimers see Appendix 1). It has been shown (M. Matsukura, K. Shinozuka, G. Zon, H. Mitsuya, M. Reitz, J. S. Cohen, L. M. Neckers, Proc. Natl. Acad. Sci. USA. 84, 7706 (1987)) that the S homologues are more resistant to cellular nucleases and are readily taken up by cells. Several oligonucleotides of this type are currently in clinical studies (ISIS Pharmaceuticals and others).

TABLE 4

The activity of the dimers versus nature of the linkage between two nucleosides analogs

| Phosphate "bridge" O=P—O | IC$_{50}$, µM | Phosphorothioate "bridge" S=P—O | IC$_{50}$, µM |
|---|---|---|---|
| L-101 ([β-D]$_2$-FUdR) | 15 | L-128 ([β-D]$_2$-FUdR) | 1.5 |
| L-103 ([α-L,β-D]-FUdR) | 20 | L-103 ([α-L,β-D]-FUdR) | >200 |
| L-117 (β-L-dU, β-D-FUdR) | 35 | L-117 (β-L-dU, βD-FUdR) | >200 |
| L-138 (β-L-da, β-D-FUdR) | 5 | L-138 (β-L-dA, β-D-FUdR) | 100 |

The replacement of the phosphate linkage by the phosphorothioate bond in the dimer, containing two β-D-FUdR units, increases the activity of the compounds by a factor of 10 (see Table 4, data for L-101 & L-128). The only active phosphorothioate analog appears to be compound L-128. The activity of L-128 is greater in comparison with all possible products of hydrolysis (see Table 4). Moreover, L-128 was the most active compound tested.

TABLE 5

The activity of β-D-FUdR and some possible products of its metabolism

| COMPOUND | IC$_{50}$, µM |
|---|---|
| β-D-FUdR | 34 |
| β-D-5'-FUdRmP | 50 |
| 5FUracil | 6 |

The introduction of the phosphorothioate bond into molecules of dimers containing "non-natural" nucleoside isomer was not successful: the activity of the compounds was reduced dramatically (see Table 4, data for L-103, L-117 & L-138). As was discussed before, one of the possible mechanisms of dimer action is the participation in the metabolic pathways of the whole non-hydrolyzed molecule. In this case the increasing of the dimer stability by the introduction of the phosphorothioate linkage results in the increasing of the activity of L-101. For the dimers containing the "non-natural" isomeric modification of the nucleoside the metabolism of whole non-hydrolyzed molecule is probably impossible.

It is well established that most of the nucleoside analogs are dependent in kinase-mediated activation to generate the bioactive nucleotide and ultimately, the nucleoside triphosphate (C. Periqaud, G. Gosselin, J. L. Imbach, Nucleoside Nucleotides. 11, 903 (1992)). Activation takes place in the cytosol after nucleoside uptake and involves three successive viral and/or cellar kinases, the first one being highly specific (M. C. Starnes, Y. C. Cheng, J. Biol. Chem. 262, 988 (1987)). One possibility to improve the efficiency of the nucleoside analog is a therapeutic agent could be to bypass the phosphorylation step. Unfortunately, nucleoside monophosphates themselves, due to their polar nature, are not able to cross the cell membrane efficiently (K. C. Leibman, C. J. Heidelberg, J. Biol. Chem. 216, 823 (1995)). Hence the idea of temporarily masking or reducing the phosphate negative charges with neutral substituents, thereby forming more lipophilic derivatives which would be expected to revert back to the nucleoside mono-phosphate once inside the cell.

One of the possible structural modifications for the kinase bypass is the use of the bis-S-acetylthioethyl (SATE) derivatives pioneered by J.-L. Imbach (I. Lefebvre, C. Perigaud, A. Pompon, A. M. Auberth, J. L. Grardet, A. Kirn, G. Gosselin and J. L. Imbach, J. Med. Chem. 38, 3941–3950 (1995); C. Perigaud, G. Gosselin, I. Lefebvre, J. L. Girardet, S. Benzaria, I. Barber and J. L. Imbach, Bio. Org. Med. Chem. Lett. 3, 2521–2526 (1993)). Several SATE derivatives of FUdR isomers were synthesized and tested their in vitro activity against P. falciparum. The obtained results are listed in Table 6.

TABLE 6

The activity of the SATE derivatives of FUdR

| Compound | ID$_{50}$, µM |
|---|---|
| β-D-FUdR | 34 |
| β-D-FUdR monophosphate | 50 |
| B01 (β-D-FUdR 3' SATE) | 100 |
| B02 (β-D-FUdR 5' SATE) | 60 |
| B03 (β-D-FUdR 3',5' SATE) | 6 |
| β-L-FUdR | >200 |
| β-L-FUdR monophosphate | N/A |
| B04 (β-L-FUdR 5' SATE) | 200 |
| B05 (β-L-FUdR 3',5' SATE) | Solubility problem |
| α-L-FUdR | >200 |
| α-L-FUdR monophosphate | N/A |
| B06 (α-L-FUdR 5' SATE) | 150 |
| B07 (α-L-FUdR 3',5' SATE) | Solubility problem |

It should be emphasized that all of the SATE derivitization was performed on monomers of FUdR varying the conformation. Thus derivatives of α- and β D and L-FUdR were prepared. Three types of SATE analogs were produced, a) decorated at 5' of the nucleoside, b) decorated at 3' of the nucleoside, and c) decorated at both 3' and 5' of the nucleoside resulting in disubstitution.

Fifteen L-nucleoside dimers (L-101, L-103, L-103A, L-107, L-110, L-111, L-112, L-114, L-117, L-120, L-122, L-124, L-125, L-133 & L-138) from Lipitek's library were submitted for in vitro screen to the U.S. Army Antimalarial Test Program (for the structures of the compounds, see FIG. 7). The compounds have been tested for their activity against two P. falciparum strains: D6 (chloroquin non-resistant) and W2 (chloroquin resistant). Seven (7) of the tested compounds exhibited activities below 40 µM against both strains of P. falciparum. The most active dimers were L-101, L-110, L-112, L-117, L-133 & L-138.

The transport and metabolism study

It has been established that transport and uptake in parasite invaded cells is different from that of normal blood erythrocytes (A. M. Gero & A. M. Wood, In: Pyrine & Pyrimidine Methabolism in Man VII, Part A. (R. A. Harkness et al., Eds) Plenum Press, NY, 169–172 (1991)). Invasion by the malaria parasite comprises the cell membrane, allowing penetration of unnatural substances of various size and shape, whereas normal cells are very selective in uptake. It was shown that L-nucleosides and their derivatives easily penetrate invaded cells, while they have a very slow rate of uptake into normal cells, if they enter at all. In order to obtain preliminary data on transport, uptake and metabolism, the HPLC method was used to analyze the following 10 Lipitek compounds: L-101, L-103, L-109, L-111, L-117, L-133, L-138, GCl 1007, GCl 1027, GCl 1069.

HPLC retention times for standard compounds purchased from Sigma is presented in Table 7.

TABLE 7

HPLC Retention Time for the Standard Compounds

| Compound | R.t., min |
|---|---|
| Nucleobase | |
| Adenine | 4.93 |
| Guanine | 5.38 |
| Uracil | 4.37 |
| Hypoxanthine | 5.59 |
| Nucleoside | |
| Adenosine | 12.47 |
| Guanosine | 9.96 |
| Inosine | 8.88 |
| Thymidine | 12.36 |
| 2'-Deoxyadenosine | 12.29 |
| 2'-Deoxyguanosine | 11.03 |
| 2'-Deoxyuridine | 7.41 |
| 2'-Deoxycytidine | 8.25 |
| FUdR | 10.21 |
| Nucleotide | |
| 5'AMP | 16.56 |
| 3'AMP | 19.46 |
| 5'ADP | 23.89 |
| 5'-ATP | 30.09 |
| 5'GMP | 15.24 |
| 5'-GDP | 23.13 |
| 5'GTP | 29.01 |
| 5'-UMP | 14.85 |
| FUdRMP | 16.40 |

These compounds were chosen for the identification of possible metabolites. In this experiment the compounds were incubated with both whole infected cells, and with whole and lysed uninfected cells, followed by the separation of unreacted compound and HPLC analysis.

The results are presented in Table 8:

Column 1 shows the retention times of the original compound (not incubated with any cells).

Column 2 shows the retention times of the original compound remaining after incubation with whole parasite infected cell.

Column 3 shows the metabolic products i.e. new peaks due to conversion of the original compound or alteration in the natural purine or pyrimidine profile of the infected cell.

TABLE 8

HPLC Retention Time of Lipitek's Compounds (Trophozoite Incubations)

| Compound | Neat Injection | Unmetabolized Peak | Metabolic Product |
|---|---|---|---|
| L-138 | 18.17, 18.89 | 18.26 | 16.93, 15.73 |
| L-133 | 16.72 | 17.03 | 15.65 |
| L-101 | 19.05 | 19.01 | 10.62 |
| L-103 | 18.31 | 18.25 | — |
| L-117 | 17.41 | 17.61 | — |
| L-111 | 15.69 | 15.69 | — |
| L-109 | 16.36 | — | — |
| GCI 1027 | 10.21 | 10.61 | — |
| GCI 1007 | 12.61 | 12.42 | — |
| GCI 1069 | 12.29 | — | 9.65 |

All nucleosides monophosphate dimers containing β-D-FUdR unit in combination with any L-nucleosides (L-101, L-103, L-111, L-117, L-133, and L-138) as well as tested L-nucleoside monomer analogs (GCl 1007, GCl 1027 & GCl 1069) entered the infected cells. All these compounds were toxic against *P. falciparum*. The L-109, combination of two L-dimers, could not enter the infected cell, and was also not toxic.

Compounds L-101, L-133 & L-138 appear to be metabolized by the infected cells, each producing at least one new peak (see Table 8). It is possible that L-138 and L-133 may be cleaved to a nucleotide and nucleoside.

None of the above 10 compounds were found to enter normal erythrocyte. Metabolism of any of the above compounds did not occur in lysates of human erythrocytes or lymphocytes. So even if the compounds were able to get into the normal cells, the normal cells cannot metabolize them into active ingredients. This underscores again the low toxicity and the selectivity of the L-nucleoside conjugates disclosed and claimed in this Application.

EXAMPLE 6

Synthesis of $N^6$-Benzoyl-3'-deoxy-β-D-adenosine

To a stirring solution of 3'-deoxyadenosine (2.0 g, 7.96 mmol) in pyridine (80 ml) chilled in an ice bath, $ClSiMe_3$ (5.0 ml, 39.8 mmol) was added dropwise and stirred for 30 minutes. Benzoyl chloride (3.7 ml, 31.84 mmol) was then added dropwise and the reaction mixture was stirred at room temperature for two hours. This was cooled in an ice bath and water (16 ml) was added dropwise. 15 minutes later concentrated $NH_4OH$ (16 ml) was added to give a solution approximately 2M in ammonia. After 30 minutes the solvent was evaporated and the residue was dissolved in water and washed with ether. The water layer was concentrated and the compound was crystallized from water as white solid (2.32 g. 82%).

EXAMPLE 7

Synthesis of $N^6$-Benzoyl-5'-O-(di p-methoxytrityl)-3'-deoxy-β-D-adenosine

To a solution of compound $N^6$-Benzoyl-3'-deoxy-β-D-adenosine 1(2.32 g, 6.53 mmol) in pyridine (100 ml) was added 4,4'-dimethoxytrityl chloride (3.32 g, 9.79 mmol) and DMAP (0.24 g, 1.96 mmol) and stirred at room temperature for 2 hours under argon. To complete the reaction, additional DMTCl (0.5 g) was added and stirred for another 2 hours. The reaction was quenched with the addition of MeOH (5 ml) and the solvent was evaporated. The residue was dissolved in EtOAc, washed with water, $NaHCO_3$ and brine. After drying over $Na_2SO_4$, the EtOAc layer was evaporated and the crude compound was purified on a silica gel column using 80% $EtOAc/CHCl_3$ as solvent to give pure compound 2 (4.33 g, 83%) as a white foam.

EXAMPLE 8

Synthesis of $N^6$-Benzoyl-2'-O-acetoxy-β-D-3'-deoxyadenosine

To a solution of $N^6$-Benzoyl-5'-O-(di p-methoxytrityl)-3'-deoxy-p-D-adenosine (4.3 g, 6.58 mmol) in pyridine (100 ml) acetic anhydride (1 ml, 9.87 mmol), and DMAP (0.08 g, 0.65 mmol) was added and stirred at room temperature for 15 minutes. Then the solvent was evaporated and the residue was dissolved in EtOAc, washed with water, $NaHCO_3$, brine and dried over $NA_2SO_4$. After the evaporation of EtOAc, then the crude material was dissolved in 80% AcOH (50 ml) and stirred at room temperature for one hour. Then the solvent was evaporated and coevaporated with tolune and purified on a silica gel column using 3–5% $MeOH/CHCl_3$ to give pure $N^6$-Benzoyl-2'-O-acetoxy-β-D-3-deoxyadenosine (2.11 g, 81%) as a foam.

EXAMPLE 9

Synthesis of β-L -dU, Cordycepin dimer (L-150)

β-L-dU (1.0 g, 4.38 mmol) was dissolved in dry pyridine (50 ml), to this solution was added 4,4'-dimethoxytrityl chloride (1.78 g, 5.25 mmol) and DMAP (0.1 g, 0.87 mmol). This was stirred under argon at room temperature for 2 hours and quenched with MeOH (5 ml). The solvent was evaporated, the residue was dissolved in EtOAc, washed with water, NaHCO$_3$ and brine. After drying and evaporation of the solvent, the crude material was purified on a silica gel column using 60–80% EtOAc/CHCl$_3$ as solvent to give pure 5'-O Dimethoxytrityl-β-L-2'-deoxyuridine (2.2 g, 94.8%) as white foam.

Dimethoxytrityl-β-L-2'-deoxyuridine (1.5 g, 2.83 mmol) was dissolved in anhydrous dichloromethane (50 ml). N,N-diisopropylethylamine (2.0 ml, 11.3 mmol) was added uner argon followed by 2'-cyanoethyl-N,N-diisopropylchlorophosphoramidite (0.82 ml, 3.68 mmol). The reaction was stirred for 30 minutes and the solvent was evaporated. The residue was dissolved in 80% EtOAc/Et$_3$N (75 ml) and washed with water, NaHCO$_3$ and brine. The organic layer was evaporated and purified on a short silica gel column using a mixture of EtOAc, CH$_2$Cl$_2$ and ET$_3$N (40:50:10) to give 5'-O-Dimethoxytrityl-β-L-2'-deoxyuridine-3'-N,N-diisopropylcyanoethyl phosphoramidite in quantitative yield.

To a solution of compound 5'-O-Dimethoxytrityl-β-L-2'-deoxyuridine-3'-N,N-diisopropylcyanoethyl phosphoramidite (2.83 mmol) in anhydrous acetonitrile (60 ml), N$^6$-Benzoyl-2'-O-acetoxy-β-D-3-deoxyadenosine (1.12 g, 2.83 mmol) in acetonitrile (40 ml) was added and stirred for 10 minutes under argon. To this solution, sublimed 1H-tetrazole (0.6 g, 8.5 mmol) was added and stirred over night. The solvent was evaporated and the residue was triturated with 70% EtOAc/ether and filtered. The filtrate was evaporated to give 5'-O-Dimethoxytrityl-3'-[O-(2'-O-acetyl)-N$^6$-benzoyl-β-D-3'-deoxy adenosinyl]-2'-deoxy-β-L-uridine cyanoethyl phosphite ester as a foam and this was used in the next step without further purification.

The 5'-O-Dimethoxytrityl-3'-[O-(2'-O-acetyl)-N$^6$-benzoyl-β-D-3'-deoxy adenosinyl]-2'-deoxy-β-L-uridine cyanoethyl phosphite ester was dissolved in THF (24 ml), pyridine (6 ml) and water (0.6 ml). Iodine crystals (1.0 g) were added portion wise until the iodine color persists. The reaction mixture was stirred for another 15 minutes and the excess iodine was removed by the addition of saturated sodium thiosulfate. The solvent was evaporated and the residue was dissolved in EtOAc and washed with water, NaHCO$_3$ and brine. EtOAc layer was evaporated and the residue was dissolved in 80% acetic acid/water solution (40 ml) and stirred for 1 hour. Then the solvent was evaporated and the crude product was purified on a silica gel column using 8–15% MeOH/CHCl$_3$ as solvent to give pure (2'-Acetoxy-N$^6$-benzoyl-3'-deoxy-β-D-adenosinyl)-β-L-2'-deoxyuridinyl cyanoethyl phosphate ester (0.75 g) as a foam.

The dimer (2'-Acetoxy-N$^6$-benzoyl-3'-deoxy-β-D-adenosinyl)-β-L-2'-deoxyuridinyl cyanoethyl phosphate ester (0.75 g) was treated with ammoniun hydroxide solution (100 ml) over night. The solvent was evaporated and the residue was purified on DEAE Cellulose ion exchange column using gradient of NH$_4$HCO$_3$ buffer (0.05–0.2M). The pure fractions were collected and lyophillized to give pure 3'-O-(3'-deoxy-β-D-adenosinyl)-β-L-2'-deoxyuridine (L-150)(0.486 g) as white solid.

EXAMPLE 10

Synthesis of β-L -dA Cordycepin dimer (L-151)

To a stirring solution of 2'-deoxy-β-L-adenosine (2.05 g, 8.16 mmol) in pyridine (75 ml) chilled in an ice bath, ClSiMe$_3$ (5.17 ml, 40.8 mmol) was added dropwise and stirred for 30 minutes. Benzoyl chloride (4.7 ml, 40.8 mmol) was then added dropwise and the reaction mixture was stirred at room temperature for two hours. This was cooled in an ice bath and water (15 ml) was added dropwise. 15 minutes later concentrated NH$_4$OH (15 ml) was added to give a solution approximately 2 M in ammonia. After 30 minutes the solvent was evaporated and the residue was dissolved in water and washed with ether. The water layer was concentrated and the N$^6$-benzoyl-2'-deoxy-β-L-adenosine was crystallized from water as white solid (2.48 g, 85.8%).

To a solution of N$^6$-benzoyl-2'-deoxy-β-L-adenosine (2.48 g, 6.98 mmol) in pyridine (100 ml) was added 4,4'-dimethoxy trityl chloride (3.55 g, 10.47 mmol) and DMAP (0.25 g, 2.09 mmol) and stirred at room temperature for 2 hours under argon. To complete the reaction, additional DMTCl (1.3 g) was added and stirred for another 2 hours. The reaction was quenched with the addition of MeOH (5 ml) and the solvent was evaporated. The residue was dissolved in EtOAc, washed with water, NaHCO$_3$ and brine. After drying over Na$_2$SO$_4$, the EtOAc layer was evaporated and the crude compound was purified on a silica gel column using 3–5% MeOH/CHCl, as solvent to give pure N$^6$-benzoyl-5'-O-(di-p-methoxy trityl)-2'-deoxy-β-L-adenosine (3.42 g, 74.5%) as pale yellow foam.

N$^6$-benzoyl-5'-O-(di-p-methoxy trityl)-2'-deoxy-β-L-adenosine (1.64 g, 2.5 mmol) was dissolved in anhydrous dichloromethane (50 ml). N,N-diisopropylethylamine (1.75 ml, 10.0 mmol) was added under argon followed by 2'-cyanoethyl-N,N-diisopropylchlorophosphoramidite (0.8 ml, 3.25 mmol). The reaction was stirred for 30 minutes and the solvent was evaporated. The residue was dissolved in 80% EtOAc/Et$_3$N (75 ml) and washed with water, NaHCO$_3$ and brine. The organic layer was evaporated and purified on a short silica gel column using a mixture of EtOAc, CH$_2$Cl$_2$ and Et$_3$N (40:50:10) to give N$^6$-Benzoyl-5'-O-(dimethoxytrityl)-β-L-2'-deoxyadenosine-3'-N,N-diisopropylcyanoethyl phosphoramidite in quantitative yield.

To a solution of N$^6$-Benzoyl-5'-O-(dimethoxytrityl)-β-L-2'-deoxyadenosine-3'-N,N-diisopropylcyanoethyl phosphoramidite (2.5 mmol) in anhydrous acetonitrile (60 ml), N$^6$-Benzoyl-2'-O-acetoxy-β-D-3'-deoxyadenosine (0.94 g, 2.36 mmol) in acetonitrile (40 ml) was added and stirred for 10 minutes under argon. To this solution, sublimed 1H-tetrazole (0.5 g, 7.2 mmol) was added and stirred over night. The solvent was evaporated and the residue was triturated with 70% EtOAc/ether and filtered. The filtrate was evaporated to give N$^6$-Benzoyl-5'-O-(dimethoxytrityl)-3'-[O-(2'-O-acetyl)-N$^6$-benzoyl-β-D-3-deoxy adenosinyl]-2'-deoxy-β-L-adenosine cyanoethyl phosphite ester as a foam and this was used in the next step without further purification.

The dimer N$^{6'}$-Benzoyl-5'-O-(dimethoxytrityl)-3'-[O-(2'-O-acetyl)-N$^6$-benzoyl-β-D-3-deoxy adenosinyl]-2'-deoxy-β-L-adenosine cyanoethyl phosphite was dissolved in THF (24 ml), pyridine (6 ml) and water (0.6 ml). Iodine crystals (0.63 g) were added portion wise until the iodine color persists. The reaction mixture was stirred for another 15 minutes and the excess iodine was removed by the addition of saturated sodium thiosulfate. The solvent was evaporated and the residue was dissolved in EtOAc and washed with water, NaHCO$_3$ and brine. EtOAc layer was evaporated and the residue was dissolved in 80% acetic acid/water solution (50 ml) and stirred for 1 hour. Then the solvent was evaporated and the crude product was purified on a silica gel column using 5–10% MeOH/CHCl$_3$ as solvent to give pure (2'-Acetoxy-N$^6$-benzoyl-3'-deoxy-β-D-adenosinyl)-N$^6$-benzoyl-β-L-2'-deoxyadenosinyl cyanoethyl phosphate ester (0.97 g) as a foam.

The dimer (2'-Acetoxy-N$^6$-benzoyl- 3'-deoxy-β-D-adenosinyl)-N$^6$-benzoyl-β-L-2'-deoxyadenosinyl cyanoethyl phosphate ester (0.97 g) was treated with ammonium hydroxide solution (100 ml) over night. The solvent was evaporated and the residue was purified on DEAE Cellulose ion exchange column using gradient of NH$_4$HCO$_3$ buffer (0.05–0.2 M). The pure fractions were collected and lyophillized to give pure compound 3'-O-(3'-deoxy-β-D-adenosinyl)-β-L-2'-deoxyadenosine (L-151) (0.55 g) as white solid.

EXAMPLE 11

Synthesis of α-L-dU, Cordycepin dimer (L-152)

α-L-dU (1.04 g, 4.5 mmol) was dissolved in dry pyridine (50 ml), to this solution was added 4,4'-dimethoxytrityl chloride (2.4 g, 6.86 mmol) and DMAP (0.11 g, 0.91 mmol). This was stirred under argon at room temperature for 2 hours and quenched with MeOH (5 ml). The solvent was evaporated, the residue was dissolved in EtOAc, washed with water, NaHCO$_3$ and brine. After drying and evaporation of the solvent, the crude material was purified on a silica gel column using 3–5% MeOH/CHCl$_3$ as solvent to give pure 5'-O-Dimethoxytrityl-α-L-2'-deoxyuridine (2.4 g., 99%) as white foam.

5'-O-Dimethoxytrityl-α-L-2'-deoxyuridine (1.73 g, 3.26 mmol) was dissolved in anhydrous dichloromethane (30 ml), N,N-diisopropylethylamine (2.3 ml, 13.04 mmol) was added under argon followed by 2'-cyanoethyl-N,N-diisopropylchlorophosphoramidite (0.95 ml, 4.23 mmol). The reaction was stirred for 30 minutes and the solvent was evaporated. The residue was dissolved in 80% EtOAc/Et$_3$N (75 ml) and washed with water, NaHCO$_3$ and brine. The organic layer was evaporated and purified on a short silica gel column using a mixture of EtOAc, CH$_2$CL$_2$ and Et$_3$N (40:50:10) to give 5'-O-Dimethoxytrityl-α-L-2'-deoxyuridine-3'-N,N-diisopropylcyanoethyl phosphoramidite (2.26 g, 95%) as a foam.

To a solution of 5'-O-Dimethoxytrityl-α-L -2'-deoxyuridine-3'-N,N-diisopropylcyanoethyl phosphoramidite (2.26 g, 3.09 mmol) in anhydrous acetonitrile (60 ml), N$^6$-Benzoyl-2'-O-acetoxy-β-D-3'-deoxyadenosine (1.35 g, 3.4 mmol) in acetonitrile (40 ml) was added and stirred for 10 minutes under argon. To this solution, sublimed 1H-tetrazole (0.65 g, 8.5 mmol) was added and stirred over night. The solvent was evaporated and the residue was triturated with 70% EtOAc/ether and filtered. The filtrate was evaporated to give 5'-O-Dimethoxytrityl-3'-[O-(2'-O-acetyl)-N$^6$-benzoyl-β-D-3'-deoxyadenosinyl]-2'-deoxy-α-L-uridine cyanoethyl phosphite ester as a foam and this was used in the next step without further purification.

The dimer 5'-O-Dimethoxytrityl-3'-[O-(2'-O-acetyl)-N$^6$-benzoyl-β-D-3'-deoxyadenosinyl]-2'-deoxy-α-L-uridine cyanoethyl phosphite ester was dissolved in THF (24 ml), pyridine (6 ml) and water (0.6 ml). Iodine crystals (0.7 g) were added portion wise until the iodine color persists. The reaction mixture was stirred for another 15 minutes and the excess iodine was removed by the addition of saturated sodium thiosulfate. The solvent was evaporated and the residue was dissolved in EtOAc and washed with water, NaHCO$_3$ and brine. EtOAc layer was evaporated and the residue was dissolved in 80% acetic acid/water solution (50 ml) and stirred for 1 hour. Then the solvent was evaporated and the crude product was purified on a silica gel column using 8–15% MeOH/CHCl$_3$ as solvent to give pure (2'-Acetoxy-N$^6$-Benzoyl-3'-deoxy-β-D-adenosinyl)-α-L-2'-deoxyuridinyl cyanoethyl phosphate ester (1.29 g) as a foam.

The dimer (2'-Acetoxy-N$^6$-Benzoyl-3'-deoxy-β-D-adenosinyl)-α-L-2'-deoxyuridinyl cyanoethyl phosphate ester (1.29 g) was treated with ammonium hydroxide solution (100 ml) over night, The solvent was evaporated and the residue was purified on DEAE Cellulose ion exchange column using gradient of NH$_4$HCO$_3$ buffer (0.05–0.2M). The pure fractions were collected and lyophillized to give pure 3'O-(3'-deoxy-β-D-adenosinyl)-α-L-2'-deoxyuridine (L-152) (0.856 g) as white solid.

EXAMPLE 12

Synthesis of β-L-dC, Cordycepin dimer (L-153)

To a solution of β-L-dCBz (1.7 g, 5.22 mmol) in pyridine (100 ml) was added 4,4'-dimethoxy trityl chloride (2.65 g, 7.83 mmol) and DMAP (0.13 g, 1.04 mmol) and stirred at room temperature for 2 hours under argon. To complete the reaction, additional DMTCl (0.9 g) was added and stirred for another 2 hours. The reaction was quenched with the addition of MeOH (5 ml) and the solvent was evaporated. The residue was dissolved in EtOAc, washed with water, NaHCO$_3$ and brine. After drying over Na$_2$SO$_4$, the EtOAc layer was evaporated and the crude compound was purified on a silica gel column using 3–5% MeOH/CHCl$_3$ as solvent to give pure N$^4$-Benzoyl-5'-O-(di-p-methoxy trityl)-2'-deoxy-β-L-cytidine (2.98 g, 90%) as pale yellow foam.

N$^4$-Benzoyl-5'-O-(di-p-methoxy trityl)-2'-deoxy-β-L-cytidine (1.7 g, 2.68 mmol) was dissolved in anhydrous dichloromethane (50 ml), N,N-diisopropylethylamine (1.9 ml, 10.72 mmol) was added under argon followed by 2'-cyanoethyl-N,N-diisopropylchlorophosphoramidite (0.85 ml, 3.5 mmol). The reaction was stirred for 30 minutes and the solvent was evaporated. The residue was dissolved in 80% EtOAc/Et$_3$N (75 ml) and washed with water, NaHCO$_3$ and brine. The organic layer was evaporated and purified on a short silica gel column using a mixture of EtOAc, CH$_2$Cl$_2$ and Et$_3$N (30:60:10) to give N$^4$-Benzoyl-5'-O-(dimethoxytrityl)-β-L-2'-deoxycytidine-3'-N,N-diisopropylcyanoethyl phosphoramidite (2.06 g, 92%) as a foam.

To a solution of N$^4$-Benzoyl-5'-O-(dimethoxytrityl)-β-L-2'-deoxycytidine-3'-N,N-diisopropylcyanoethyl phosphoramidite (2.06 g, 2.47 mmol) in anhydrous acetonitrile (100 ml), N$^6$-benzoyl-2'-O-acetoxy-β-D-3'-deoxyadenosine (1.08 g, 2.72 mmol) in acetonitrile (40 ml) was added and stirred for 10 minutes under argon. To this solution, sublimed 1H-tetrazole (0.52 g, 7.4 mmol) was added and stirred over night. The solvent was evaporated and the residue was triturated with 70% EtOAc/ether and filtered. The filtrate was evaporated to give N$^4$-Benzoyl-5'-O-dimethoxytrityl-3'-[O-(2'-O-acetyl)-N$^6$-benzoyl-β-D-3'-deoxyadenosinyl]-2'-deoxy-β-L-cytidine cyanoethyl phosphite ester as a foam and this was used in the next step without further purification.

The dimer N$^4$-Benzoyl-5'-O-dimethoxytrityl-3'-[O-(2'-O-acetyl)-N$^6$-benzoyl-β-D-3'-deoxyadenosinyl]-2'-deoxy-β-L-cytidine cyanoethyl phosphite ester was dissolved in THF (24 ml), pyridine (6 ml) and water (0.6 ml). Iodine crystals (0.55 g) were added portion wise until the iodine color persists. The reaction mixture was stirred for another 15 minutes and the excess iodine was removed by the addition of saturated sodium thiosulfate. The solvent was evaporated and the residue was dissolved in EtOAc and washed with water, NaHCO$_3$ and brine. EtOAc layer was evaporated and the residue was dissolved in 80% acetic acid/water solution (50 ml) and stirred for 1 hour. Then the solvent was evaporated and the crude product was purified on a silica gel column using 5–10% MeOH/CHCl$_3$ as solvent to give pure compound (2'-Acetoxy-N$^6$-benzoyl-3'-deoxy-β-D-adenosinyl)-N$^4$-Benzoyl-β-L-2'-deoxycitydinyl cyanoethyl phosphate ester (1.46 g) as a foam.

The dimer (2'-Acetoxy-N$^6$-benzoyl-3'-deoxy-β-D-adenosinyl)-N$^4$-Benzoyl-β-L-2'-deoxycitydinyl cyanoethyl phosphate ester (1.46 g) was treated with ammoniun hydroxide solution (100 ml) over night. The solvent was evaporated and the residue was purified on DEAE Cellulose ion exchange column using gradient of NH$_4$HCO$_3$ buffer (0.05–0.2 M). The pure fractions were collected and lyophillized to give pure 3'-O-(3'-deoxy-β-D-adenosinyl)-β-L-2'-deoxycytidine (L-153) (0.81 g) as white solid.

EXAMPLE 13

Synthesis of α-L-dC, Cordycepin dimer (L-154)

To a solution of α-L -dC (1.6 g, 4.88 mmol) in pyridine (100 ml) was added 4,4'-dimethoxy trityl chloride (2.43 g, 7.2 mmol) and DMAP (0.13 g, 1.04 mmol) and stirred at room temperature for 2 hours under argon. To complete the reaction, additional DMTCl (1.0 g) was added and stirred for another 2 hours. The reaction was quenched with the addition of MeOH (5 ml) and the solvent was evaporated. The residue was dissolved in EtOAc, washed with water NaHCO$_3$ and brine. After drying over Na$_2$SO$_4$, the EtOAc layer was evaporated and the crude compound was purified on a silica gel column using 3–5% MeOH/CHCl$_3$ as solvent to give pure N$^4$-Benzoyl-5'-O-(di-p-methoxy trityl)-2'-deoxy-α-L-cytidine (2.34 g, 76%) as pale yellow foam.

N$^4$-Benzoyl-5'-O-(di-p-methoxytrityl)-2'-deoxy-α-L-cytidine (1.84 g, 2.9 mmol) was dissolved in anhydrous dichloromethane (50 ml). N,N-diisopropylethylamine (2.0 ml, 11.6 mmol) was added under argon followed by 2'-cyanoethyl-N,N-diisopropylchlorophosphoramidite (0.85 ml, 3.5 mmol). The reaction was stirred for 30 minutes and the solvent was evaporated. The residue was dissolved in 80% EtOAc/Et$_3$N (75 ml) and washed with water, NaHCO$_3$ and brine. The organic layer was evaporated and purified on a short silica gel column using a mixture of EtOAc, hexane and Et$_3$N (50:40:10) to give N$^4$-Benzoyl-5'-O-(dimethoxytrityl)-α-L-2'-deoxycytidine-3'-N,N-diisopropylcyanoethyl phosphoramidite (2.01 g, 83%) as a foam.

To a solution of compound N$^4$-Benzoyl-5'-O-(dimethoxytrityl)-α-L-2'-deoxycytidine-3'-N,N-diisopropylcyanoethyl phosphoramidite (2.01 g, 2.4 mmol) in anhydrous acetonitrile (100 ml),N$^6$-Benzoyl-2'-O-acetoxy-β-D-3'-deoxyadenosine (1.05 g, 2.65 mmol) in acetonitrile (40 ml) was added and stirred for 10 minutes under argon. To this solution, sublimed 1-H-tetrazole (0.5 g, 7.2 mmol) was added and stirred over night. The solvent was evaporated and the residue was triturated with 70% EtOAc/ether and filtered. The filtrate was evaporated to give N$^4$-Benzoyl-5'-O-(dimethoxytrityl)-3'-[O-(2'-acetyl)-N$^6$-Benzoyl-β-D-3'-deoxy adenosinyl]-2'-deoxy-α-L-cytidine cyanoethyl phosphite ester as a foam and this was used in the next step without purification.

The dimer N$^4$-Benzoyl-5'-O-(dimethoxytrityl)-3'-[O-(2'-acetyl)-N$^6$-Benzoyl-β-D-3'-deoxy adenosinyl]-2'-deoxy-α-L-cytidine cyanoethyl phosphite ester was dissolved in THF (24 ml), pyridine (6 ml) and water (0.6 ml). Iodine crystals (0.5 g) were added portion wise until the iodine color persists. The reaction mixture was stirred for another 15 minutes and the excess iodine was removed by the addition of saturated sodium thiosulfate. The sulfate was evaporated and the residue was dissolved in EtOAc and washed with water, NaHCO$_3$ and brine. EtOAc layer was evaporated and the residue was dissolved in 80% acetic acid/water solution (50 ml) and stirred for 1 hour. Then the solvent was evaporated and the crude product was purified on a silica gel column using 5–10% MeOH/CHCl$_3$ as solvent to give pure (2'-Acetoxy-N$^{6'}$-Benzoyl-3'-deoxy-β-D-adenosinyl)-N$^4$-Benzoyl-α-L-2-deoxycitydinyl cyanoethyl phosphate ester (1.8 g) as a foam.

The dimer (2'-Acetoxy-N$^6$-Benzoyl-3'-deoxy-β-D-adenosinyl)-N$^4$-Benzoyl-α-L-2-deoxycitydinyl cyanoethyl phosphate ester (1.8 g) was treated with ammonium hydroxide solution (100 ml) over night, The solvent was evaporated and the residue was purified on DEAE Cellulose ion exchange column using gradient of NH$_4$HCO$_3$ buffer (0.05–0.2M). The pure fractions were collected and lyophillized to give pure 3'-O(3'-deoxy-β-D-adenosinyl)-α-L-2'-deoxycytidine (L-154) (1.08 g) as white solid.

EXAMPLE 14

Synthesis of α-L-dA, Cordycepin dimer (L-155)

To a stirring solution of 2'-deoxy-α-L-adenosine (2.05 g, 8.16 mmol) in pyridine (75 ml) chilled in an ice bath, ClSiMe$_3$ (5.17 ml, 40.8 mmol) was added dropwise and stirred for 30 minutes. Benzoyl chloride (4.7 ml, 40.8 mmol) was then added dropwise and the reaction mixture was stirred at room temperature for two hours. This was cooled in an ice bath and water (15 ml) was added dropwise, 15 minutes later concentrated NH$_4$OH (15 ml) was added to give a solution approximately 2M in ammonia. After 30 minutes the solvent was evaporated and the residue was dissolved in water and washed with ether. The water layer was concentrated and the N$^6$-Benzoyl-2'-deoxy-α-L-adenosine crystallized from water as white solid (2.48 g, 85.8%).

To a solution of compound N$^6$-Benzoyl-2'-deoxy-α-L-adenosine (2.48 g, 6.98 mmol) in pyridine (100 ml) was added 4,4'-dimethoxy trityl chloride (3.55 g, 10.47 mmol) and DMAP (0.25 g, 2.09 mmol) and stirred at room temperature for 2 hours under argon. To complete the reaction, additional DMTCl (1.3 g) was added and stirred for another 2 hours. The reaction was quenched with the addition of MeOH (5 ml) and the solvent was evaporated. The residue was dissolved in EtOAc, washed with water, NaHCO$_3$ and brine. After drying over Na$_2$SO$_4$, the EtOAc layer was evaporated and the crude compound was purified on a silica gel column using 3–5% MeOH/CHCl$_3$ as solvent to give pure N$^6$-Benzoyl-5'-O-(di-p-methoxy trityl)-2'-deoxy-α-L-adenosine (3.42 g, 74.5%) as pale yellow foam.

N$^6$-Benzoyl-5'-O-(di-p-methoxy trityl)-2'-deoxy-α-L-adenosine (1.64 g, 2.5 mmol) was dissolved in anhydrous dichloromethane (50 ml). N,N-diisopropylethylamine (1.75 ml, 10.0 mmol) was added under argon followed by 2'-cyanoethyl-N,N-diisopropylchlorophosphoramidite (0.8 ml, 3.25 mmol). The reaction was stirred for 30 minutes and the solvent was evaporated. The residue was dissolved in 80% EtOAc/Et$_3$N (75 ml) and washed with water, NaHCO$_3$ and brine. The organic layer was evaporated and purified on a short silica gel column using a mixture of EtOAc, CH$_2$Cl$_2$ and Et$_3$N (40:50:10) to give N$^6$-Benzoyl-5'-O-(dimethoxytrityl)-α-L-2'-deoxyadenosine-3'-N,N-diisopropylcyanoethyl phosphoramidite in quantitative yield.

To a solution of N$^6$-Benzoyl-5'-O-(dimethoxytrityl)-α-L-2'-deoxyadenosine-3'-N,N-diisopropylcyanoethyl phosphoramidite(2.5 mmol) in anhydrous acetonitrile (60 ml), N$^6$-Benzoyl-3'-O-acetoxy-β-D-2'-deoxyadenosine (0.94 g, 2.36 mmol) in acetonitrile (40 ml) was added and stirred for 10 minutes under argon. To this solution, sublimed 1H-tetrazole (0.5 g, 7.2 mmol) was added and stirred overnight. The solvent was evaporated and the residue was triturated with 70% EtOAc/ether and filtered. The filtrate was evaporated to give N$^6$-Benzoyl-5'-O-dimethoxytrityl-3'-[O-(2'-)-acetyl)-N$^6$-benzoyl-β-D-3'-deoxy adenosinyl]-2'-deoxy-α-L-adenosine cyanoethyl phosphite ester as a foam and this was used in the next step without further purification.

The dimer N$^6$-Benzoyl5'-O-dimethoxytrityl-3'-[O-(2'-)-acetyl)-N$^6$-benzoyl-β-D-3'-deoxy adenosinyl]-2'-deoxy-α-L-adenosine cyanoethyl phosphite ester was dissolved in THF (24 ml), pyridine (6 ml) and water (0.6 ml). Iodine crystals (0.63 g) were added portion wise until the iodine color persists. The reaction mixture was stirred for another 15 minutes and the excess iodine was removed by the addition of saturated sodium thiosulfate. The solvent was evaporated the residue was dissolved in EtOAc and washed with water, NaHCO$_3$ and brine. EtOAc layer was evaporated and the residue was dissolved in 80% acetic acid/water solution (50 ml) and stirred for 1 hour. Then the solvent was evaporated and the crude product was purified on a silica gel column using 5–10% MeOH/CHCl$_3$ as solvent to give pure compound (2'-Acetoxy-N$^6$-benzoyl-3'-deoxy-β-D-adenosinyl)-N$^6$-benzoyl-α-L-2'-deoxyadenosinyl cyanoethyl phosphate ester (0.97 g) as a foam.

The dimer (2'-Acetoxy-N$^6$-benzoyl-3'-deoxy-β-D-adenosinyl)-N$^6$-benzoyl-α-L-2'-deoxyadenosinyl cyanoethyl phosphate ester(0.97 g) was treated with ammonium hydroxide solution (100 ml) overnight. The solvent was evaporated and the residue was purified on DEAE Cellulose ion exchange column using gradient of NH$_4$HCO$_3$ buffer (0.05–0.2 M). The pure fractions were collected and lyophillized to give pure 3-O-(3'-deoxy-β-D-adenosinyl)-β-L-2'-deoxyadenosine (0.55 g)(L-155) as white solid.

EXAMPLE 15

Synthesis of β-L-dA, β-D-dA (L-210)

To a stirring solution of 2'-deoxy-β-L-adenosine (2.05 g, 8.16 mmol) in pyridine (75 ml) chilled in an ice bath, ClSiMe$_3$ (5.17 ml, 40.8 mmol) was added dropwise and stirred for 30 minutes. Benzoyl chloride (4.7 ml, 40.8 mmol) was then added dropwise and the reaction mixture was stirred at room temperature for two hours. This was cooled in an ice bath, and water (15 ml) was added dropwise. 15 minutes later concentrated NH$_4$OH (15 ml) was added to give a solution approximately 2 M in ammonia. After 30 minutes, the solvent was evaporated and the residue was dissolved in water and washed with ether. The water layer was concentrated, and the N$^6$-Benzoyl-2'-deoxy-β-L-adenosine was crystallized from water as white solid (2.48 g, 85.8%).

To a solution of N$^6$-Benzoyl-2'-deoxy-β-L-adenosine (2.48 g, 6.98 mmol) in pyridine (100 ml) was added 4,4'-dimethoxy trityl chloride (3.55 g, 10.47 mmol) and DMPA (0.25 g, 2.09 mmol) and stirred at room temperature for 2 hours under argon. To complete the reaction, additional DMTCl (1.3 g) was added and stirred for another 2 hours. The reaction was quenched with the addition of MeOH (5 ml), and the solvent was evaporated. The residue was dissolved in EtOAc, washed with water, NaHCO$_3$ and brine. After drying over Na$_2$SO$_4$, the EtOAc layer was evaporated and the crude compound was purified on a silica gel column using 3/5% MeOH/CHCl$_3$ as solvent to give pure N$^6$-Benzoyl-5'-O-(di-p-methoxy trityl)-2'-deoxy-β-L-adenosine (3.42 g, 74.5%) as pale yellow foam.

N$^6$-Benzoyl-5'-O-(di-p-methoxy trityl)-2'-deoxy-β-L-adenosine(1.71 g, 2.61 mmol) was dissolved in anhydrous dichloromethane (50 ml). N,N-diisopropylethylamine (1.8 ml, 10.34 mmol) was added under argon followed by 2'-cyanoethyl-N,N-diisopropylchlorophosphoramidite (1.0 ml, 4.47 mmol). The reaction was stirred for 30 minutes, and the solvent was evaporated. The residue was dissolved in 80% EtOAc/Et$_3$N (75 ml) and washed with water, NaHCO$_3$ and brine. The organic layer was evaporated and purified on a short silica gel column using a mixture of EtOAc, hexane and Et$_3$N (50:40:10) to give N$^6$-Benzoyl-5'-O-(dimethoxytrityl)-β-L -2'-deoxyadenosine-3'-N,N-diisopropylcyanoethyl phosphoramidite(1.87 g, 84%) as a foam.

To a solution of N$^6$-Benzoyl-5'-O-(dimethoxytrityl)-β-L-2'-deoxyadenosine-3'-N,N-diisopropylcyanoethyl phosphoramidite(1.87 g, 2.18 mmol) in anhydrous acetonitrile (60 ml), N$^6$-Benzoyl-3'-O-acetoxy-β-D-2'-deoxyadenosine (0.95 g, 2.4 mmol) in acetonitrile (40 ml) was added and stirred for 10 minutes under argon. To this solution, sublimed 1H-tetrazole (0.46 g, 6.6 mmol) was added and stirred overnight. The solvent was evaporated, and the residue was triturated with 70% EtOAc/ether and filtered. The filtrate was evaporated to give N$^6$-Benzoyl-5'-O-dimethoxytrityl-3'-[O-(3'-O'acetyl)-N$^6$-benzoyl-β-D-2'-deoxy adenosinyl]-2'-deoxy-β-L-adenosine cyanoethyl phosphite ester as a foam, and this was used in the next step without further purification.

The dimer N$^6$-Benzoyl-5'-O-dimethoxytrityl-3'-[O-(3'-O'acetyl)-N$^6$-benzoyl-β-D-2'-deoxy adenosinyl]-2'-deoxy-β-L-adenosine cyanoethyl phosphite ester was dissolved in THF (24 ml), pyridine (6 ml) and water (0.6 ml). Iodine crystals (0.5 g) were added portion wise until the iodine color persists. The reaction mixture was stirred for another 15 minutes, and the excess iodine was removed by the addition of saturated sodium thiosulfate. The solvent was evaporated, and the residue was dissolved in EtOAc and washed with water, NaHCO$_3$ and brine. EtOAc layer was evaporated, and the residue was dissolved in 80% acetic acid/water solution (50 ml) and stirred for 1 hour. Then the solvent was evaporated, and the crude product was purified on a silica gel column using 5–10% MeOH/CHCl$_3$ as solvent to give pure compound (3'-Acetoxy-N$^6$-benzoyl-2'-deoxy-β-D-adenosinyl)-N$^6$-benzoyl-β-L-2'-deoxyadenosinyl cyanoethyl phosphate ester (0.13 g) as a foam.

The dimer (3'-Acetoxy-N$^6$-benzoyl-2'-deoxy-β-D-adenosinyl)-N$^6$-benzoyl-β-L-2'-deoxyadenosinyl cyanoethyl phosphate ester(1.3 g) was treated with ammonium hydroxide solution (100 ml) overnight. The solvent was evaporated, and the residue was purified on DEAE Cellulose ion exchange column using gradient of NH$_4$HCO$_3$ buffer (0.05–0.2 M). The pure fractions were collected and lyophillized to give pure 3'-O-(2'-deoxy-β-D-adenosinyl)-β-L-2'-deoxyadenosine (L-210) (0.640 g) as white solid.

All patents and publications mentioned in the specifications are indicative of the levels of those skilled in the art to which the invention pertains. All patents and publications are herein incorporated by reference to the same extent as if each individual publication was specifically and individually indicated to be incorporated by reference.

One skilled in the art readily appreciates that the patent invention is well adapted to carry out the objectives and obtain the ends and advantages mentioned as well as those inherent therein. Dimers, pharmaceutical compositions, treatments, methods, procedures and techniques described herein are presently representative of the preferred embodiments and are intended to be exemplary and are not intended as limitations of the scope. Changes therein and other uses will occur those skilled in the art which are encompassed within the spirit of the invention or defined by the scope of the pending claims.

What is claimed is:

1. A method for treating a *Plasmodium falciparum* infection in a mammal comprising administering to an afflicted mammal a therapeutically effect amount of a compound having the formula:

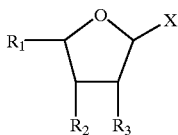

or a pharmaceutically acceptable salt thereof,
wherein $R_1$ is —$CH_2OH$ in the L-configuration;
wherein $R_2$ and $R_3$ are selected from the group consisting of —H and —OH; and
wherein X is a nitrogenous base consisting of purines and pyrimidines.

2. A method for treating a *Plasmodium falciparum* infection in a mammal comprising administering to said mammal a therapeutically effective amount of a compound having the formula:

wherein X is a $PO_4$ or $S=PO_3$;
wherein $R_1$ and $R_2$ are the same or different nucleosides;
wherein $R_1$ and $R_2$ are selected from the group consisting of β-D-deoxyfluorouridine, α-L-deoxyfluorouridine, β-L-deoxyfluorouridine, α-L-deoxycytidine, β-L-deoxycytidine, β-L-deoxyuridine, β-L-deoxyguanosine, β-L-deoxyadenosine, α-L-doxyadenosine and nitrobenzylthionsine; and
wherein $R_1$ and $R_2$ are attached to X through —OH groups.

3. The method according to claim 2 wherein $R_1$ is β-D-deoxyfluorouridine.

4. The method according to claim 2 wherein $R_1$ is α-L-deoxyfluorouridine.

5. The method according to claim 2 wherein $R_1$ is β-L-deoxyfluorouridine.

6. The method according to claim 2 wherein $R_1$ is α-L-deoxycytidine.

7. The method according to claim 2 wherein $R_1$ is β-L-deoxycytidine.

8. The method according to claim 2 wherein $R_1$ is β-L-deoxyuridine.

9. The method according to claim 2 wherein $R_1$ is β-L-deoxyguanosine.

10. The method according to claim 2 wherein $R_1$ is β-L-deoxyadenosine.

11. The method according to claim 2 wherein $R_1$ is α-L-deoxyadenosine.

12. The method according to claim 2 wherein $R_1$ is nitrobenzylthionosine.

13. The method of claim 1, wherein $R_2$ and $R_3$ are each —OH, and wherein X is adenine.

14. The method of claim 13, wherein $R_3$ is oriented equatorially, wherein $R_2$ is axially oriented, and wherein adenine is axially oriented.

15. The method of claim 1, wherein $R_2$ is —OH and $R_3$ is —H, and wherein X is 5-fluorouracil.

16. The method of claim 15, wherein $R_2$ is oriented axially, and wherein 5'-fluorouracil is oriented axially.

17. The method of claim 1, wherein $R_2$ and $R_3$ are each —OH, and wherein X is guanine.

18. The method of claim 17, wherein $R_2$ and $R_3$ are each oriented axially, and wherein guanine is oriented equatorially.

19. The method of claim 1, wherein $R_2$ and $R_3$ are each —OH, and wherein X is adenine.

20. The method of claim 19, wherein $R_2$ and $R_3$ are each oriented axially, and wherein adenine is oriented equatorially.

21. The method of claim 1, wherein $R_2$ and $R_3$ are each —OH, and wherein X is inine.

22. The method of claim 21, wherein $R_2$ and $R_3$ are each oriented axially, and wherein inine is oriented equatorially.

23. The method of claim 1, wherein $R_2$ and $R_3$ are each —OH, and wherein X is mercaptoguanine.

24. The method of claim 23, wherein $R_2$ and $R_3$ are each oriented axially, and wherein mercaptoguanine is oriented equatorially.

25. The method of claim 1, wherein $R_2$ is —OH and $R_1$ is —H, and wherein X is adenine.

26. The method of claim 25, wherein $R_2$ is oriented axially, and wherein adenine is oriented equatorially.

27. The method of claim 1, wherein $R_2$ is —OH and R1 is —H, and wherein X is deoxyinine.

28. The method of claim 27, wherein $R_2$ is oriented axially, and wherein deoxyinosine is attached to the β hydrogen on the ribose ring.

29. The method of claim 1, wherein $R_2$ is —OH and R3 is —OH, and wherein X is adenine.

30. The method of claim 29, wherein $R_2$ and $R_3$ are each oriented axially, and wherein adenine is oriented axially.

31. The method of claim 1, wherein $R_2$ is —OH and $R_3$ is —H, and wherein X is 3-aminopyrine, and further wherein the point of attachment of said aminopurine to the ribose ring is hydrogen 3.

32. The method of claim 31, wherein $R_2$ is oriented axially, and wherein aminopurine is oriented axially.

33. The method of claim 1, wherein $R_2$ is —OH and $R_3$ is —H, and wherein X is guanine.

34. The method of claim 33, wherein $R_2$ is oriented axially, and wherein guanine is oriented equatorially.

35. The method of claim 1, wherein $R_2$ and $R_3$ are each —H, and wherein X is adenine.

36. The method of claim 35, wherein adenine is oriented equatorially.

37. The method of claim 1, wherein $R_2$ and $R_3$ are each —H, and wherein X is adenine.

38. The method of claim 37, wherein adenine is oriented axially.

39. The method of claim 1, wherein $R_2$ and $R_3$ are each —OH, and wherein X is 6-thiopurine.

40. The method of claim 39, wherein $R_2$ and $R_3$ are each axially oriented and 6-thiopurine is oriented equatorially.

41. The method of claim 1, wherein $R_2$ is —OH and $R_3$ is —H, and wherein X is 5-fluorouracil.

42. The method of claim 41, wherein $R_2$ is equatorially oriented, and wherein the 5-fluorouracil is attached to the α hydrogen on the ribose ring.

43. The method of claim 1, wherein $R_2$ and $R_3$ are each —OH, and wherein X is 5-fluorouracil.

44. The method of claim 43, wherein $R_2$ is oriented axially, and wherein 5'-fluorouracil oriented axially.

45. A method for treating a *Plasmodium falciparum* infection in a mammal comprising administering to an afflicted mammal a therapeutically effective amount of a nucleoside dimer comprising: β-D-deoxyfluorouridine, β-L-adenosine, and a suitable moiety for linking the two said nucleosides.

46. A method for treating a *Plasmodium falciparum* infection in a mammal comprising administering to an afflicted mammal a therapeutially effective amount of a compound having a non-stereospecific formula:

[structure: furanose ring with $R_2O$— substituent, X substituent, and $OR_1$ substituent]

wherein $R_1$ and $R_2$ are each either $(CH_3COSCH_2CH_2O)_2P{=}O$ or —H; and wherein X is a purine or pyrimidine.

47. The method of claim 46, herein $R_1$ is $(CH_3COSCH_2CH_2O)_2P{=}O$, wherein $R_2$ is —H, wherein —$OR_1$ is oriented equatorially, wherein —$OR_2$ is oriented axially, and wherein —X is oriented axially.

48. The method of claim 46, herein R is —H, wherein $R_2$ is $(CH_3COSCH_2CH_2O)_2P{=}O$, wherein —$OR_1$ is oriented equatorially, wherein —$OR_2$ is oriented axially, and wherein —X is oriented axially.

49. The method of claim 46, wherein $R_1$ and $R_2$ are each $(CH_3COSCH_2CH_2O)_2P{=}O$, wherein —$OR_1$ is oriented equatorially, wherein —$OR_2$ is oriented axially, and wherein —X is oriented axially.

50. The method of claim 46, wherein $R_1$ is —H, wherein $R_2$ is $(CH_3COSCH_2CH_2O)_2P{=}O$, wherein —$OR_1$ is oriented axially, wherein —$OR_2$ is oriented equatorially, and wherein —X is oriented equatorially.

51. The method of claim 46, wherein $R_1$ and $R_2$ are each $(CH_3COSCH_2CH_2O)_2P{=}O$, wherein —$OR_1$ is oriented axially, wherein —$OR_2$ is oriented equatorially, and wherein —X is oriented equatorially.

52. The method of claim 46, wherein $R_1$ is —H, wherein $R_2$ is $(CH_3COSCH_2CH_2O)_2P{=}O$, wherein —$OR_1$ is oriented axially, wherein —$OR_2$ is oriented equatorially, and wherein —X is oriented axially.

53. The method of claim 46, wherein $R_1$ and $R_2$ are each $(CH_3COSCH_2CH_2O)_2P{=}O$, wherein —$OR_1$ is oriented axially, wherein —$OR_2$ is oriented equatorially, and wherein —X is oriented axially.

54. A method for treating a *Plasmodium falciparum* infection in a mammal comprising administering to an afflicted mammal a therapeutically effective amount of a compound having a formula:

$$R_1-X-R_2;$$

wherein $R_1$ is selected from the group consisting of purines and pyrimidines;

wherein $R_2$ is $(CH_3COSCH_2CH_2O)_2P{=}O$; and wherein X is a suitable linking group.

55. A method for treating a *Plasmodium falciparum* infection in a mammal comprising administering to an afflicted mammal a therapeutically effective amount of a compound having a formula:

$$R_1-X-R_2;$$

wherein $R_1$ is selected from the group consisting of purines and pyrimidines;

wherein $R_2$ is selected from the group consisting of purines and pyrimidines; and wherein X is a suitable linking group.

\* \* \* \* \*